US010815484B2

(12) United States Patent
Chinnaiyan et al.

(10) Patent No.: US 10,815,484 B2
(45) Date of Patent: Oct. 27, 2020

(54) COMPOSITIONS AND METHODS FOR TREATING CANCER

(71) Applicant: The Regents of the University of Michigan, Ann Arbor, MI (US)

(72) Inventors: Arul Chinnaiyan, Ann Arbor, MI (US); Yasuyuki Hosono, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/195,185

(22) Filed: Nov. 19, 2018

(65) Prior Publication Data

US 2019/0153449 A1    May 23, 2019

Related U.S. Application Data

(60) Provisional application No. 62/590,072, filed on Nov. 22, 2017.

(51) Int. Cl.
*C12N 15/113* (2010.01)
*A61P 35/00* (2006.01)

(52) U.S. Cl.
CPC .......... *C12N 15/1135* (2013.01); *A61P 35/00* (2018.01); *C12N 2310/113* (2013.01); *C12N 2310/14* (2013.01); *C12N 2310/20* (2017.05); *C12N 2320/30* (2013.01)

(58) Field of Classification Search
None
See application file for complete search history.

(56) References Cited

U.S. PATENT DOCUMENTS

| | | | |
|---|---|---|---|
| 2014/0073525 A1 | 3/2014 | Chang et al. | |
| 2016/0160295 A1 | 6/2016 | Chinnaiyan et al. | |
| 2019/0153449 A1 | 5/2019 | Chinnaiyan et al. | |
| 2019/0307787 A1 | 10/2019 | Chinnaiyan et al. | |

FOREIGN PATENT DOCUMENTS

| | | |
|---|---|---|
| WO | WO 2014/205555 | 12/2014 |
| WO | WO 2016/094420 | 6/2016 |
| WO | WO 2017/007941 A1 | 1/2017 |
| WO | WO 2018/006074 A2 | 1/2018 |
| WO | WO 2019/103967 | 5/2019 |
| WO | WO 2019/199733 | 10/2019 |

OTHER PUBLICATIONS

Hosono et al., Cell vol. 171(7):1559-1572, Dec. 14, 2017.*
Abate-Shen et al., "Molecular genetics of prostate cancer." Genes Dev. Oct. 1, 2000;14(19):2410-34.
Barretina et al. "The Cancer Cell Line Encyclopedia Enables Predictive Modelling of Anticancer Drug Sensitivity" Nature. Mar. 28, 2012;483(7391):603-7.
Bejerano et al., "Ultraconserved elements in the human genome." Science. May 28, 2004;304(5675):1321-5.
Bell et al. "Insulin-like Growth Factor 2 mRNA-binding Proteins (IGF2BPs): Post-Transcriptional Drivers of Cancer Progression?" Cell Mol Life Sci. Aug. 2013;70(15):2657-75.
Birney et al."Identification and Analysis of Functional Elements in 1% of the Human Genome by the ENCODE Pilot Project" Nature. Jun. 14, 2007;447(7146):799-816.
Bozgeyik et al., "OncoLncs: Long Non-Coding RNAs with Oncogenic Functions" Mol Biol 2016, 5:3, 1000162, p. 1-13.
Cabili et al., "Integrative annotation of human large intergenic noncoding RNAs reveals global properties and specific subclasses." Genes Dev. Sep. 15, 2011;25(18):1915-27.
Calin et al., "Ultraconserved Regions Encoding ncRNAs Are Altered in Human Leukemias and Carcinomas" Cancer Cell. Sep. 2007;12(3):215-29.
Cancer Genome Atlas, "Comprehensive molecular portraits of human breast tumours." Nature. Oct. 4, 2012;490(7418):61-70.
Chen et al., "LIFR is a breast cancer metastasis suppressor upstream of the Hippo-YAP pathway and a prognostic marker." Nat Med. Oct. 2012;18(10):1511-7.
Cong et al., "Multiplex Genome Engineering Using CRISPR/Cas Systems" Science. Feb. 15, 2013;339(6121):819-23.
Consortium "The Genotype-Tissue Expression (GTEx) Project" Nat Genet. Jun. 2013;45(6):580-5.
Crea, Francesco et al. "Identification of a long non-coding RNA as a novel biomarker and potential therapeutic target for metastatic prostate cancer" Oncotarget, vol. 5, No. 3, Feb. 15, 2014, pages.
Curtis et al., "The genomic and transcriptomic architecture of 2,000 breast tumours reveals novel subgroups." Nature. Apr. 18, 2012;486(7403):346-52.
Derrien et al., "The GENCODE v7 catalog of human long noncoding RNAs: analysis of their gene structure, evolution, and expression." Genome Res. Sep. 2012;22(9):1775-89.
Dimitrieva et al., "UCNEbase—a database of ultraconserved noncoding elements and genomic regulatory blocks." Nucleic Acids Res. Jan. 2013;41(Database issue):D101-9.
Dovey et al., "Oncogenic NRAS Cooperates With p53 Loss to Generate Melanoma in Zebrafish" Zebrafish. Dec. 2009;6(4):397-404.
El-Shewy et al., "The Insulin-Like Growth Factor Type 1 and Insulin-Like Growth Factor Type 2/mannose-6-phosphate Receptors Independently Regulate ERK1/2 Activity in HEK293 Cells" J Biol Chem. Sep. 7, 2007;282(36):26150-7.
Engreitz et al., "RNA-RNA Interactions Enable Specific Targeting of Noncoding RNAs to Nascent Pre-mRNAs and Chromatin Sites" Cell. Sep. 25, 2014;159(1):188-199.
EP Search Report, EP Patent Application No. 15867280.8, dated Jun. 19, 2018, 14 pages.
Epstein et al., "The pathological interpretation and significance of prostate needle biopsy findings: implications and current controversies." J Urol. Aug. 2001;166(2):402-10.

(Continued)

*Primary Examiner* — Sean McGarry

(74) *Attorney, Agent, or Firm* — Casimir Jones, S.C.; Tanya Arenson

(57) ABSTRACT

Provided herein are compositions and methods for treating cancer. In particular, provided herein are compositions, methods, and uses of inhibitors of THOR for treating cancer.

11 Claims, 39 Drawing Sheets

Specification includes a Sequence Listing.

(56) References Cited

OTHER PUBLICATIONS

Etzioni et al., "Cancer surveillance series: interpreting trends in prostate cancer—part III: Quantifying the link between population prostate-specific antigen testing and recent declines in prostate cancer mortality." J Natl Cancer Inst. Jun. 16, 1999;91(12):1033-9.
Faghihi et al., "Expression of a Noncoding RNA Is Elevated in Alzheimer's Disease and Drives Rapid Feed-Forward Regulation of Beta-Secretase" Nat Med. Jul. 2008;14(7):723-30.
Finn et al., "Pfam: the protein families database." Nucleic Acids Res. Jan. 2014;42(Database issue):D222-30.
GenBank Accession No. AL391244, retrieved Dec. 13, 2012, 16 pages.
Giraldez et al., "MicroRNAs Regulate Brain Morphogenesis in Zebrafish" Science. May 6, 2005;308(5723):833-8.
Gluck et al., "TP53 genomics predict higher clinical and pathologic tumor response in operable early-stage breast cancer treated with docetaxel-capecitabine ± trastuzumab." Breast Cancer Res Treat. Apr. 2012;132(3):781-91.
Gong et al., "lncRNAs Transactivate STAU1-mediated mRNA Decay by Duplexing With 3' UTRs via Alu Elements" Nature. Feb. 10, 2011;470(7333):284-8.
Grasso et al., "The mutational landscape of lethal castration-resistant prostate cancer." Nature. Jul. 12, 2012;487(7406):239-43.
Gupta et al., "Long Non-Coding RNA HOTAIR Reprograms Chromatin State to Promote Cancer Metastasis" Nature. Apr. 15, 2010;464(7291):1071-6.
Guttman et al., "Ab initio reconstruction of cell type-specific transcriptomes in mouse reveals the conserved multi-exonic structure of lincRNAs." Nat Biotechnol. May 2010;28(5):503-10.
Hafner et al., "Transcriptome-wide Identification of RNA-binding Protein and microRNA Target Sites by PAR-CLIP" Cell. Apr. 2, 2010;141(1):129-41.
Hämmerle et al., "Posttranscriptional Destabilization of the Liver-Specific Long Noncoding RNA HULC by the IGF2 mRNA-binding Protein 1 (IGF2BP1)" Hepatology. Nov. 2013;58(5):1703-12.
Hofmann et al., "Genome-wide analysis of cancer/testis gene expression." Proc Natl Acad Sci U S A. Dec. 23, 2008;105(51):20422-7. 6 pages.
Hosono et al., "Oncogenic Role of THOR, a Conserved Cancer/Testis Long Non-coding RNA" Cell. Dec. 14, 2017;171(7):1559-1572.e20.
Hudson et al., "Transcription Signatures Encoded by Ultraconserved Genomic Regions in Human Prostate Cancer" Mol Cancer. Feb. 14, 2013;12:13.
Hwang et al., "Efficient Genome Editing in Zebrafish Using a CRISPR-Cas System" Nat Biotechnol. Mar. 2013;31(3):227-9.
International Search Report dated May 6, 2016, PCT/US2015/064525, Filed Dec. 8, 2015. 17 Pages.
International Search Report of related PCT/US2018/061802, dated Feb. 19, 2019, 18 pages.
International Search Report of related PCT/US2019/026466, dated Jul. 2, 2019, , 12 pages.
Iyer et al., "The Landscape of Long Noncoding RNAs in the Human Transcriptome" Nat Genet. Mar. 2015;47(3):199-208.
Jacobsen et al., "Incidence of prostate cancer diagnosis in the eras before and after serum prostate-specific antigen testing." JAMA. Nov. 8, 1995;274(18):1445-9.
Kauffmann et al., "High Expression of DNA Repair Pathways Is Associated With Metastasis in Melanoma Patients" Oncogene. Jan. 24, 2008;27(5):565-73.
Kim et al., "Widespread Transcription at Neuronal Activity-Regulated Enhancers" Nature. May 13, 2010;465(7295):182-7.
Kretz et al., "Control of Somatic Tissue Differentiation by the Long Non-Coding RNA TINCR" Nature. Jan. 10, 2013;493(7431):231-5.
Kwan et al., "The Tol2kit: A Multisite Gateway-Based Construction Kit for Tol2 Transposon Transgenesis Constructs" Dev Dyn. Nov. 2007;236(11):3088-99.
Langenau et al., "Co-injection Strategies to Modify Radiation Sensitivity and Tumor Initiation in Transgenic Zebrafish" Oncogene. Jul. 10, 2008;27(30):4242-8.
Lee et al., "EBV Noncoding RNA Binds Nascent RNA to Drive Host PAX5 to Viral DNA" Cell. Feb. 12, 2015;160(4):607-618.
Lennox et al., "Cellular Localization of Long Non-Coding RNAs Affects Silencing by RNAi More Than by Antisense Oligonucleotides" Nucleic Acids Res. Jan. 29, 2016;44(2):863-77.
Li et al., "A combined analysis of genome-wide association studies in breast cancer." Breast Cancer Res Treat. Apr. 2011;126(3):717-27.
Lieschke et al., "Animal Models of Human Disease: Zebrafish Swim Into View" Nat Rev Genet. May 2007;8(5):353-67.
Livingstone "IGF2 and Cancer" Endocr Relat Cancer. Oct. 24, 2013;20(6):R321-39.
Luke et al., "TERRA: Telomeric Repeat-Containing RNA" EMBO J. Sep. 2, 2009;28(17):2503-10.
Maattanen et al., "European randomized study of prostate cancer screening: first-year results of the Finnish trial." Br J Cancer. Mar. 1999;79(7-8):1210-4.
Malik et al., "The lncRNA PCAT29 Inhibits Oncogenic Phenotypes in Prostate Cancer" Mol Cancer Res. Aug. 2014;12(8):1081-7.
Mattick et al. "Non-coding RNA" Hum Mol Genet. Apr. 15, 2006;15 Spec No. 1:R17-29.
Mehra "A Novel RNA in Situ Hybridization Assay for the Long Noncoding RNA SChLAP1 Predicts Poor Clinical Outcome After Radical Prostatectomy in Clinically Localized Prostate Cancer" Neoplasia. Dec. 2014;16(12):1121-7.
Mehra "Discovery and Characterization of PRCAT47: A Novel Prostate Lineage and Cancer-Specific Long Noncoding RNA" annual reward of W81XWH-16-1-0314, Jul. 1, 2017,p. 1-27, retrieved May 27, 2019 from the internet: https://apps.dtic.mil/dtic/tr/fulltext/u2/1050260.pdf.
Mele et al., "Human Genomics. The Human Transcriptome Across Tissues and Individuals" Science. May 8, 2015;348(6235):660-5.
Michailidou et al., "Large-scale genotyping identifies 41 new loci associated with breast cancer risk." Nat Genet. Apr. 2013;45(4):353-61.
Necsulea et al., "The evolution of lncRNA repertoires and expression patterns in tetrapods." Nature. Jan. 30, 2014;505(7485):635-40.
Nelson et al., "A Peptide Encoded by a Transcript Annotated as Long Noncoding RNA Enhances SERCA Activity in Muscle" Science. Jan. 15, 2016;351(6270):271-5.
Nielsen et al., "A Family of Insulin-Like Growth Factor II mRNA-binding Proteins Represses Translation in Late Development" Mol Cell Biol. Feb. 1999;19(2):1262-70.
Niknafs et al., "The lncRNA Landscape of Breast Cancer Reveals a Role for DSCAM-AS1 in Breast Cancer Progression" Nat Commun. Sep. 26, 2016;7:12791. 13 pages.
Pauli et al., "Toddler: An Embryonic Signal That Promotes Cell Movement via Apelin Receptors" Science. Feb. 14, 2014;343(6172):1248636.
Petrylak et al., "Docetaxel and Estramustine Compared With Mitoxantrone and Prednisone for Advanced Refractory Prostate Cancer" N Engl J Med. Oct. 7, 2004;351(15):1513-20.
Pickard, M.R. et al. "Long non-coding RNA GAS5 regulates apoptosis in prostate cancer cell lines" Biochimica et Biophysica Acta Molecular Basis of Disease, vol. 1832, No. 10, Oct. 1, 2013, pp. 1613-1623.
Prensner et al. "The Hong noncoding RNA SChLAP1 promotes aggressive prostate cancer and antagonizes the SWI/SNF complex" Nature Genetics, vol. 45, No. 11, Sep. 29, 2013, pp. 1392-1398.
Prensner et al., "The emergence of lncRNAs in cancer biology" Cancer Discov. Oct. 2011; 1(5): 391-407.
Prensner et al., "Transcriptome sequencing across a prostate cancer cohort identifies PCAT-1, an unannotated lincRNA implicated in disease progression." Nat Biotechnol. Jul. 31, 2011;29(8):742-9.
Qin et al., "Systematic Identification of Long Non-Coding RNAs With Cancer-Testis Expression Patterns in 14 Cancer Types" Oncotarget. Oct. 19, 2017;8(55):94769-94779.
Rhodes et al., "Oncomine 3.0: genes, pathways, and networks in a collection of 18,000 cancer gene expression profiles." Neoplasia. Feb. 2007;9(2):166-80.

(56) References Cited

OTHER PUBLICATIONS

Rinn et al., "Functional Demarcation of Active and Silent Chromatin Domains in Human HOX Loci by Noncoding RNAs" Cell. Jun. 29, 2007;129(7):1311-23.
Rinn et al., "Genome Regulation by Long Noncoding RNAs" Annu Rev Biochem. 2012;81:145-66.
Ruijter et al., "Molecular genetics and epidemiology of prostate carcinoma." Endocr Rev. Feb. 1999;20(1):22-45.
Sahu et al., "Long Noncoding RNAs in Cancer: From Function to Translation" Trends Cancer. Oct. 1, 2015;1(2):93-109.
Salmena et al., "A ceRNA Hypothesis: The Rosetta Stone of a Hidden RNA Language?" Cell. Aug. 5, 2011;146(3):353-8.
Sanchez-Rivera et al., "Applications of the CRISPR-Cas9 System in Cancer Biology" Nat Rev Cancer. Jul. 2015;15(7):387-95.
Sauvageau et al., "Multiple Knockout Mouse Models Reveal lincRNAs Are Required for Life and Brain Development" Elife. Dec. 31, 2013;2:e01749.
Schroder et al., "Evaluation of the digital rectal examination as a screening test for prostate cancer. Rotterdam section of the European Randomized Study of Screening for Prostate Cancer." J Natl Cancer Inst. Dec. 2, 1998;90(23):1817-23.
Shukla et al., "Identification and Validation of PCAT14 as Prognostic Biomarker in Prostate Cancer" Neoplasia. Aug. 2016;18(8):489-99.
Simpson et al. "Cancer/testis Antigens, Gametogenesis and Cancer" Nat Rev Cancer. Aug. 2005;5(8):615-25.
St. Laurent et al., "The Landscape of Long Noncoding RNA Classification" Trends Genet. May 2015;31(5):239-51.
Stacey et al., "Common variants on chromosomes 2q35 and 16q12 confer susceptibility to estrogen receptor-positive breast cancer." Nat Genet. Jul. 2007;39(7):865-9.
Steijger et al., "Assessment of transcript reconstruction methods for RNA-seq." Nat Methods. Dec. 2013;10(12):1177-84.
Subramanian et al., "Gene Set Enrichment Analysis: A Knowledge-Based Approach for Interpreting Genome-Wide Expression Profiles" Proc Natl Acad Sci U S A. Oct. 25, 2005;102(43):15545-50.
Takayama et al., "Androgen-responsive Long Noncoding RNA CTBP1-AS Promotes Prostate Cancer" EMBO J. Jun. 12, 2013;32(12):1665-80.
Tapparel et al., "The TPTE Gene Family: Cellular Expression, Subcellular Localization and Alternative Splicing" Gene. Dec. 24, 2003;323:189-99.
Taylor et al., "Integrative genomic profiling of human prostate cancer." Cancer Cell. Jul. 13, 2010;18(1):11-22.
Thomas et al., "multistage genome-wide association study in breast cancer identifies two new risk alleles at 1p11.2 and 14q24.1 (RAD51L1)." Nat Genet. May 2009;41(5):579-84.
Turnbull et al., "Genome-wide association study identifies five new breast cancer susceptibility loci." Nat Genet. Jun. 2010;42(6):504-7.
Ulitsky et al., "Conserved Function of lincRNAs in Vertebrate Embryonic Development Despite Rapid Sequence Evolution" Cell. Dec. 23, 2011;147(7):1537-50.
Ulitsky et al., "lincRNAs: Genomics, Evolution, and Mechanisms" Cell. Jul. 3, 2013;154(1):26-46.
Wang et al., "A Long Noncoding RNA Maintains Active Chromatin to Coordinate Homeotic Gene Expression" Nature. Apr. 7, 2011;472(7341):120-4.
Wang et al., "CPAT: Coding-Potential Assessment Tool using an alignment-free logistic regression model." Nucleic Acids Res. Apr. 1, 2013;41(6):e74.
Wang et al., "Molecular Mechanisms of Long Noncoding RNAs" Mol Cell. Sep. 16, 2011;43(6):904-14.
Weidensdorfer et al., "Control of C-Myc mRNA Stability by IGF2BP1-associated Cytoplasmic RNPs" RNA. Jan. 2009;15(1):104-15.
Welter et al., "The NHGRI GWAS Catalog, a curated resource of SNP-trait associations." Nucleic Acids Res. Jan. 2014;42(Database issue):D1001-6.
Winnepenninckx et al. "Gene Expression Profiling of Primary Cutaneous Melanoma and Clinical Outcome" J Natl Cancer Inst. Apr. 5, 2006;98(7):472-82.
Wright et al., "CopraRNA and IntaRNA: Predicting Small RNA Targets, Networks and Interaction Domains" Nucleic Acids Res. Jul. 2014;42(Web Server issue):W119-23.
Wutz et al., "Chromosomal Silencing and Localization Are Mediated by Different Domains of Xist RNA" Nat Genet. Feb. 2002;30(2):167-74.
Yu et al., "Gene expression alterations in prostate cancer predicting tumor aggression and preceding development of malignancy." J Clin Oncol. Jul. 15, 2004;22(14):2790-9.
Zhang et al., "Analysis of the Androgen Receptor-Regulated lncRNA Landscape Identifies a Role for ARLNC1 in Prostate Cancer Progression" Nat Genet. Jun. 2018;50(6):814-824.
Zhou Du et al. "Integrative genomic analyses reveal clinically relevant long noncoding RNAs in human cancer" Nature Structural & Molecular Biology, vol. 20, No. 7, Jun. 2, 2013, pp. 908-913.

\* cited by examiner

FIG. 3K
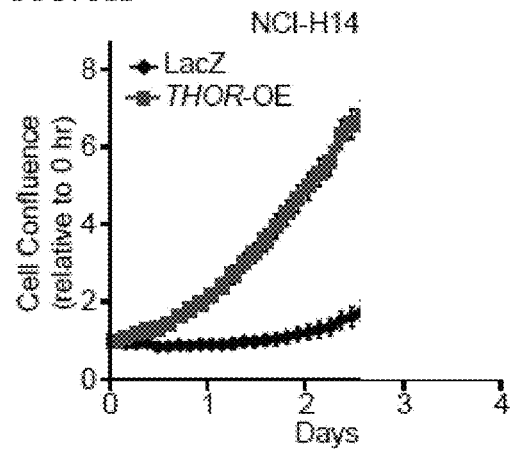
FIG. 3L
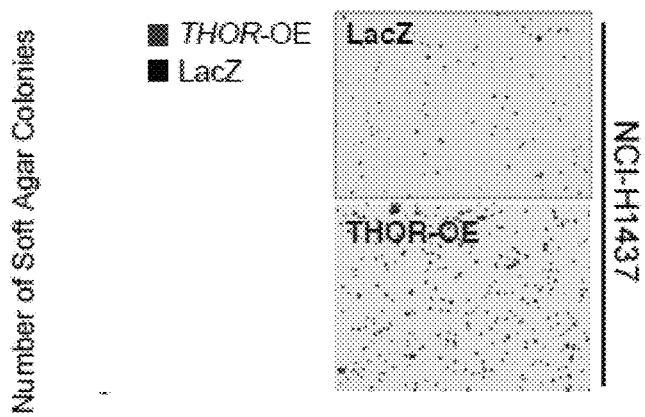
FIG. 3M
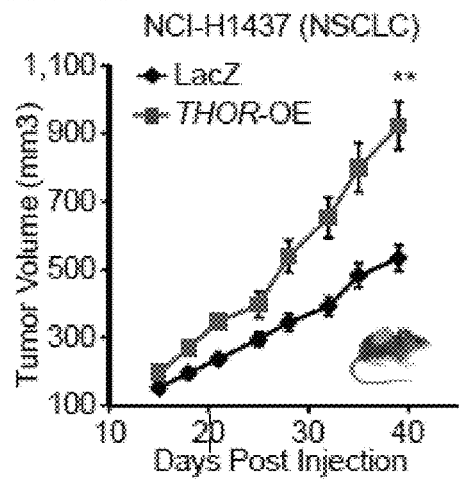
FIG. 4A
| | | | | | | | | |
|---|---|---|---|---|---|---|---|---|
| IGF2BP1 | ●●●● | U2AF2 | ● | RBMX | ● | PABPC4 | ● |
| IGF2BP3 | ●●●● | ACTB | ● | RL19 | ● | SRSF1 | ● |
| STAU1 | ●● | ACTG | ● | DHX9 | ● | dicer | ● |
| STAU2 | ●● | ILF2 | ● | IGF2BP2 | ● | npm1 | ● |
| TARBP2 | ●● | ILF3 | ● | DHL30 | ● | hnrnph | ● |
| PCBP2 | ●● | ZN364 | ● | YBX1 | ● | pcbp3 | ● |
| SUGP2 | ● | HNRNPL | ● | YBX2 | ● | rpf1 | ● |
| DSRAD | ● | MATR3 | ● | YBX3 | ● | | |

FIG. 6A
FIG. 6B
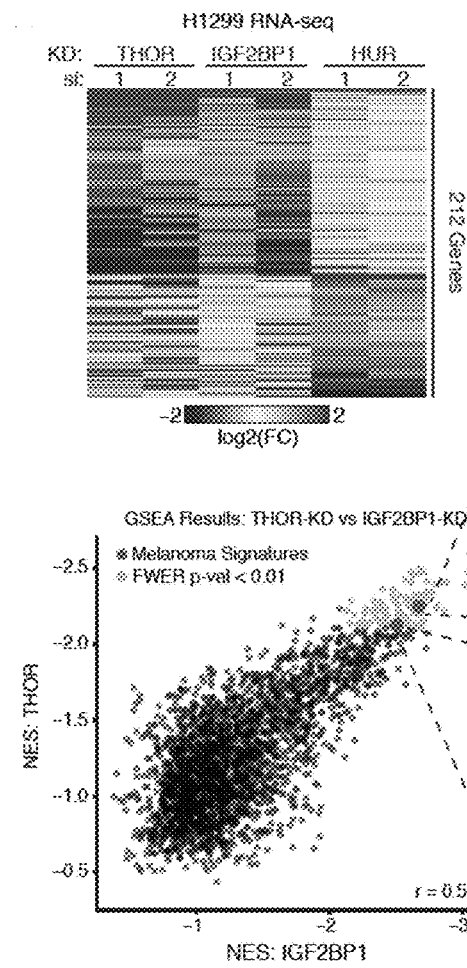
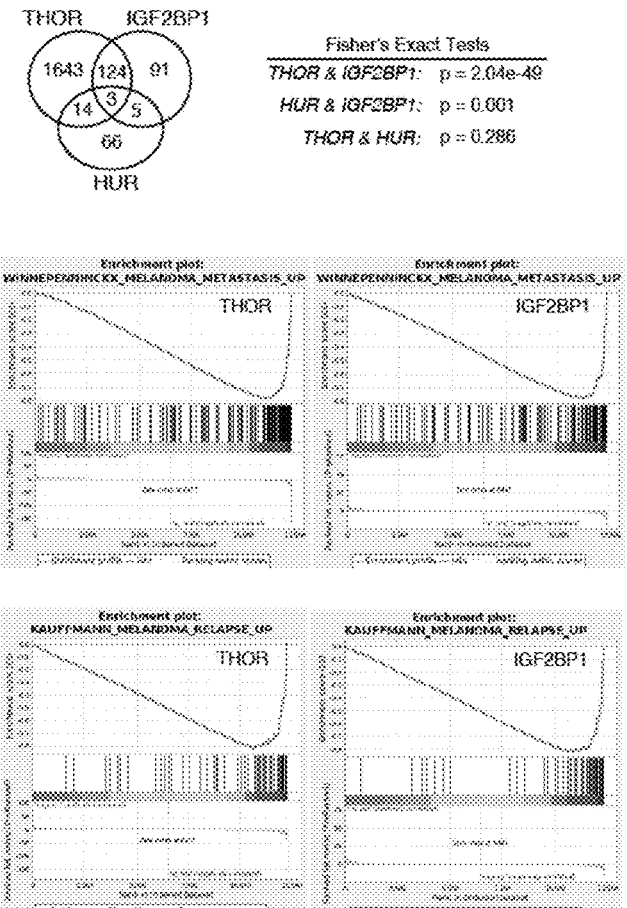
FIG. 6C

FIG. 9A
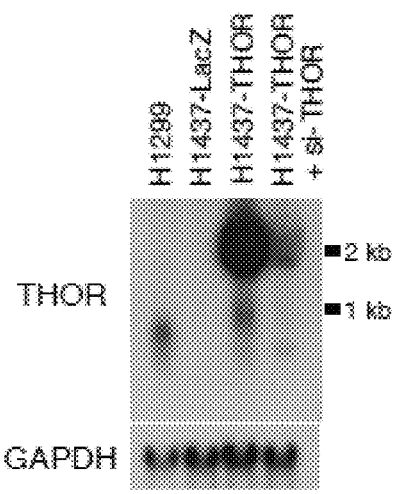
FIG. 9B
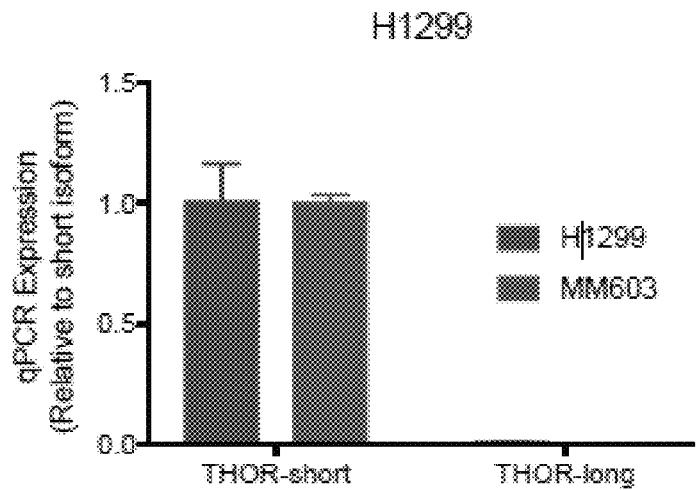
FIG. 9C
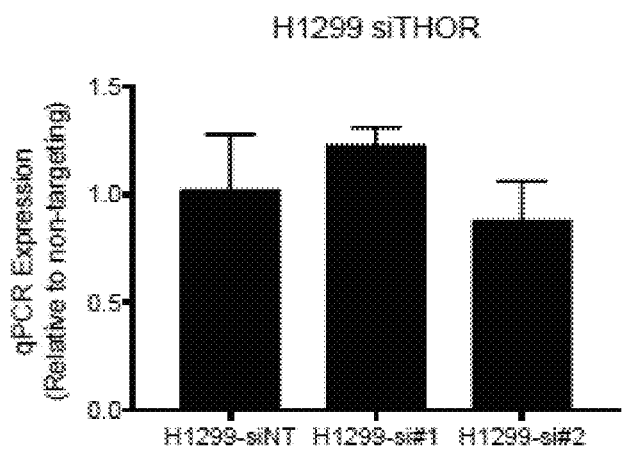
FIG. 9D
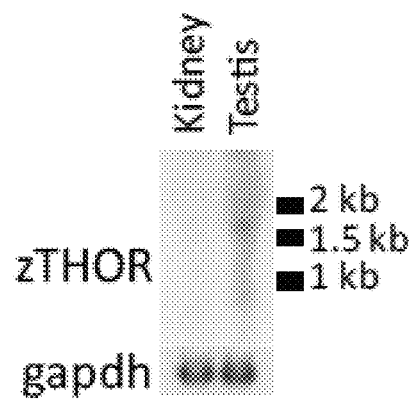
FIG. 9E
| | Class | RNA size | CPAT Coding Probability |
|---|---|---|---|
| THOR | Non-coding | 580 | 0.0022 |
| SCHLAP1 | Non-coding | 1436 | 0.0780 |
| NRAS | protein-coding | 570 | 0.9470 |
| TP53 | protein-coding | 2591 | 0.9999 |

FIG. 9F
|  | PhyloCSF Score | CPC Score |
|---|---|---|
| THOR | -264.06 | -0.955 |
| MYC | 3254.36 | 2.305 |
FIG. 9G
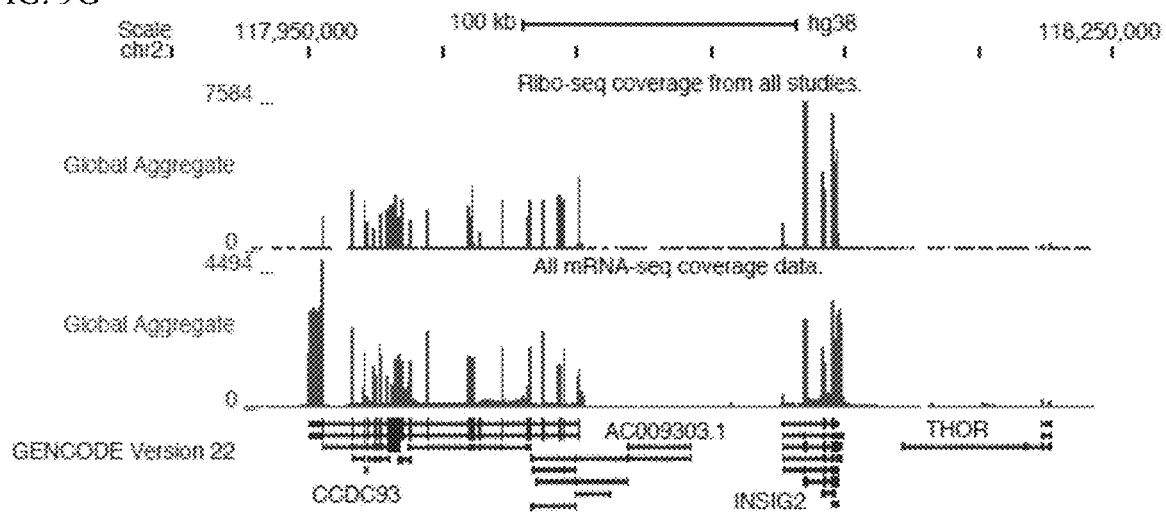
FIG. 9H
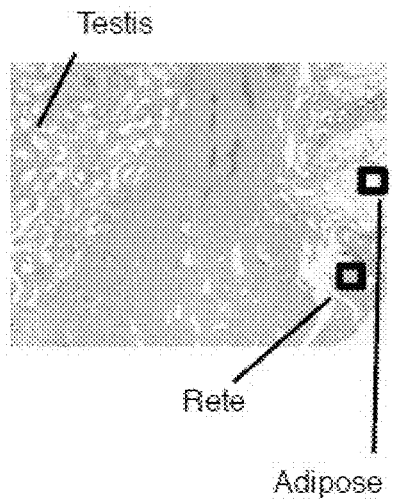
FIG. 9I
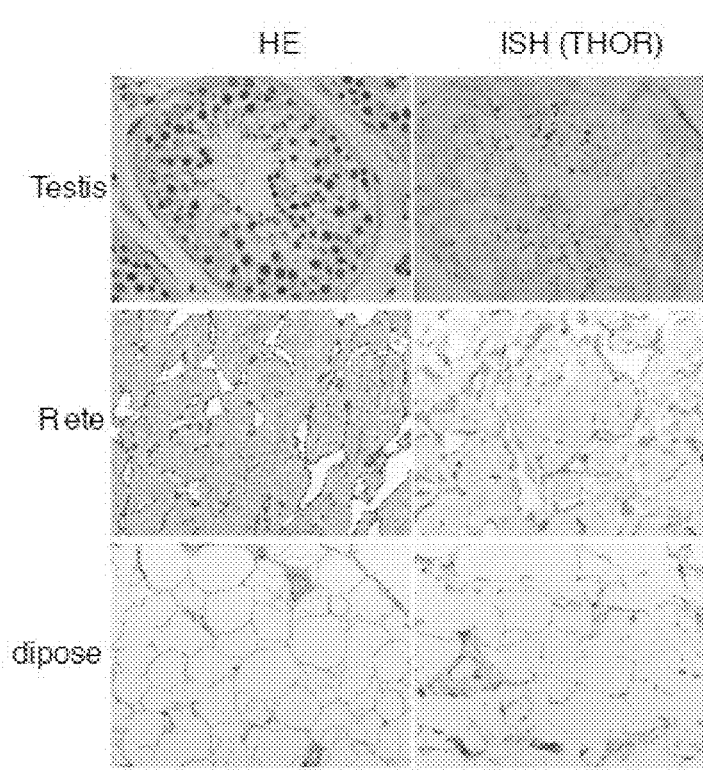

FIG. 10A
FIG. 10B
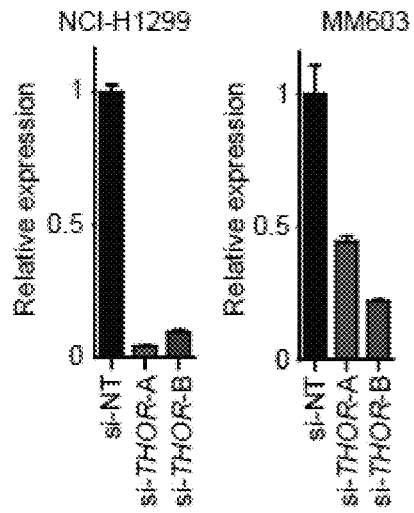
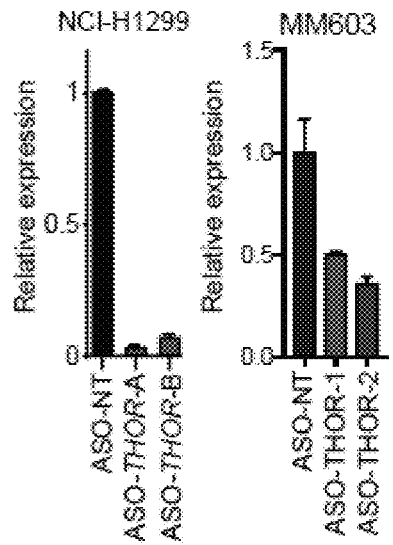
FIG. 10C
FIG. 10D
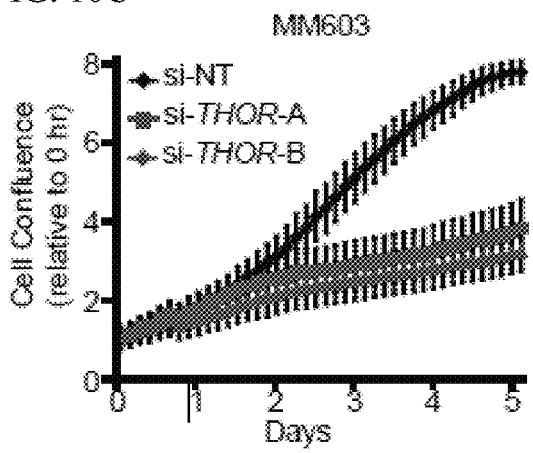
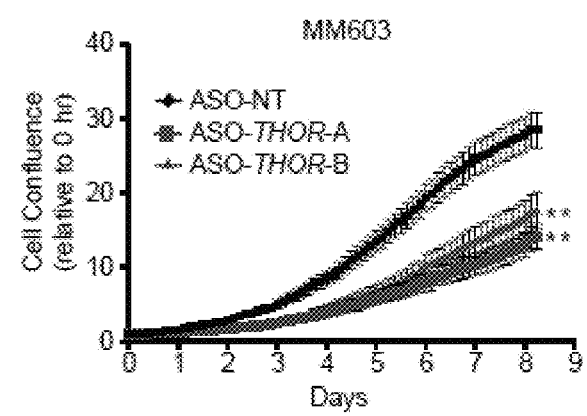
FIG. 10E
FIG. 10F
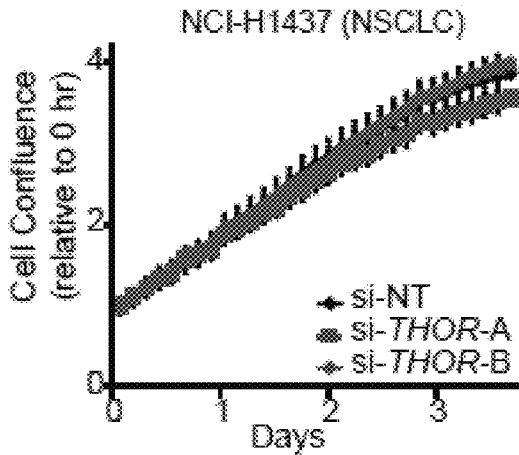
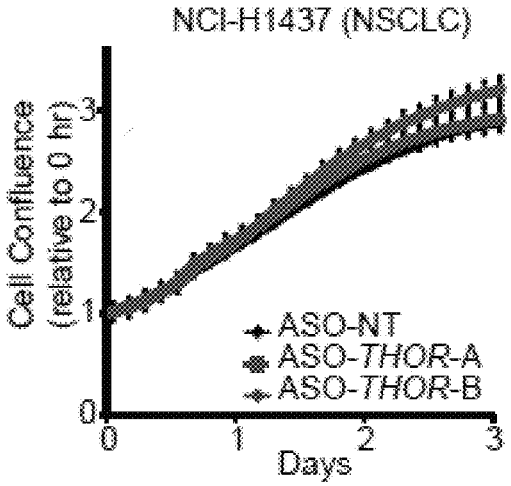

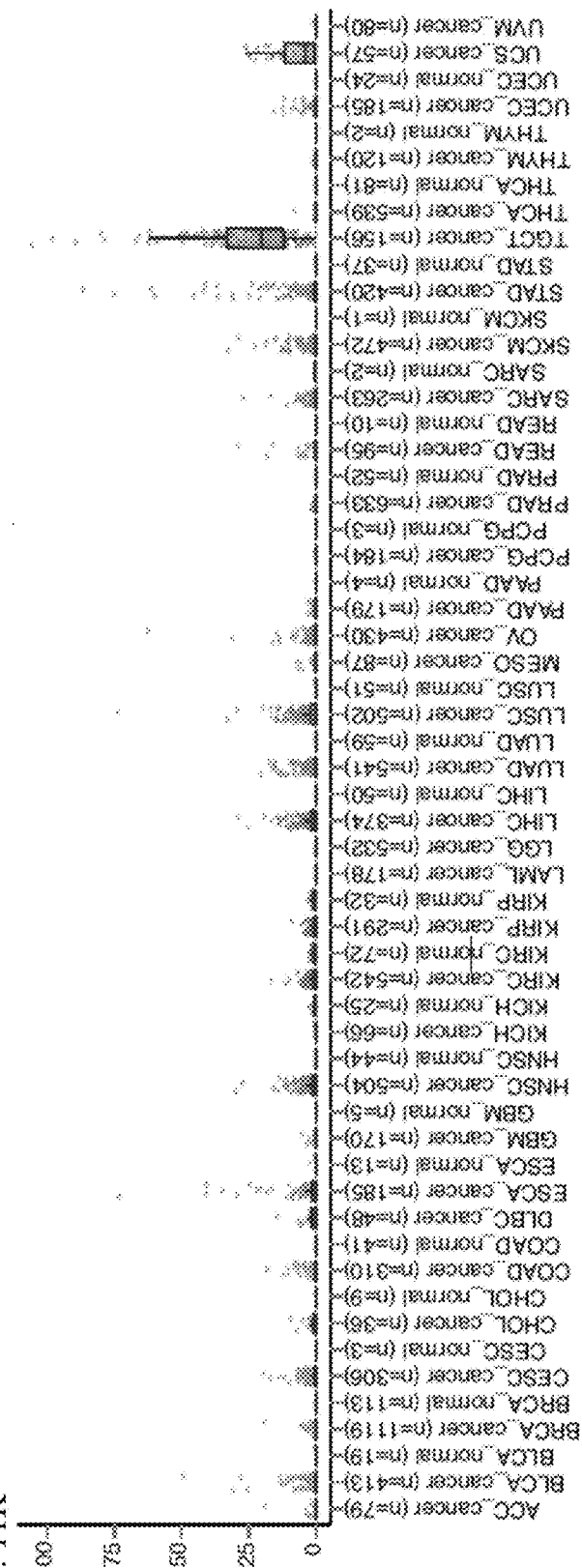
FIG. 11K
FIG. 11M
FIG. 11L
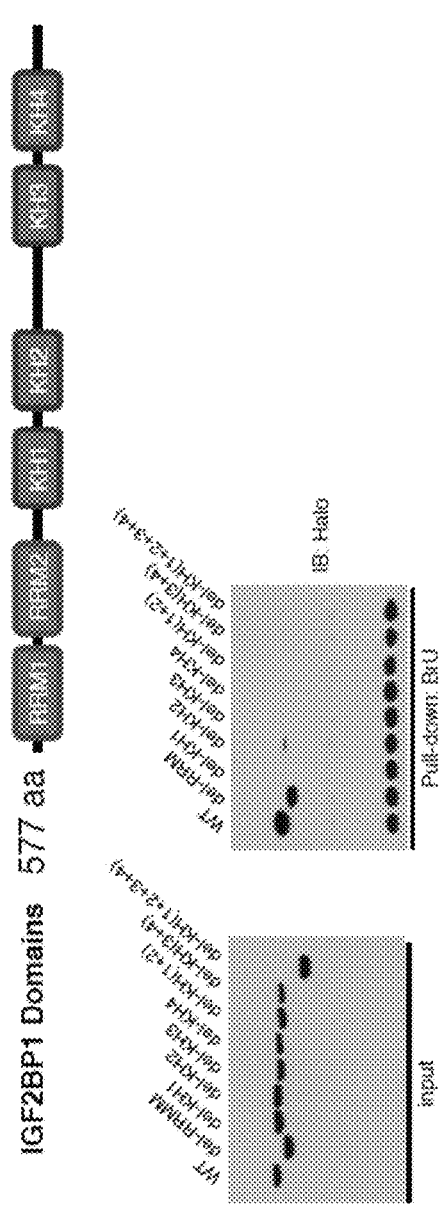
FIG. 11N

FIG. 14H
FIG. 14I
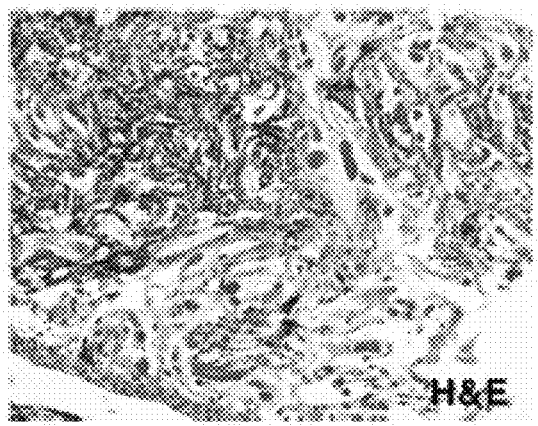
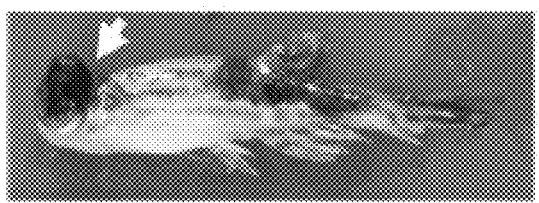
FIG. 14J
FIG. 14K
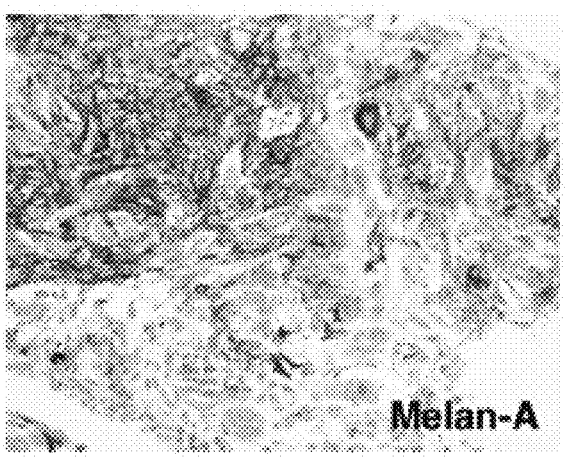
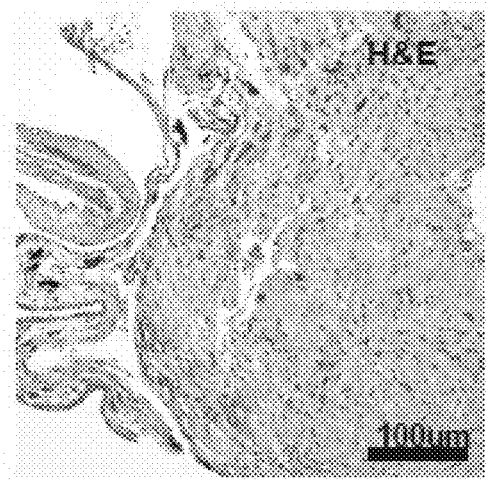
FIG. 14L
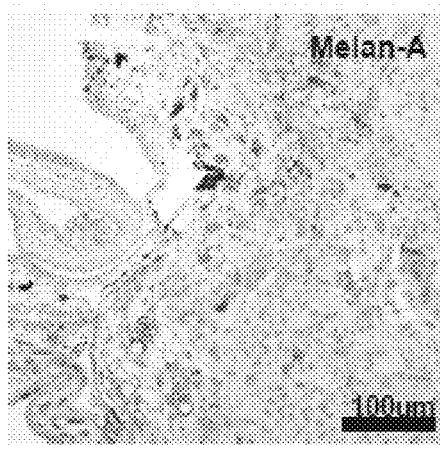

COMPOSITIONS AND METHODS FOR TREATING CANCER

CROSS REFERENCE TO RELATED APPLICATION

This application claims priority to and the benefit of U.S. Provisional Application No. 62/590,072, filed Nov. 22, 2017, which is hereby incorporated by reference in its entirety.

STATEMENT REGARDING FEDERALLY SPONSORED RESEARCH OR DEVELOPMENT

This application was supported by Grant Nos. U01CA113913 and R01CA154365 awarded by the National Institutes of Health. The government has certain rights in the invention.

FIELD

Provided herein are compositions and methods for treating cancer. In particular, provided herein are compositions, methods, and uses of inhibitors of Testis-associated Highly-conserved Oncogenic long non-coding RNA (THOR) for treating cancer.

BACKGROUND

Lung cancer remains the leading cause of cancer death in industrialized countries. About 75 percent of lung cancer cases are categorized as non-small cell lung cancer (e.g., adenocarcinomas), and the other 25 percent are small cell lung cancer. Lung cancers are characterized in to several stages, based on the spread of the disease. In stage I cancer, the tumor is only in the lung and surrounded by normal tissue. In stage II cancer, cancer has spread to nearby lymph nodes. In stage III, cancer has spread to the chest wall or diaphragm near the lung, or to the lymph nodes in the mediastinum (the area that separates the two lungs), or to the lymph nodes on the other side of the chest or in the neck. This stage is divided into IIIA, which can usually be operated on, and stage IIIB, which usually cannot withstand surgery. In stage IV, the cancer has spread to other parts of the body.

Most patients with non-small cell lung cancer (NSCLC) present with advanced stage disease, and despite recent advances in multi-modality therapy, the overall ten-year survival rate remains dismal at 8-10% (Fry et al., Cancer 86:1867 [1999]). However, a significant minority of patients, approximately 25-30%, with NSCLC have pathological stage I disease and are usually treated with surgery alone. While it is known that 35-50% of patients with stage I disease will relapse within five years (Williams et al., Thorac. Cardiovasc. Surg. 82:70 [1981]; Pairolero et al., Ann, Thorac. Surg. 38:331 [1984]), it is not currently possible to identify which specific patients are at high risk of relapse.

Adenocarcinoma is currently the predominant histologic subtype of NSCLC (Fry et al., supra; Kaisermann et al., Brazil Oncol. Rep. 8:189 [2001]; Roggli et al., Hum. Pathol. 16:569 [1985]). While histopathological assessment of primary lung carcinomas can roughly stratify patients, there is still an urgent need to identify those patients who are at high risk for recurrent or metastatic disease by other means. Previous studies have identified a number of preoperative variables that impact survival of patients with NSCLC (Gail et al., Cancer 54:1802 1984]; Takise et al., Cancer 61:2083 [1988]; Ichinose et al., J. Thorac. Cardiovasc. Surg. 106:90 [1993]; Harpole et al., Cancer Res. 55:1995]). Tumor size, vascular invasion, poor differentiation, high tumor proliferate index, and several genetic alterations, including K-ras (Rodenhuis et al., N. Engl. J. Med. 317:929 [1987]; Slebos et al., N. Engl. J. Med. 323:561 [1990]) and p53 (Harpole et al., supra; Horio et al., Cancer Res. 53:1 [1993]) mutation, have been reported as prognostic indicators.

Tumor stage is an important predictor of patient survival, however, much variability in outcome is not accounted for by stage alone, as is observed for stage I lung adenocarcinoma which has a 65-70% five-year survival (Williams et al., supra; Pairolero et al., supra). Current therapy for patients with stage I disease usually consists of surgical resection and no additional treatment (Williams et al., supra; Pairolero et al., supra). The identification of a high-risk group among patients with stage I disease would lead to consideration of additional therapeutic intervention for this group, as well as leading to improved survival of these patients.

There is a need for additional diagnostic and treatment options, particularly treatments customized to a patient's tumor.

SUMMARY

Provided herein are compositions and methods for treating cancer. In particular, provided herein are compositions, methods, and uses of inhibitors of THOR for treating cancer.

For example, in some embodiments, provided herein is a method of treating cancer, comprising: administering an agent that blocks the expression or activity of THOR to a subject diagnosed with cancer under conditions such that a sign or symptom of the cancer is reduced. In some embodiments, the agent is a nucleic acid that inhibits expression of THOR. In some embodiments, the nucleic acid is selected from, for example, an siRNA, miRNA, an antisense nucleic acid, or a shRNA. In some embodiments, the cancer is lung cancer or melanoma. In some embodiments, the cancer expresses THOR. In some embodiments, THOR is overexpressed in the cancer relative to the level of expression in non-cancerous cells. In some embodiments, the method further comprises the step of assaying a sample of the cancer for the level of expression of THOR.

Additional embodiments provide a method, comprising: a) assaying a sample from a subject diagnosed with cancer, wherein the sample comprises cancer tissue or cells for the level of expression of THOR; and b) administering an agent that blocks the expression or activity of THOR when expression of THOR is present in the sample.

Further embodiments provide a pharmaceutical composition comprising a) an agent that blocks the expression or activity of THOR; and b) a pharmaceutically acceptable carrier.

Additional embodiments are described herein.

DESCRIPTION OF THE FIGURES

FIG. 3A-M. THOR is expressed in cancers and potentiates tumorigenesis. A, Expression of THOR across a panel of 9,714 TCGA tumors from a myriad of different tissues, and 2,921 normal tissue samples from GTEX and 748 normal tissue samples from the TCGA. Expression represented as log 2 (FPKM+1). B, Expression of THOR in the CCLE cell line panel. Expression represented as log 2 (FPKM+1). C, Expression of THOR in the TCGA lung adenocarcinoma (LUAD) and lung squamous cell carcinoma (LUSC) samples represented alongside each tissue's matched normal samples. THOR is significantly overexpressed in both LUAD and LUSC. D, qRT-PCR validation in an independent tissue cohort reveals THOR upregulation in cancer compared to benign samples both in lung adenocarcinoma (benign, n=13; cancer, n=180), and melanoma tissues (benign, n=2; cancer, n=24). E, Expression levels of THOR in two melanoma (SKCM) and two non-small cell lung cancer (NSCLC) cell lines. Data show mean±S.D. F, Cell proliferation assays for NCI-H1299 cells treated with 2 independent THOR siRNAs. G, Cell proliferation assays for NCI-H1299 cells treated with 2 independent THOR ASOs. Data show mean±S.E. from one of the two independent experiments. H, Anchorage-independent growth of H1299 cells transfected with non-targeting siRNA (si-NT) or two THOR siRNAs (siTHOR-A, siTHOR-B). I, Cell proliferation assay for NCI-H1299 cells with CRISPR-Cas9 mediated THOR knockout vs control in the context of LacZ and THOR overexpression. I, Anchorage-independent growth of H1299 cells transfected with non-targeting siRNA (si-NT) or two THOR siRNAs (siTHOR-A, siTHOR-B). Left, quantification of number of colonies. Right, representative image of surviving colonies and individual colony. J, THOR knockout NCI-H1299 cell line xenografts (N=10) demonstrate decreased tumor growth relative to control samples (N=10). Tumor volumes at each time point by caliper measurement are shown. K, Cell proliferation assay in NCI-H1437 cells stably transfected with THOR overexpression or LacZ control lentivirus. Data show mean±S.E. from one of the two independent experiments. L, Anchorage-independent growth of LacZ or THOR overexpressing H1437 cells. Left, quantification of number of colonies. Right representative images of surviving soft agar colonies. M, THOR overexpressing NCI-H1437 cell line xenografts (N=10) demonstrate increased tumor growth relative to control LacZ samples (N=10). Tumor volumes at each time point by caliper measurement are shown. Asterisk (*) indicates P≤0.001 by a two-tailed Student's t-test. Data show mean±S.E.M. from one of the two independent experiments. For all panels, asterisk (*) indicates P≤0.01, () indicates P≤0.001, (*) indicates P≤0.0001 by a two-tailed Student's t-test.

FIG. 4A-F. Conserved interaction of THOR and IGF2BP1. A, Table reporting the protein binding partners for THOR in four different experimental conditions of RNA pull-down analysis: zebrafish THOR added to human H1299 cell lysate (green), human THOR added to human H1299 cell lysate (blue), zebrafish THOR added to zebrafish embryo lysate (yellow), and human THOR added to zebrafish embryo lysate (red). All proteins bound in any condition are displayed in the table, and each dot represents binding in the respective condition. B, Immunoprecipitation western blotting analysis (IP-WB) for various components of the IGFBP complex which contains IGF2BP1, IGF2BP2, IGF2BP3, STAU1 and YBX1. HuR (ELAV1) was used as a negative control. C, qRT-PCR following RIP of IGF2BP1, IGF2BP2, IGF2BP3, STAU1, YBX1, HUR, and IgG in H1299 cells. Data show mean±S.D. from one of the two independent experiments. D, In vitro RNA-protein binding assay. In vitro transcribed THOR added to purified myc-tagged proteins. THOR qRT-PCR was then performed following anti-myc pull-down. Asterisk (*) indicates P≤0.01 by a two-tailed Student's t-test. Data show mean±S.D. from one of the two independent experiments. E, Schematic representation of human THOR, antisense-THOR (AS), and various deletion constructs generated to interrogate IGF2BP1 binding (left). Fragment sizes confirmed by PCR (right, top), and binding of each fragment to IGF2BP1 determined via pulldown of BRU-labelled RNA fragments (right, bottom) in H1299 cells. F, Schematic representation of zebrafish THOR constructs generated to study IGF2BP1 binding. Fragment sizes confirmed by PCR (right, top), and binding of each fragment to zebrafish igf2bp1 determined via pulldown of BRU-labelled RNA fragments (right, bottom) in 16 hpf embryos.

FIG. 6A-C. Shared transcriptional regulation by THOR and IGF2BP1. A. Heatmap depicting the expression of the genes significantly differentially expressed (DESeq FDR<0.05) in knockdown of THOR and IGF2BP1 in H1299 cells in addition to those genes with significant differential expression in HUR knockdown. Expression depicted as the log 2(fold-change) for each siRNA compared to the non-targeting siRNA control. B. Venn diagram depiction of the overlap for the significant differentially expressed genes in THOR, IGF2BP1, and HUR knockdown. Fisher's exact statistics shown on the right. C. Scatterplot depicting the GSEA performance for MSigDBv5.0 gene signatures with NES<0 for both THOR and IGF2BP1 knockdown (left). Signatures significant upon knockdown of both genes (FWER p-value <0.01) depicted in gold. Two melanoma gene signatures depicted in blue. Pearson correlation coefficient shown in bottom right of scatterpot. GSEA plots for two significant melanoma signatures depicted for knockdown of THOR and IGF2BP1 (right).

FIG. 9A-K. A, Northern blot of endogenous THOR in H1299 cells, and of H1437 cells expressing LacZ control, THOR, and THOR with the addition of siRNA targeting THOR. Blot of gapdh provided as a control. B, Bar plot depicting the qPCR expression of the long vs short THOR isoform. C, qPCR expression of the long THOR isoform following addition of siRNA. C, Northern blot of THOR in zebrafish kidney and testis. Blot of GAPDH provided as a control. D, 5' RACE for the THOR transcripts expressed by the lentiviral system. PCR agarose gel (left) confirms single band used in Sanger sequencing (right). F, 3' RACE for the THOR transcripts expressed by the lentiviral system. PCR agarose gel (left) shows two bands utilized in Sanger sequencing (right). G, Coding probability scores for the transcripts were assessed by Coding Potential Assessment Tool (CPAT). NRAS and TP53 used as positive control, and SCHLAP1 as a negative control. H, Coding probability scores for the PhyloCSF and CPC tools for THOR and MYC. Values less than 0 suggest a lack of coding potential. I, Genome browser depiction of the THOR locus with aggregate ribosomal profiling track (red), aggregate poly-A RNA-seq track (green) and GENCODE v22 genome annotation obtained from the GWIPS-viz ribo-seq genome browser. J, H&E image of the testis and surrounding tissue architecture. K, H&E (left) and THOR ISH (right) for the human testis, rete, and adipose.

FIG. 14A-L. THOR genetic model in zebrafish exhibits melanoma phenotype and fertility phenotype. A, Schematic representation of human and zebrafish THOR transcript structure and the guide RNA (gRNA) design used to delete the conserved transcript region of zebrafish THOR via CRISPR/Cas9 genome editing (top). Validation of THOR knockout at both DNA (genotyping) and RNA (qRT-PCR) level (bottom). Data show mean±S.D. B, Kaplan-Meier curve of tumor free period for p53−/− zebrafish (solid lines) and p53 wildtype zebrafish (dotted lines) co-injected with either mitfa promoter driven NRAS 61K+mitfa promoter driven human THOR (red) or mitfa promoter driven NRAS 61K+mCherry (blue). C-D, Cell selection is visualized in a "Hoechst Blue"/"Hoechst Red" contour plot, in which the density of the cells is displayed as contour lines that form circular contours upon high cell density. Contour plots shown for sorted zebrafish spermatocytes from (C) wildtype zebrafish and (D) THOR knockout zebrafish. E, GSEA results shown for all 5 MSigDB signatures related to meiosis for gene expression changes following siRNA mediated THOR knockdown determined by RNA-seq. Genes ranked by −log(pval)*(Fold Change). F, Representative GSEA plot for the REACTOME_MEIOTIC_SYNAPSE gene signature. G, Volcano plot for gene expression changes following THOR knockdown determined via DESeq. Meiotic histone genes in the MEIOTIC_SYNAPSE gene signature shown in blue. H, Representative image of zebrafish with melanoma. I-J, Immunohistochemistry for melanoma in p53 wildtype background with endogenous THOR. K-L, Immunohistochemistry for melanoma in p53 knockout background zebrafish with exogenous h-THOR. I and K, H and E staining (100×) of melanoma. J and L, Immunohistochemistry staining (100×) for Melan-A of melanoma.

DEFINITIONS

Figure 1A:
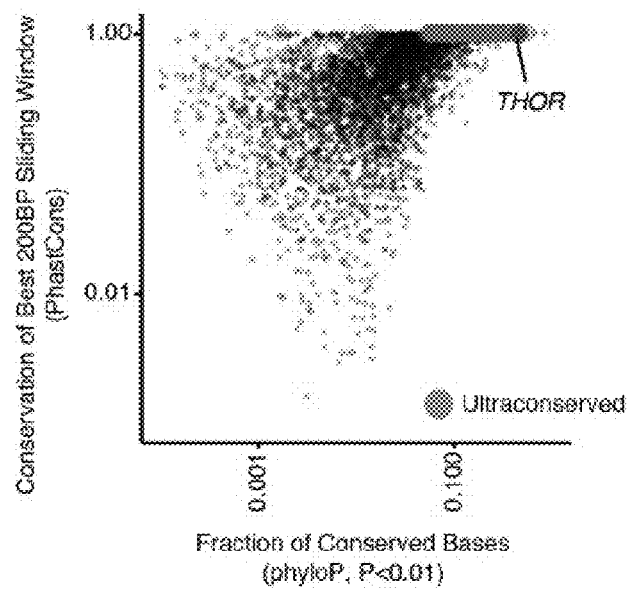
FIG. 1A-D. THOR is a conserved testis specific lncRNA. A, Scatter plot depicting the distribution of basewise transcript conservation levels (x axis) and the average conservation for the best 200 bp window (y axis) for all intergenic transcripts expressed at 1 FPKM or more in the top 1% of TCGA samples. Full transcript conservation levels were measured using the fraction of conserved bases (PhyloP $p<0.01$). Sliding window conservation levels were measured using the average PhastCons score across 200 bp regions along the transcript. Green points indicate transcripts with 200 bp windows that meet the criteria for 'ultraconserved' regions (Methods). B, Dual plot depicting the fraction of conserved bases (top, green, FIG. 1A, x axis) and the expression across testes RNA-seq samples (bottom, blue) for all ultraconserved lncRNAs identified in FIG. 1A. C, Expression in FPKM of THOR amongst the GTEX normal tissue RNA-seq dataset, spanning a myriad of different normal tissue types. D, Genome browser depiction of THOR and its conserved analogues in mouse and zebrafish. THOR is annotated in the mouse as gm29359. Multiz alignment of multiple vertebrate species depicted as well as the per base PhastCons conservation score.

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a subject (e.g., a human subject).

As used herein, the term "subject suspected of having cancer" refers to a subject that presents one or more symptoms indicative of cancer. A subject suspected of having cancer may also have one or more risk factors. A subject suspected of having cancer has generally not been tested for cancer. However, a "subject suspected of having cancer" encompasses an individual who has received a preliminary diagnosis but for whom a confirmatory test has not been done or for whom the level or severity of cancer is not known.

As used herein, the term "subject diagnosed with cancer" refers to a subject who has been tested and found to have cancer. As used herein, the term "initial diagnosis" refers to a test result of initial disease that reveals the presence or absence of disease.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., THOR inhibitor described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "toxic" refers to any detrimental or harmful effects on a cell or tissue as compared to the same cell or tissue prior to the administration of the toxicant.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include, but are not limited to, single-stranded and double-stranded compounds, such as, antisense oligonucleotides, siRNAs and shRNAs.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Oligonucleotide" means a polymer of linked nucleosides each of which can be modified or unmodified, independent one from another.

DETAILED DESCRIPTION OF THE DISCLOSURE

Provided herein are compositions and methods for treating cancer. In particular, provided herein are compositions, methods, and uses of inhibitors of THOR for treating cancer.

Over the past decade, there has been a paradigm shift in the understanding of molecular biology sparked by the discovery of non-coding RNAs (ncRNAs) challenging the central dogma of molecular biology (Mattick and Makunin, Hum. Mol. Genet. 15 Spec No, 17-29 2006). It has become apparent that the transcriptome is far more intricate than previously appreciated (Birney et al., Nature 447, 799-816 2007), with various types of non-coding RNAs implicated in key physiological roles in cells (Morris and Mattick, Nat. Rev. Genet. 15, 423-437 2014). Long non-coding RNAs (lncRNAs) have emerged as an abundant and functionally diverse species of ncRNA (Iyer et al Nat Genet *advance on* (2015); Ulitsky and Bartel, Cell 154, 26-46 2013a). Despite their striking prevalence in the transcriptome and countless efforts to interrogate their function, understanding of the function of the vast majority of lncRNAs remains anecdotal, making their classification particularly challenging (St. Laurent et al., Trends Genet. 31, 239-251 2015). Novel classes of lncRNAs continue to be identified with categorization criteria including their degree of conservation (Ulitsky et al., Cell 147, 1537-1550 2011), association with various DNA elements (Kim et al., Nature 465, 182-187 2010; Luke and Lingner, EMBO J. 28, 2503-2510 2009), ability to bind miRNAs (Salmena et al., Cell 146, 353-358 2011), regulation of chromatin remodeling (Gupta et al., Nature 464, 1071-1076 2010; Prensner et al., Nat. Genet. 45, 1392-1398 2013; Wang et al., Nature 472, 120-124 2011), induction of aneuploidy (Lee et al., Cell 2015), influence on RNA stability machinery (Kretz et al., Nature 493, 231-235 2013), and their potential to produce small peptides (Nelson et al., Science 351, 271-275 2016; Pauli et al., Science 343, 1248636 2014).

Recently, it was discovered that the human genome possesses the potential to transcribe tens of thousands of lncRNAs (Iyer et al., supra). With the overwhelmingly large number of potentially functional elements to investigate, features such as degree of evolutionary conservation and expression pattern are logical criteria that can be employed to discover functionally important lncRNAs in cells. Although the general level of conservation of lncRNAs has been contentious (Cabili et al., Genes Dev. 25, 1915-1927 2011; Iyer et al., supra), there is a clear subclass of lncRNAs that are highly conserved, many of which possess "ultra-conserved" regions (i.e., at least 200 base-pairs (bps) of nearly perfect vertebrate conservation) (Calin et al., Cancer Cell 12, 215-229 2007; Hudson et al., Mol. Cancer 12, 13 2013; Ulitsky et al., Cell 147, 1537-1550 2011). While conservation is a trait highly suggestive of functional relevance in cells, it also permits the characterization and mechanistic investigation of lncRNAs in model organisms (Sauvageau et al., eLife 2013, 1-24 2013; Ulitsky et al., 2011; supra), a particularly exciting avenue given the recent popularization of genome editing techniques (Cong et al., Science 339, 819-823 2013).

In searching for highly conserved lncRNAs with intriguing expression patterns, experiments described herein defined a novel class of lncRNA, with normal tissue expression limited to the testis and widespread expression in multiple cancer types. This cancer/testis expression pattern is characteristic of cancer/testis antigens. While many cancer-associated lncRNAs have been identified (Prensner and Chinnaiyan, Cancer Discov. 1, 391-407 2011; Sahu et al., Trends Cancer 1, 93-109 2016), none previously characterized have exhibited cancer/testis expression. Described herein is the first cancer/testis lncRNA, THOR (Testis-associated Highly-conserved Oncogenic long non-coding RNA), and its role in oncogenesis and testis physiology, identifying an evolutionarily conserved functional interaction with IGF2 mRNA-binding proteins (IGF2BPs).

Accordingly, provided herein are compositions and methods for treating cancer by inhibiting the expression and/or function of THOR.

I. Inhibitors

In some embodiments, the THOR inhibitor is selected from, for example, a nucleic acid (e.g., siRNA, shRNA, miRNA or an antisense nucleic acid), a small molecule, a peptide, or an antibody.

a) Nucleic Acids

In some embodiments, the THOR inhibitor is a nucleic acid. Exemplary nucleic acids suitable for inhibiting THOR (e.g., by preventing expression of THOR) include, but are not limited to, antisense nucleic acids and RNAi. In some embodiments, nucleic acid therapies are complementary to and hybridize to at least a portion (e.g., at least 5, 8, 10, 11, 12, 13, 14, 15, 16, 17, 18, 19, or 20 nucleotides) of THOR.

In some embodiments, compositions comprising oligomeric antisense compounds, particularly oligonucleotides are used to modulate the function of nucleic acid molecules encoding THOR, ultimately modulating the amount of THOR expressed. This is accomplished by providing antisense compounds that specifically hybridize with one or more THOR nucleic acids. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is decreasing the amount of THOR proteins in the T-cell.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which include, without limitation, siRNA, ssRNA and microRNA mechanisms; and occupancy based mechanisms. Certain antisense compounds may act through more than one such mechanism and/or through additional mechanisms.

In certain embodiments, antisense compounds, including those particularly suitable for ssRNA comprise one or more type of modified sugar moieties and/or naturally occurring sugar moieties. In certain embodiments, antisense compounds, including those particularly suited for use as ssRNA comprise modified internucleoside linkages. Exemplary modifications are described, for example, in Geary et al., Adv Drug Deliv Rev. 2015 Jun. 29; 87:46-51; herein incorporated by reference in its entirety.

In some embodiments, nucleic acids are RNAi nucleic acids. "RNA interference (RNAi)" is the process of sequence-specific, post-transcriptional gene silencing initiated by a small interfering RNA (siRNA), shRNA, or microRNA (miRNA). During RNAi, the RNA induces degradation of target mRNA with consequent sequence-specific inhibition of gene expression.

In "RNA interference," or "RNAi," a "small interfering RNA" or "short interfering RNA" or "siRNA" or "short hairpin RNA" or "shRNA" molecule, or "miRNA" an RNAi (e.g., single strand, duplex, or hairpin) of nucleotides is targeted to a nucleic acid sequence of interest, for example, THOR.

An "RNA duplex" refers to the structure formed by the complementary pairing between two regions of a RNA molecule. The RNA using in RNAi is "targeted" to a gene in that the nucleotide sequence of the duplex portion of the RNAi is complementary to a nucleotide sequence of the targeted gene. In certain embodiments, the RNAi is targeted to THOR nucleic acids. In some embodiments, the length of the RNAi is less than 30 base pairs. In some embodiments, the RNA can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the RNAi is 19 to 32 base pairs in length. In certain embodiment, the length of the RNAi is 19 or 21 base pairs in length.

In some embodiments, RNAi comprises a hairpin structure (e.g., shRNA). In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase.

As used herein, Dicer-substrate RNAs (DsiRNAs) are chemically synthesized asymmetric 25-mer/27-mer duplex RNAs that have increased potency in RNA interference compared to traditional RNAi. Traditional 21-mer RNAi molecules are designed to mimic Dicer products and therefore bypass interaction with the enzyme Dicer. Dicer has been recently shown to be a component of RISC and involved with entry of the RNAi into RISC. Dicer-substrate RNAi molecules are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional RNAi molecules. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs.

"Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (e.g., about 35 nucleotides upstream and about 40 nucleotides downstream) arise from restriction enzyme sites within the multiple cloning site of the RNAi. As used herein the term "miRNA" encompasses both the naturally occurring miRNA sequences as well as artificially generated miRNA shuttle vectors.

The RNAi can be encoded by a nucleic acid sequence, and the nucleic acid sequence can also include a promoter (e.g., testes specific promoter; See e.g., Wang et al., DNA Cell Biol. 2008 June; 27(6):307-14; herein incorporate by reference in its entirety). The nucleic acid sequence can also include a polyadenylation signal. In some embodiments, the polyadenylation signal is a synthetic minimal polyad n certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of THOR.

In some embodiments, hybridization occurs between an antisense compound disclosed herein and an THOR nucleic acid. The most common mechanism of hybridization involves hydrogen bonding (e.g., Watson-Crick, Hoogsteen or reversed Hoogsteen hydrogen bonding) between complementary nucleobases of the nucleic acid molecules. Hybridization can occur under varying conditions. Stringent conditions are sequence-dependent and are determined by the nature and composition of the nucleic acid molecules to be hybridized.

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an THOR nucleic acid).

Non-complementary nucleobases between an antisense compound and an THOR nucleic acid may be tolerated provided that the antisense compound remains able to specifically hybridize to a target nucleic acid. Moreover, an antisense compound may hybridize over one or more segments of an THOR nucleic acid such that intervening or adjacent segments are not involved in the hybridization event (e.g., a loop structure, mismatch or hairpin structure). In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an THOR nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a THOR nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an THOR nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an THOR nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. In certain embodiments, the antisense compounds are complementary to at least an 18 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

b) Genetic Therapies

The present disclosure contemplates the use of any genetic manipulation for use in modulating the expression of THOR. Examples of genetic manipulation include, but are not limited to, gene knockout (e.g., removing the THOR gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Exemplary methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present disclosure, vectors are administered into tumors or tissue associated with tumors using direct injection. In other embodiments, administration is via the blood or lymphatic circulation (See e.g., PCT publication 1999/02685 herein incorporated by reference in its entirety). Exemplary dose levels of adenoviral vector are preferably $10^8$ to $10^{11}$ vector particles added to the perfusate.

In some embodiments, CRISPR/Cas9 systems are used to delete or knock out genes or express an inhibitor (e.g., nucleic acid). Clustered regularly interspaced short palindromic repeats (CRISPR) are segments of prokaryotic DNA containing short, repetitive base sequences. These play a key role in a bacterial defence system, and form the basis of a genome editing technology known as CRISPR/Cas9 that allows permanent modification of genes within organisms. In some embodiments, candidate THOR inhibitors are screened for activity (e.g., using the methods described herein or another suitable assay).

c) Compositions

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.
Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

II. Methods of Treating Cancer

Provided herein are methods of treating cancer (e.g., melanoma or lung cancer). In some embodiments, a sample of tumor or cancerous tissue from the subject is first tested for expression of THOR. In some embodiments, treatment is administered to individuals with expression of THOR and/or individuals with levels of expression of THOR greater than the levels in non-cancerous tissue. In some embodiments, samples of tumor or cancer tissue are tested during treatment in order to determine whether or not to continue treatment. In some embodiments, samples are screened for the presence of THOR nucleic acids using any suitable method (e.g., including but not limited to, those described below).

In some embodiments, the compounds and pharmaceutical compositions described herein are administered in combination with one or more additional agents, treatment, or interventions (e.g., agents, treatments, or interventions useful in the treatment of cancer). In some embodiments, THOR inhibitors are co-administered with an anti-cancer agent (e.g., chemotherapeutic). The present disclosure is not limited by type of anti-cancer agent co-administered.

III. Detection of THOR

The presence or level of THOR is detected using any suitable method, including but not limited to, those described herein.

In some embodiments, RNA is detection by Northern blot analysis. Northern blot analysis involves the separation of RNA and hybridization of a complementary labeled probe. In some embodiments, RNA (or corresponding cDNA) is detected by hybridization to a oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In some embodiments, microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays are utilized for measuring cancer marker mRNA levels. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limited to: printing with fine-pointed pins onto glass slides; photolithography using pre-made masks; photolithography using dynamic micromirror devices; ink-jet printing; or, electrochemistry on microelectrode arrays.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876, 978 (each of which is herein incorporated by reference) is utilized.

In some embodiments, the cancer markers are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995, each of which is herein incorporated by reference in its entirety). The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through fluorometric detection means.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097, herein incorporated by reference in its entirety.

By way of non-limiting example, probe binding pairs having interacting labels, such as those disclosed in U.S. Pat. No. 5,928,862 (herein incorporated by reference in its entirety) might be adapted for use in method of embodiments of the present disclosure. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products methods of embodiments of the present disclosure. See, e.g., U.S. Pat. No. 5,814,447 (herein incorporated by reference in its entirety).

In some embodiments, nucleic acid sequencing methods are utilized for detection. In some embodiments, the sequencing is Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, the sequencing is automated sequencing. In some embodiments, the sequenceing is parallel sequencing of partitioned amplicons (PCT Publication No: WO2006084132 to Kevin McKernan et al., herein incorporated by reference in its entirety). In some embodiments, the sequencing is DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

EXPERIMENTAL

The following examples are provided in order to demonstrate and further illustrate certain preferred embodiments and aspects of the present disclosure and are not to be construed as limiting the scope thereof.

Example 1

Experimental Procedures

RNA-Seq Data Processing

TCGA prostate FASTQ files were obtained from the CGhub. Reads were aligned using STAR version 2.4.2 (Dobin et al., Bioinformatics 29, 15-21 2013a) and read abundance was calculated using FeatureCounts version 1.4.6 (Liao et al., Bioinformatics 30, 923-930 2014), providing the MiTranscriptome gene annotation GTF (mitranscriptome.org) (Iyer et al., supra). GTEX (accession: phs000424.v6.p1) and TCGA (accession: phs000178.v8.p7) data were downloaded from dbGAP.

Conservation Analysis

Evolutionary conservation of transcripts was assessed via the fraction of significantly conserved bases ($P \leq 0.01$, phyloP algorithm), and the most conserved 200 nt sliding window (phastCons scores averaged within each window). For contiguous sliding window conservation an average PhastCons probability of 0.9986 was used to identify ultraconserved elements as previously described (Iyer et al., supra).

Coding Potential Assessment

Coding potential for THOR was assessed using the CPAT tool, PhyloCSF, and CPC tool. CPAT and PhyloCSF were run using the command line tools. For PhyloCSF, the multiz alignment for 46 vertebrate species for the sequence conservation of THOR and MYC was obtained using the conservation track from the UCSC genome browser for GRCh38. The CPC tool was run using their online tool (cpc.cbi.pku.edu.cn). Ribosomal profiling data was obtained using the GWIPS-viz genome browser (gwips.ucc.ie).

Cell Lines

All cell lines were obtained from the American Type Culture Collection (Manassas, Va.). Cell lines were maintained using standard media and conditions. Specifically, NCI-H1299 and NCI-H1437 were maintained in RPMI 1640 (Invitrogen) plus 10% fetal bovine serum (FBS) and 1% penicillin-streptomycin. MM603 and SK-MEL-5 were maintained in DMEM (Invitrogen) plus 10% FBS and 1% penicillin-streptomycin. All cell lines were grown at 37° C. in a 5% $CO_2$ cell culture incubator and genotyped for identity at the University of Michigan Sequencing Core and tested routinely for *Mycoplasma* contamination. THOR or control-expressing cell lines were generated by cloning THOR or control into the pLenti6 vector (Invitrogen) using pCR8 non-directional Gateway cloning (Invitrogen) as an initial cloning vector and shuttling to plenti6 using LR clonase II (Invitrogen) according to the manufacturer's instructions. Stably-transfected NCI-H1437 and SK-MEL-5 cells were selected using blasticidin (Invitrogen). All lentiviruses were generated by the University of Michigan Vector Core.

Tissue Samples

The lung cancer and paired non-tumoral lung tissues were obtained from patients undergoing curative cancer surgery during the period from 1991 to 2012 at the University of Michigan Health System. None of the patients included in this study received any preoperative radiation or chemotherapy. All melanoma tissues were procured from the University of Michigan Hospitals Cutaneous Surgery and Oncology Program with appropriate informed consent. Resected specimens were frozen in liquid nitrogen and then stored at −80° C. until use. Total RNA panels from human and mouse normal tissues were purchased from Clontech and Zyagen. Mouse embryos were obtained from the University of Michigan Transgenic Core. Zebrafish tissues and embryos were obtained from AB strain wild type zebrafish.

RNA Isolation and cDNA Synthesis

Total RNA from human and mouse normal tissues were purchased from Clontech and Zyagen. Mouse embryos were obtained from the University of Michigan Transgenic Core. Zebrafish tissues or embryos were obtained from AB strain wild type fish. Nuclear and cytoplasmic fractions were separated using NE-PER Nuclear and Cytoplasmic Extraction Reagents (Thermo) according to the manufacturer's instructions. Total RNA was isolated using miRNeasy Mini Kit (Qiagen) with DNase I (Qiagen) digestion according to the manufacturer's instructions. RNA integrity was verified on an Agilent Bioanalyzer 2100 (Agilent Technologies, Palo Alto, Calif.). cDNAs were synthesized from total RNA using Superscript III (Invitrogen) and random primers (Invitrogen).

Quantitative Real-Time PCR

Quantitative Real-time PCR (qRT-PCR) was performed using Power SYBR Green Mastermix (Applied Biosystems, Foster City, Calif.) on an Applied Biosystems 7900HT Real-Time PCR System. All oligonucleotide primers were obtained from Integrated DNA Technologies (Coralville, Iowa) and are listed in Table 3. The housekeeping genes, GAPDH, HMBS and UBC, were amplified as controls. Fold changes were calculated relative to housekeeping genes and normalized to the median value of the lung benign samples.

RNA-Ligase-Mediated Rapid Amplification of cDNA Ends (RACE)

5' and 3' RACE was performed using the GeneRacer RLM-RACE kit (Invitrogen) according to the manufacturer's instructions. RACE PCR products were obtained using Platinum Taq High Fidelity polymerase (Invitrogen), the supplied GeneRacer primers, and appropriate gene-specific primers indicated in Table 3. RACE-PCR products were separated on a 2% agarose gels, bands excised and the extracted DNA (Gel Extraction kit, Qiagen) were cloned into pCR4-TOPO vector (Invitrogen), and sequenced bidirectionally using M13 forward and reverse primers at the University of Michigan Sequencing Core. At least four colonies were sequenced for every gel product that was purified and the data was analyzed using Sequencher software (GeneCodes).

siRNA Knockdown Experiments

Knockdown experiments were carried out in approximately $1\text{-}2 \times 10^5$ cells plated in 100 mm dishes. While THOR knockdown in MM603 cells was achieved with two sequential transfections (at 24 hr and 48 hr post-plating) with 50 μM experimental siRNA oligos or non-targeting controls, for THOR knockdown in H1299 cells only one siRNA transfection (24 hr post plating) was done. Only one transfection was performed for all protein coding gene knockdowns. Knockdowns were performed with RNAiMAX (Invitrogen) in OptiMEM media and its efficiency was determined by qRT-PCR 96 hr post-plating. All siRNAs were purchased from Dharmacon and their sequences (in sense format) are listed in Table 4.

Overexpression Studies

The THOR expression construct were generated by amplifying the full-length transcript from NCI-H1299 cells and subcloning into the pLenti6 expression vector (Invitrogen), LacZ constructs were used as controls. Following Sanger sequencing (University of Michigan Sequencing Core) confirmation of the inserts, lentiviruses were generated at the University of Michigan Vector Core. NCI-H1437 and SK-MEL-5 cells were infected with lentiviruses expressing THOR or LacZ and stable pools and clones were generated by blasticidin selection (Invitrogen). The THOR deletion constructs were also generated by amplifying by PCR using the full-length transcript as a template and were subcloned into the pLenti6 expression vector (Invitrogen).

Northern Blotting

Northern blotting was performed using the NorthernMax-Gly Kit (Ambion) following the manufacturer's protocol. Briefly, 20-30 ug of total RNA was denatured with Glyoxal loading dye solution for 30 minutes at 50° C., and separated on a 1% agarose glyoxal gel. The RNA was then transferred to Nylon Membrane (Roche) by capillary blotting with the transfer buffer and cross-linked with UV light (UV Stratalinker 1800). The membrane was subjected to a prehybridization step by incubation in Ultrahyb buffer (Ambion) at 68° C. for 1 hour. The membrane was incubated at 68° C. overnight with antisense p32 labeled RNA probe in Ultra-Hyb buffer. Following washing in accordance with the NorthernMax-Gly kit protocol, the membranes were exposed to HyBlot CL autoradiography film (Denville Scientific). The primer sequences used for generating the probes are given in Table 3.

Expression of Recombinant Protein

IGF2BP1 cDNA (NM_006546.3) was purchased from Gegecopoea. IGF2BP1 coding region was amplified by PCR and cloned into pFN19A (HaloTag®7) T7 SP6 Flexi vector (Promega). IGF2BP1 deletion constructs were generated by inverse PCR using primers described in Table 3. All clones were verified by DNA sequencing. The HaloTag fusion proteins were synthesized by incubating 3 μg plasmid with in vitro TNT® Quick-coupled Transcription/Translation System (Promega). Synthesized proteins were subjected to RNA Pulldown Assay.

Cell Proliferation Assays

Proliferation experiments were carried out by plating $1\text{-}2 \times 10^4$ cells or $0.15\text{-}0.3 \times 10^4$ cells in 24-well or 96-well plates respectively and grown in regular media. Growth rate was monitored by IncuCyte live-cell imaging system (Essen Biosciences) for the specified durations.

Murine Subcutaneous In Vivo Models

All experimental procedures were approved by the University of Michigan Committee for the Use and Care of Animals (UCUCA). Mice (CB-17 SCID) aged 5-7 weeks were injected with $0.25 \times 10^6$ cells with a Matrigel scaffold (BD Matrigel Matrix, BD Biosciences) in the posterior dorsal flank region (n=10 per cell line). Tumors were measured weekly using a digital caliper, and endpoint was determined as a tumor volume of 1000 mm$^3$. Upon reaching endpoint, or if the animal became fatally ill, the mouse was euthanized and the primary tumor resected. The resected specimen was divided in two halves: one preserved in 10% buffer formalin and the other snap frozen.

RNA In Situ Hybridization in Testis

THOR ISH was performed on thin (approximately 4 μm thick) tissue sections (Advanced Cell Diagnostics, Inc., Hayward, Calif.), as described previously (Mehra et al., Neoplasia N. Y. N 16, 1121-1127 2014). Appropriate batch positive and negative controls demonstrated expected staining patterns. Slides were examined for THOR ISH signals in morphologically intact cells and scored manually by a study pathologist. Specific THOR ISH signal was identified as brown, punctate dots.

Single-Molecule Fluorescence In Situ Hybridization in Cell Lines smFISH was performed as described (Raj et al., Nat. Methods 5, 877-879 2008), with some minor modifications. Cells were grown on 8-well chambered coverglasses, formaldehyde fixed and permeablized overnight at 4° C. using 70% ethanol. Cells were rehydrated in a solution containing 10% formamide and 2×SSC for 5 minutes and then treated with 10 nM FISH probes for 16 h in 2×SSC containing 10% dextran sulfate, 2 mM vanadyl-ribonucleoside complex, 0.02% RNAse-free BSA, 1 µg/µL E. coli tRNA and 10% formamide at 37° C. After hybridization the cells were washed twice for 30 minutes at 37° C. using a wash buffer (10% formamide in 2×SSC). Cells were then mounted in solution containing 10 mM Tris/HCl pH 7.5, 2×SSC, 2 mM trolox, 50 µM protocatechiuc acid (PCA) and 50 nM protocatechuate dehydrogenase (PCD). FISH samples were imaged in 3 dimensions using HILO illumination as described (Pitchiaya et al., EMBO Rep. 13, 709-715 2012). Images were processed using custom-written macros in ImageJ. Analysis routines comprised of 3 major steps: background subtraction, Laplacian of Gaussian (LoG) filtering and thresholding. Spots with intensity above set threshold are represented in images. All probes were obtained from Biosearch technologies and are listed in Table 5.

Western Blot Analysis

Western blot analysis was performed according to standard procedures using Immobilon-P filters (Millipore) and an Enhanced Chemiluminescence detection system (GE Healthcare). Details of the primary antibodies used are listed in Table 6.

RNA Immunoprecipitation (RIP) Assay

RIP assays were performed using a Millipore EZ-*Magna* RIP RNA-Binding Protein Immunoprecipitation kit (Millipore, #17-701) according to the manufacturer's instructions. RIP-PCR was performed using total RNA as input controls and 1:150 of RIP RNA product was used per PCR reaction. The antibodies (3-5 µg of antibody per RIP reaction) used for RIP are described in Table 6.

RNA Pulldown Assay

RNA-pull down assays were performed using a RiboTrap Kit (MBL, RN1011/RN1012) according to the manufacturer's instructions. Briefly, 5-bromo-UTP (BrU) was randomly incorporated into the THOR RNA upon transcription using THOR full-length or deleted fragments PCR products as templates. Next Anti-BrdU antibodies conjugated with protein G beads (Invitrogen), were bound to the in vitro synthesized RNA before incubating with NCI-H1299 cell lysates for 4 hr. Finally, the samples were washed, eluted, and subjected to Mass spectrometry analysis.

Mass Spectrometry

The samples were treated with SDS-PAGE loading buffer supplied with 10 mM DTT for 5 min at 85° C. The proteins were alkylated by the addition of iodoacetamide to the final concentration of 15 mM. The samples were subjected to SDS-PAGE and the whole lanes were cut out and digested with trypsin in-gel for 2 hours. The resulting peptides were extracted, dried and resuspended in 0.1% formic acid with 5% acetonitrile prior to loading onto a trap EASY-column (Thermo Scientific) coupled to an in-house made nano HPLC column (20 cm×75 um) packed with LUNA C18 media. Analysis was performed on Velos Pro mass spectrometer (Thermo Scientific) operated in data-dependent mode using 90-min gradients in EASY-LC system (Proxeon) with 95% water, 5% acetonitrile (ACN), 0.1% formic acid (FA) (solvent A), and 95% ACN, 5% water, 0.1% FA (solvent B) at a flow rate of 220 nl/min. The acquisition cycle consisted of a survey MS scan in the normal mode followed by twelve data-dependent MS/MS scans acquired in the rapid mode. Dynamic exclusion was used with the following parameters: exclusion size 500, repeat count 1, repeat duration 10 s, exclusion time 45 s. Target value was set at 104 for tandem MS scan. The precursor isolation window was set at 2 m/z. The complete analysis comprised two independent biological replicates.

MS Data Analysis

The resulting spectrum files were transformed into MGF format by MSConvert software and interrogated by MASCOT 2.4 search engine using human UniProt database version 15 concatenated with reverse sequences for estimation of false discovery rate (FDR) and with a list of common contaminants (40729 entries in total). The search parameters were as follows: full tryptic search, 2 allowed missed cleavages, peptide charges+2 and +3 only, MS tolerance 1 Da, MS/MS tolerance 0.5 Da. Permanent post-translational modifications was: cysteine carbamidomethylation. Variable post-translational modifications were: protein N-terminal acetylation, Met oxidation and N-terminal Glutamine to pyro-Glutamate conversion. The remaining analysis was performed as previously described (Poliakov et al., Mol. Cell. Proteomics MCP 10, M110.007039 2011). To summarize, the minimal ion score threshold was chosen such that a peptide false discovery rate (FDR) below 1% was achieved. The peptide FDR was calculated as: 2×(decoy_hits)/(target+decoy hits). Spectral counts for all detected proteins were assembled using an in-house written Python script. The adjustment of spectral counts was done by the same script as in (Poliakov et al., Mol. Cell. Proteomics MCP 10, M110.007039 2011).

RNA-Protein Interaction Assay

The in vitro transcribed BrU labeled RNA were heated at 92° C. for 2 min (to remove secondary structure), and incubated with recombinant myc-tagged proteins in RIP buffer (150 mM KCl, 25 mM Tris pH 7.4, 0.5 mM DTT, 0.5% NP40, 1 mM PMSF and protease inhibitor (Roche Complete Protease Inhibitor Cocktail Tablets) for 3 hr at 4° C. RNA-protein complexes of interest were then partially purified with anti-myc magnetic beads (Thermo) and the products were treated with proteinase K, to remove the protein components leaving the RNAs intact. The recovered RNAs were extracted using miRNeasy Mini Kit as described above.

RNA Endogenous Degradation Assay

Cells were treated with 5 µg/ml Actinomycin D (Sigma) and collected in Quiazol at the indicated time points after treatment. Purified RNA was subjected cDNA synthesis and qRT-PCR as described above. The slopes for decay plots were determined by simple linear regression, and transcript half-life was calculated as the x intercept at y=0.5, using GraphPad Prism.

Anchorage-Independent Soft Agar Colony Formation Assay

For H1437 and H1299 soft-agar colony formation assay, 1-3×10$^3$ cells were suspended in DMEM containing 0.3% agar, 10% fetal bovine serum, and layered on DMEM containing 0.6% agar, 10% FBS in 6-well plate. After 2 weeks incubation, colonies were stained with iodonitrotetrozolium chloride (Sigma) for overnight. Visible colonies were enumerated from two replicate wells.

In Vivo Xenograft Experiments

Male mice (CB17SCID) aged 5-7 weeks were injected with 0.25×10$^6$ NCI-H1437 LacZ or THOR over-expressing (THOR-OE) cells with a Matrigel scaffold (BD Matrigel Matrix, BD Biosciences) in the posterior dorsal flank region (n=10 per cell line). For THOR CRISPR knockout experiment, 1×10$^6$ vector control or THOR knockout H1299 cells were injected in the dorsal flank region of CB17SCID mice (n=10 per cell line). For the melanoma xenograft experiment, 1×10$^6$ LacZ or THOR overexpressing SKMEL5 were injected subcutaneously into CB17SCID mice (n=10 per cell line). In all murine xenograft experiments, tumor measurement was taken twice weekly using a digital caliper.

RNA-Seq Data Processing

RNA-sequencing reads were quantified to the human transcriptome (GENCODEv24) using Kallisto (v0.43.0) (Bray et al., Nat Biotech 34, 525-527 2016). GENCODEv24 GTF was obtained from GENCODE (Harrow et al., Genome Res. 22, 1760-1774 2012), and transcriptome fasta file was produced using the rsem-prepare-reference function of RSEM (version 1.2.26) (Li and Dewey, BMC Bioinformatics 12, 323 2011). Kallisto index was generated using the kallisto index function. Transcript level quantification obtained using the kallisto quant function. Gene level expression obtained by summing the TPM values for all transcripts within each gene.

RNA-Seq Differential Expression Testing

Differentially expressed genes were obtained by comparing non-targeting shRNA control to each of the two replicates for the three genes tested (i.e., THOR, IGF2BP1, and HUR) using DESeq2 (Anders and Huber, Genome Biol. 11, R106 2010). Significantly differentially expressed genes were defined as genes with a greater than 2^0.75 log-fold-change with a q-value <0.05.

Gene Signature GSEA Analysis

For each gene a rank list was generated by ordering each gene in the differential expression analysis by the DESeq log-fold-change value (log 2foldchange) by the q-value (padj). These rank lists were used in a weighted, pre-ranked GSEA analysis against MSigDBv5. Significant associations were determined for any gene set having an FWER p-value below 0.01.

iCLIP iCLIP was performed as previously described. Briefly, H1437-LacZ and H1437-THOR cells were cross-linked with UV light (UV Stratalinker 1800). After cell lysis, RNA was partially digested using RNase I (Life Technologies, AM2295), and IGF2BP1-RNA complexes were immunoprecipitated with anti-IGF2BP1 antibody (MBL International Corporation) immobilized on protein A-coated magnetic beads (Invitrogen). After 3' end dephosphorylation by T4 PNK (NEB, M0201L), RNAs were ligated at their 3' ends to a 3' Preadenylated RNA adaptor, radioactively labeled by p32-γ, and run in MOPS-based protein gel electrophoresis. After transferring to a nitrocellulose membrane, protein-RNA complexes 15-80 kDa above free protein were cut from the membrane. The SDS based RNA recovery platform was used as described previously. Reverse transcription primers containing a 6-nt experiment-specific barcode within an 8-nt random barcode at their 5' end to mark individual cDNA molecules were used. cDNA were size purified in TBE gel, circularized by CircLigase II (Cambio, CL9025K), annealed to an oligonucleotide complementary to the cleaved site and cut using BamHI (New England Biolabs Inc.). Linearized cDNAs were then PCR-amplified using AccuPrine SuperMix I (Invitrogen, 12342-010) and subjected to high throughput sequencing using Illumina HiSeq.

iCLIP Data Analysis

PCR duplicates were initially removed by collapsing identical reads. The iCLIP reads contained 8 random bases before the barcode, serving to distinguish reads arising from PCR amplification from reads arising from multiple RNA species. iCLIP eeads were first filtered for sequencing quality using the fastq_quality_filter tool in the FASTX-Toolkit (hannonlab.cshl.edu/fastx_toolkit) with the "-Q33 25" and "-p 80" flags. The fastx_collapser tool was used to collapse duplicate reads with the "–Q33" flag. Barcodes were trimmed from reads using the fastx_clipper tool, and random bases were trimmed using the fastx_trimmer tool also from the FASTX-Toolkit package.

Trimmed and deduplicated reads were then mapped to the GRCh38 genome using STAR (Dobin et al., 2013b; supra) using the "EndToEnd" option for the "-alignEndsType" flag, and "0.08" for the "-outFilterMismatchNoverLmax" flag. RT-stops were identified as the 5' base in aligned reads, and a custom BED file was created for a window of 15 bases up and downstream of the RT stop. These 30BP windows surrounding the RT-stops were then used to identify peaks using Piranha with the following commands: "-b 30 -s -p 0.01". Genes were identified as having IGF2BP1 binding if they were identified to have an exonic Piranha peak for both iCLIP replicates from the H1437 cells overexpressing THOR.

Embryo GFP Sorting 48 hpf embryos were harvested and dechlorinated with Pronase (2 mg/ml) in E2 medium (15 mM NaCl, 0.5 mM KCL, 2.7 mM CaCl2, 1 mM MgSO4, 0.7 mM NaHCO3, 0.15 mM KH2PO4, 0.05 mM Na2HPO4). After deyolking by pipetting with 200 ul tip in ½ Ginsberg Fish Ringer without Calucium (55 mM NaCl, 1.8 mM KCL, 1.25 mM NaHCO$_3$), embryos were re-suspended in the Protease Medium (0.25 Tripsin, 1 mM EDTA in PBS pH=8.0) and incubated for 40 min at 28 C with homogenizing with 200 ul tip every 10 min. After adding 100 ul FBS to stop reaction, cells were centrifuged for 3 min at 3,000 rpm, washed by Suspension Medium (08 mM CaCl2, 1% FBS in Leibovitz medium L-15 (GIBCO, 21083-027)) once, and filtered through strainer (352235, Falcon). GFP positive cells were sorted and collected in Quiazol followed by RNA extraction. Cell sorting and data analysis were performed by University of Michigan Flow Cytometry Core using MoFlo Astrios cell sorter (Beckman Coulter).

Cas9 Target Site Design, Vector Construction and In Vitro RNA Synthesis

The plasmids MLM3613 bacterial Cas9 expression vector ((Addgene plasmid #42251), (Mali et al., Science 339, 823-826 2013)) and DR274 sgRNA expression vector ((Addgene plasmid #42251), (Mali et al., 2013; supra)) were purchased from Addgene (Cambridge, Mass.). Two sgRNA targets with ZIFIT Targeter (zifit.partners.org/zifit/Introduction.aspx) were selected to generate a deletion of the conserved portion of THOR in zebrafish. For each target, the oligonucleotide pairs were annealed and ligated into Bsa I-linearized DR274. sgRNAs were transcribed from Dra I-linearized templates using the MEGAscript® T7 Kit (Ambion). Cas9 mRNA was transcribed in vitro with the mMES-SAGE mMACHINE T7 ULTRA kit (Ambion). RNAs were purified by RNA Clean &Amp; Concentrator (Zymo Research) and re-dissolved in RNase-free water.

Generation of THOR Knockout Cell Line

The plasmids pSpCas9(BB)-2A-GFP (PX458) (Addgene plasmid #48138) (Cong et al., 2013; supra) was purchased from Addgene (Cambridge, Mass.). Two sgRNA targets were selected with CRISPR Design (crispr.mit.edu) to generate a deletion of the conserved portion of human THOR. For each target, the oligonucleotide pairs were annealed and ligated into BbsI-linearized PX458 plasmid. Cells were transfected with two vectors using Lipofectamine 3000 (Life Technologies) according to the manufacturer's instructions. 48 hours post-transfection, mosaic cells were genotyped and subjected to further experiments. To obtain monoclonal clones, GFP-positive cells were FACS sorted as a single cell into 96-well plate. After culturing for 3 weeks, cells are distributed into two 24 well plates followed by PCR-based genotyping. A clone showing deletion of the targeted region in THOR was used for further analysis. Single-cell sorted cells obtained after transfection of the empty PX458 construct was used as a negative control. Cell sorting and data analysis were performed by University of Michigan Flow Cytometry Core using MoFlo Astrios cell sorter (Beckman Coulter).

Microinjection of Zebrafish Embryos

One-cell stage embryos were microinjected with 250 ng/ul Cas9 mRNA and 150 ng/ul of each sgRNAs by using a pneumatic pico-pump (PV-820, World Precision Instrument).

DNA Isolation and PCR Analysis for Identifying Deletion

For embryonic gDNA extraction, 20 pooled embryos were lysed in 20 µL lysis buffer (10 mM Tris HCl pH8.0, 2 mM EDTA, and 0.2% Triton) containing proteinase K (10 µg/mL) at 55° C. for 2 hrs followed by 95° C. for 10 minutes. 1 uL of lysate was used directly for genotyping PCR performed for 40 cycles of 10 s at 95° C., 30 s at 60° C., and 60 s at 72° C. after initial denaturing for 30 s at 95° C. PCR products were analyzed by 2% agarose gel. All genotyping primers are listed in Table 3.

Germ Cell Sorting

Germ cell sorting was performed as described previously (Gaysinskaya et al., Cytom. Part J. Int. Soc. Anal. Cytol. 85, 556-565 2014). Briefly, zebrafish testes were placed in 6 ml Collagenase I/Dnase I solution (200 U/ml Collagenase type I (Sigma-Aldrich) and 5 µg/ml DNAse I (Invitrogen) in Gey's Balanced Salt Solution (GBSS) (Sigma-Aldrich)) and shaken at 150 rpm for 10 min at 35° C. The temperature and agitation speed were the same for all subsequent incubation steps. The testes were gently pipetted halfway into the 10 minute incubation. Tubules were settled for 2 min at room temperature (RT), then the supernatant, enriched in interstitial testicular cells (somatic cells), was harvested. 6 ml Collagenase I/Dnase I/Trypsin solution (200 U/ml Collagenase type I, 5 µg/ml DNAse I and 0.025% Trypsin (Gibco) in GBSS) was added to the pellet and the tubules were gently pipetted. Halfway into the 25 minute digestion period, 60 µl of 2.5% Trypsin was added, and the tubules were pipetted again. At the end of the incubation time, pipetting was repeated. The resulting cell-dense suspension was passed through a Nylon cell strainer (Falcon). To the resulting filtered cell suspension 10 µl of 1 mg/ml DNAse I and 10 µl of 10 mg/ml Hoechst 33342 (Life Technologies) were added and incubated for 20 min. Halfway into the 20 minute period, the suspension was pipetted. At the end of incubation, 600 µl of FBS was added to inactivate the trypsin. After determining the cell number, the suspension was spiked with 10 µl of 1 mg/ml DNAse I, and stained with Hoechst dye for the final 6 µg Hoechst/million cells. The suspension was incubated for 25 min. The cells were then stained with 10 µl of PI (Sigma-Aldrich) at RT. Cell sorting and data analysis were performed by University of Michigan Flow Cytometry Core using MoFlo Astrios cell sorter (Beckman Coulter). Hoechst was excited using 375 nm laser, and the dye's emission spectrum detected in two distinct channels: the "Ho Blue" (450/40 nm band-pass filter) and the "Ho Red" (670 nm long pass filter). Cells from each subpopulation were sorted and subjected to qRT-PCR.

Generation of THOR Knockout Zebrafish

F0 zebrafish was crossed to wild-type AB* to generate F1 embryos that were screened for THOR deletion. F0 zebrafish that were able to produce germ-line deletion of THOR were crossed to produce F1 heterozygotes, which were subsequently genotyped and crossed to generate THOR homozygous. THOR homozygotes and matched wild-type fish were used for phenotypic analyses.

Zebrafish Mosaic Melanoma Model

All transgenic constructs were made using the Tol2/Gateway kit (a gift from Dr. Kristen Kwan) (Kwan et al., Dev. Dyn. Off. Publ. Am. Assoc. Anat. 236, 3088-3099 2007). Full-length human NRAS 61K was amplified from pBabe NRAS 61K construct (a gift from Channing Der (Addgene plasmid #12543), (Khosravi-Far et al., Mol. Cell. Biol. 16, 3923-3933 1996)) subcloned into BglII and BamHI restriction enzyme sites. GFP was amplified and subcloned into SalI and BamHI sites of pME entry vector. THOR transcript was amplified from THOR expression plasmid and cloned into SalI and BamHI sites of pME entry vector. The mitfa promoter was amplified using gDNA extracted from embryos as a template, and cloned into p5'E entry vector; and polyA tail was cloned into p3'E entry vector. These were assembled into the Tol2 destination vector using MultiSite Gateway Technology system (Invitrogen). 2.5 ng/µL of mitfa:NRAS 61K was co-injected into one-cell stage of p53-/- embryos (Berghmans et al., Proc. Natl. Acad. Sci. U.S.A. 102, 407-412 2005) with mitfa: THOR or mitfa:mCherry (25 ng/ul each) with 2.5 ng/ul of Tol2 mRNA. For injections into THOR-/- embryos and their corresponding wild type embryos, 5 ng/µL of mitfa:NRAS 61K was injected into one-cell embryos with 5 ng/ul of Tol2 mRNA. Zebrafish were inspected weekly, then euthanized when 17 weeks old and fixed in 4% paraformaldehyde overnight. After taking photos, they were then decalcified in 0.5 M ethylenediaminetetraacetic acid before paraffin embedding and sectioning. Staining and immunohistochemistry were done using the standard techniques by the University of Michigan URAM Core. Percentage of melanoma area per body was calculated using ImageJ software. Antibodies used for immunohistochemistry are described in Table 6.

Results

Discovery of THOR, a Conserved lncRNA Expressed in the Testis

Figure 1B:
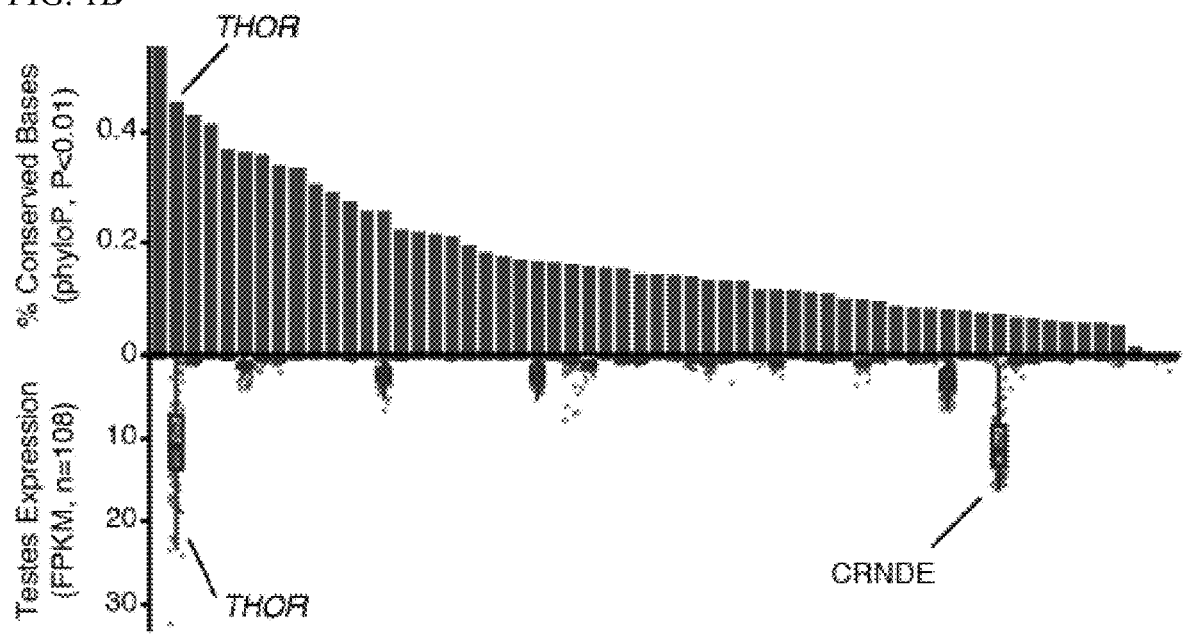
Figure 1C:
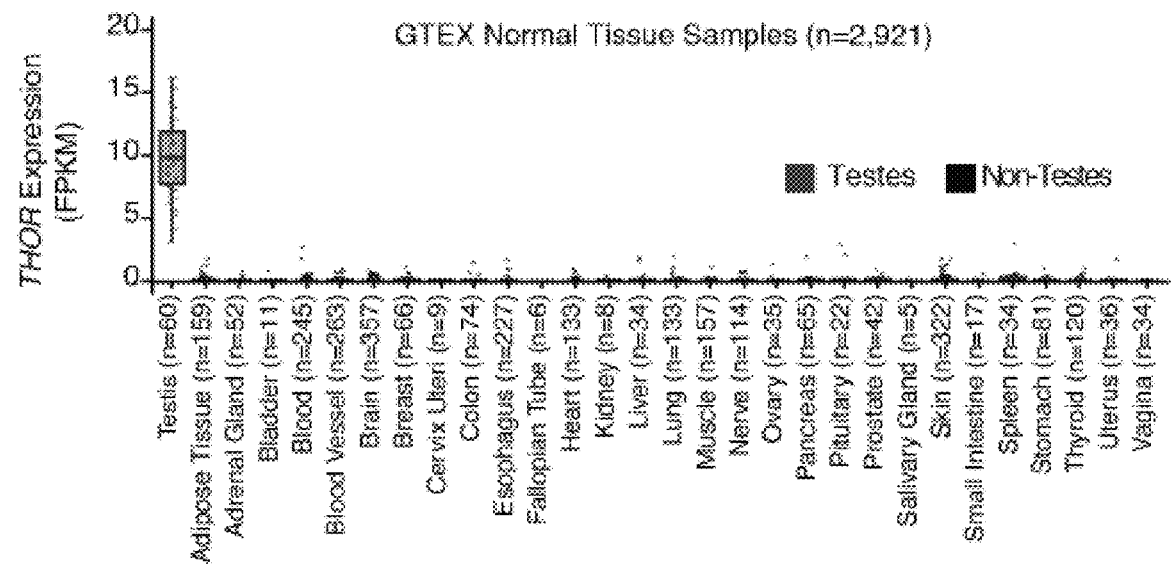
Figure 1D:
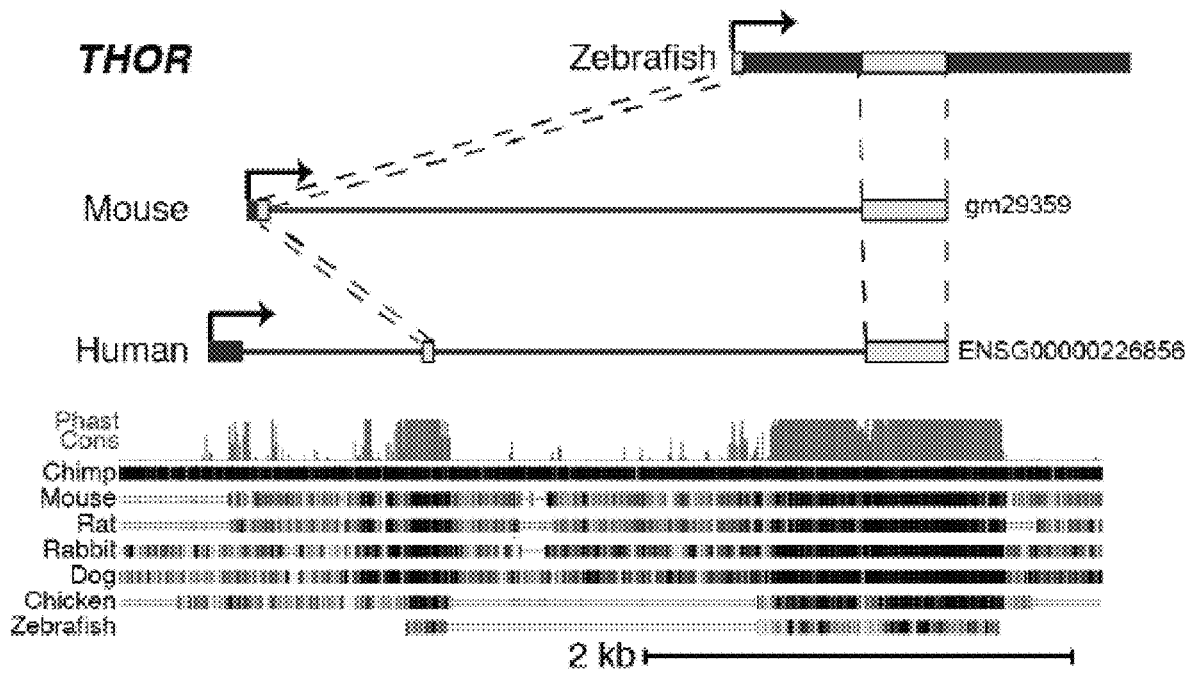
Figure 8A:
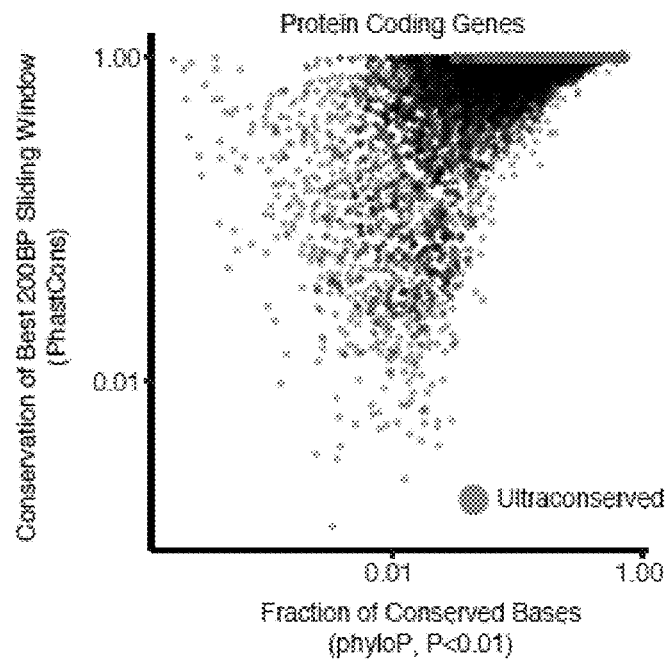
FIG. 8A-E. Conservation of protein-coding genes and expression of CRNDE in normal tissue. A, Scatter plot depicting the distribution of basewise transcript conservation levels (x axis) and the average conservation for the best 200 bp window (y axis) for all protein coding genes expressed at 1 FPKM or more in the top 1% of TCGA samples. B, Expression of lncRNA CRNDE amongst the GTEX normal tissue RNA-seq dataset, spanning a myriad of different normal tissue types. C-E, UCSC genomic browser view of THOR represented in the UCSC browser for (C) human GRCh37, (D) mouse GRCm38, and (E) zebrafish Zv9. THOR structure depicted along with H3K4me3 histone marks (ENCODE), conservation (Phylop and PhastCons) and Multiz 100 vertebrate alignment.
Figure 8B:
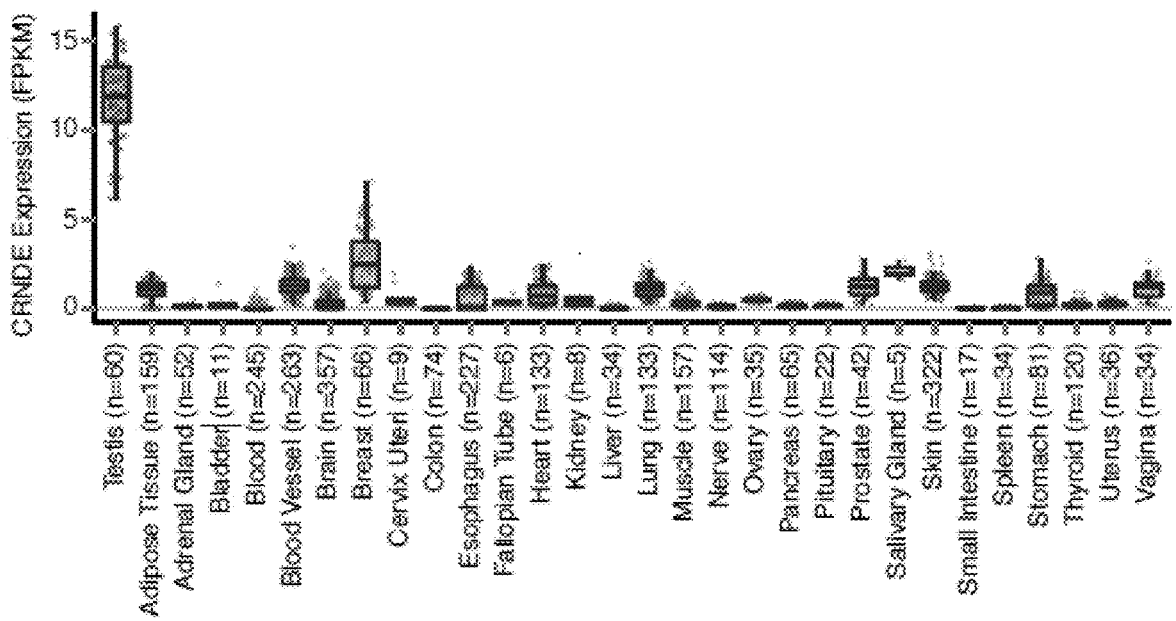

In a recent large-scale RNA-sequencing analysis, we comprehensively profiled the human transcriptome, discovering tens of thousands of novel lncRNAs (Iyer et al., supra). While lncRNAs tend to be less conserved than protein-coding genes (FIG. 8A) and most do not exhibit marked sequence conservation, a subset of conserved lncRNAs does exist (FIG. 1A). Both the average base-wise conservation of the entire transcript (FIG. 1A, x-axis) and the level of conservation of the best 200 bp window (FIG. 1A, y-axis), a metric previously utilized to determine "ultraconserved" elements (Hudson et al., 2013; supra; Iyer et al., supra) were measured and 82 intergenic ultraconserved lncRNAs with expression of at least 1 FPKM in the top 1% of samples in our tissue RNA-seq compendium (FIG. 1A,B and Table 1)

were identified. Despite possessing a 200 bp ultraconserved segment, these lncRNAs possessed varying degrees of base-wise conservation (FIG. 1B, top; range, 0.1%-55.4% conserved bases), with THOR exhibiting the second highest degree of base-wise conservation. Interestingly, when interrogating the GTEX benign tissue RNA-seq dataset (Consortium, Nat. Genet. 45, 580-585 2013; Melé et al., Science 348, 660-665 2015), two of these ultraconserved lncRNAs, THOR and CRNDE, displayed substantial expression in the testes (FIG. 1B, bottom). Further analysis was focused on THOR due to its testis-specific expression pattern (FIG. 1C), compared to the promiscuous expression of CRNDE (FIG. 8B).

Transcriptional THOR Homologues Exist in the Mouse and Zebrafish

Figure 2A:
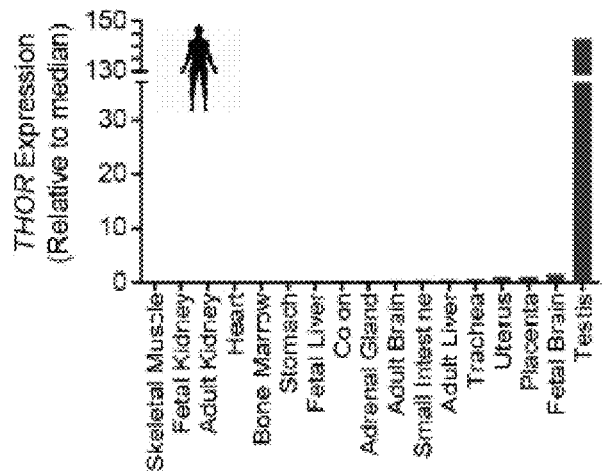
FIG. 2A-D. THOR exhibits testis-specific expression. A, Estimation of THOR mRNA expression by qRT-PCR in human adult normal tissue panel. B, H&E stain of human testis at high magnification (400×) (right), and RNA-ISH of THOR in human testis (left). Various cells of the testis are labelled as follows: (1) spermatogonia, (2) spermatocytes, (3) spermatids, (4) mature spermatozoa, and (5) scattered Sertoli cells with a single central prominent nucleolus. THOR expression is observed in the spermatid and spermatocyte. C, Measurement of mouse THOR expression by qRT-PCR on an adult murine tissue panel (left) and embryos (right). D, Quantification of zebrafish THOR expression by qRT-PCR on a piscine tissue panel (left) and embryos (right).
Figure 2B:
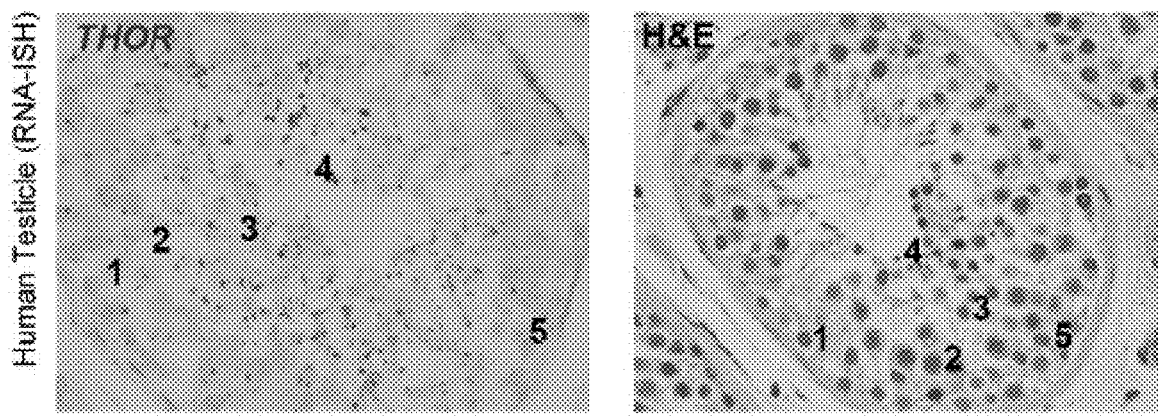
Figure 2C:
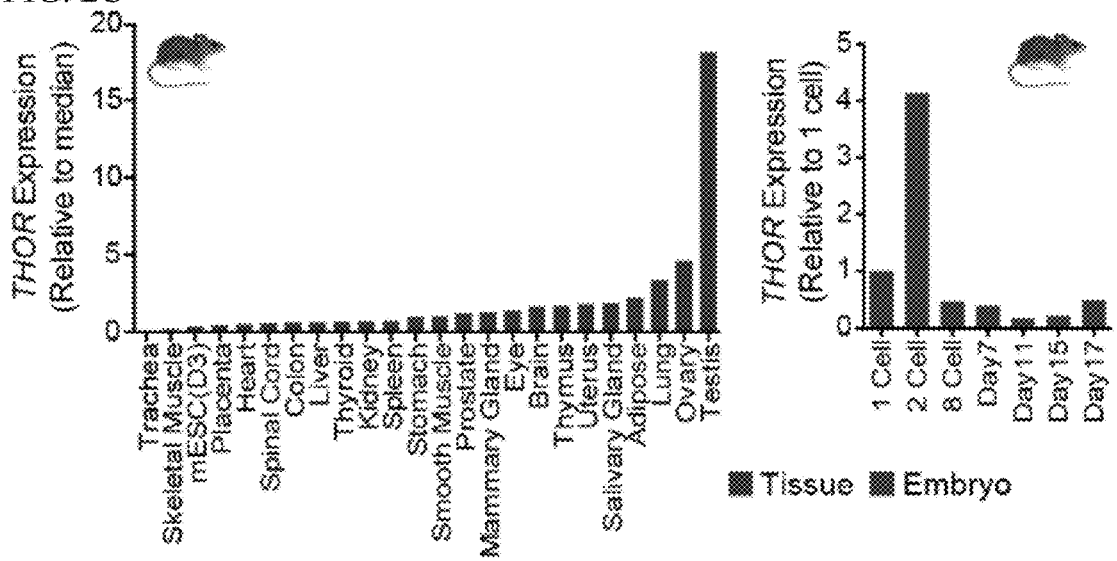
Figure 2D:
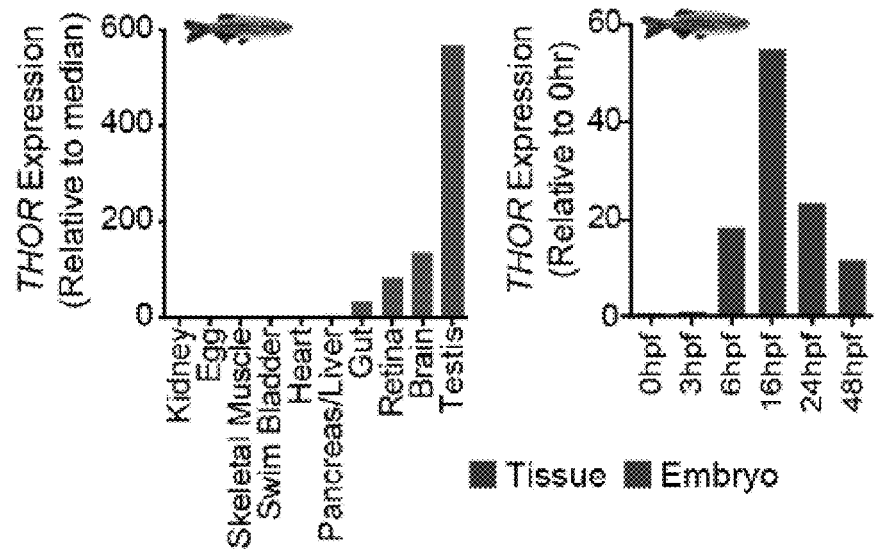

Utilizing structure prediction from prior RNA-seq assembly (Iyer et al., supra) and from corroboration of 5' and 3' rapid amplification of cDNA ends (RACE), two isoforms of THOR, comprised of either 2 or 3 exons on chromosome 2 (FIG. 8C and Table 2) were identified. Additionally, existence of the 3 exon isoform of THOR was confirmed via Northern blotting in the H1299 human lung adenocarcinoma cell line (FIG. 9A). While the GENCODE annotated gene has an additional larger isoform with a downstream exon, expression of this isoform was not detected in any of the cell lines used in this study (FIG. 9B), and addition of THOR-targeting siRNA did not alter the expression of the long isoform (FIG. 9C). Given its substantial sequence conservation, THOR homologues were identified in other species. Utilizing the BLAT tool (Kent, Genome Res. 12, 656-664 2002), predicted regions in the mouse and zebrafish genome homologous to the human THOR (h-THOR, Ensemble ID: ENSG00000226856) were identified (FIG. 2D). Additionally, elevated THOR expression was observed during the early development of both the mouse and zebrafish (FIG. 2C,D, right).

THOR Exhibits an Evolutionarily Conserved Expression Pattern in Normal Tissues

To obtain an independent validation of testis specific THOR expression observed in the GTEX RNA-seq data, quantitative real-time PCR (qRT-PCR) was performed with cDNA derived from various normal human tissues, observing a similarly testis-specific expression pattern (FIG. 2E). Moreover, RNA in situ hybridization (ISH) of human testis tissue using h-THOR specific probes revealed an enrichment of THOR testis expression in the spermatocyte and spermatid (FIG. 2B) but not in surrounding tissue (FIG. 9H, I). This expression pattern for THOR is a similar expression pattern to that reported for cancer/testis antigens not found on the X-chromosome (Simpson et al., Nat. Rev. Cancer 5, 615-625 2005; Tapparel et al., Gene 323, 189-199 2003). Querying additional RNA from tissue panels in the mouse and zebrafish identified testis-specific expression for both m-THOR (FIG. 2C) and z-THOR (FIG. 2D). Additionally, elevated THOR expression was observed during the early development of both the mouse and zebrafish (FIG. 2 C, D, right).

Expression and Functional Implication of THOR in Human Cancers

Figure 3A:
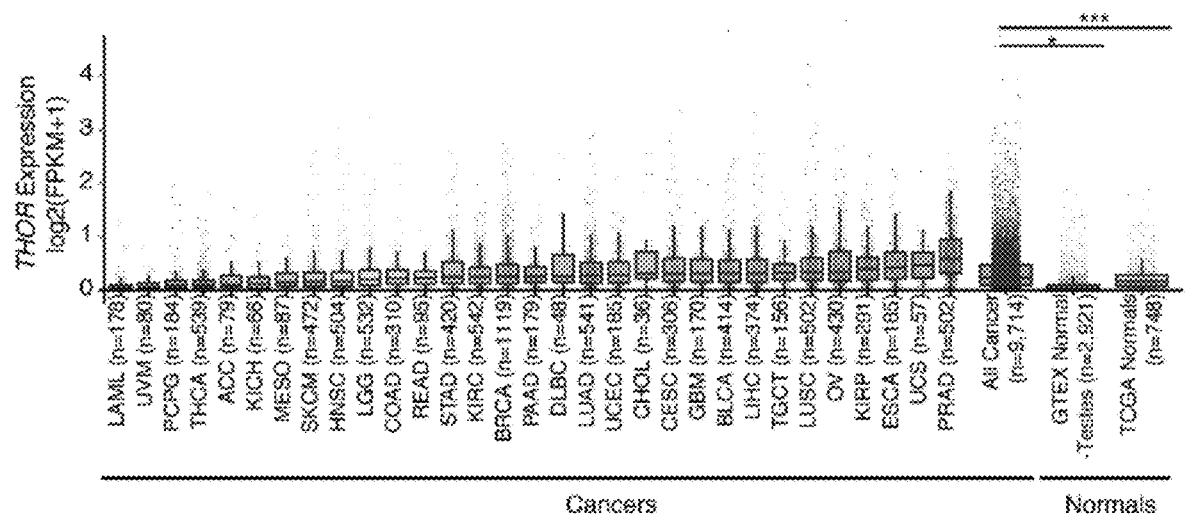
Figure 3B:
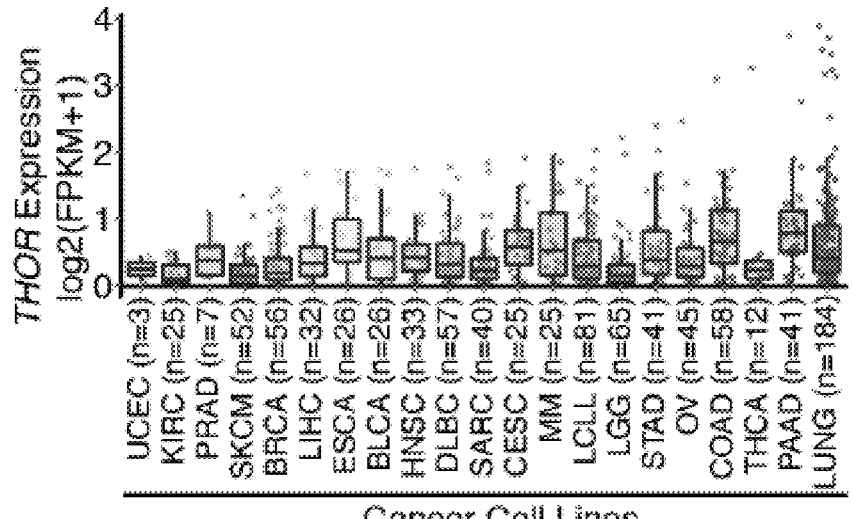
Figure 3C:
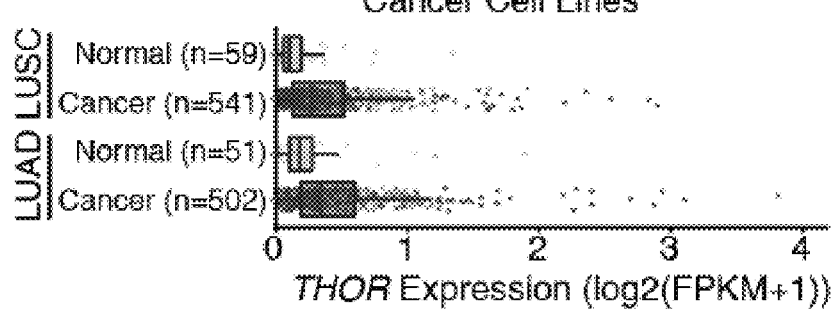
Figure 3D:
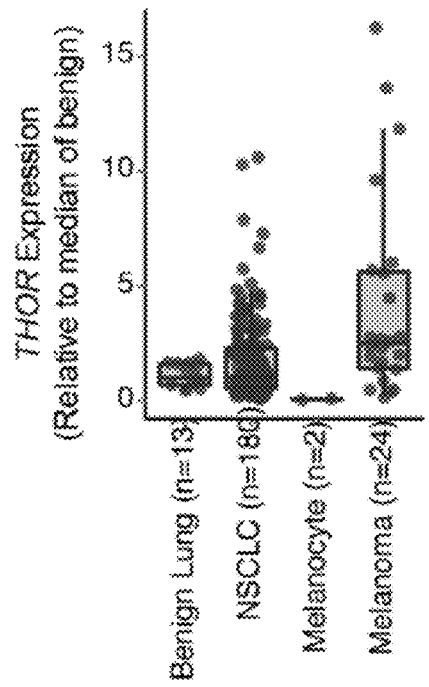

Further interrogation of the expression of THOR in cancer tissue RNA-seq samples from the TCGA revealed that, despite bearing a benign expression pattern restricted to the testis, THOR is widely expressed in a number of tumor types and is expressed significantly higher in cancers compared to both the GTEX normal and the TCGA normal samples (FIG. 3A). Additionally, THOR was expressed in a multitude of the cell lines in the Cancer Cell Line Encyclopedia (Barretina et al., Nature 483, 603-307 2012) with the highest expression in lung cancer cell lines (FIG. 3B). In both subtypes of lung cancer represented in the TCGA (lung adenocarcinoma, LUAD; lung squamous carcinoma, LUSC), THOR expression was significantly higher in cancer in comparison to matched benign adjacent normal tissue (FIG. 3C). This cancer specific non-small cell lung cancer (NSCLC) expression was confirmed by performing h-THOR qRT-PCR on RNA from an independent cohort of tumor and normal lung tissue obtained from the University of Michigan (FIG. 3D). This cohort also contained both melanoma and benign melanocytes, in which THOR similarly exhibited cancer specific expression (FIG. 3D).

Figure 3E:
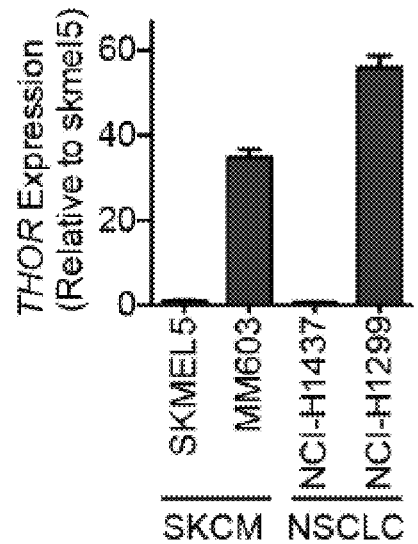
Figure 3F:
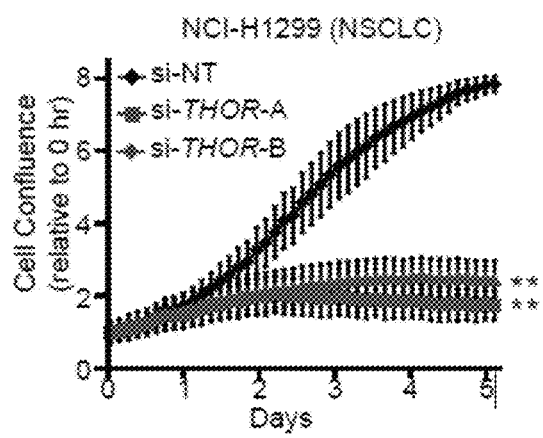
Figure 3G:
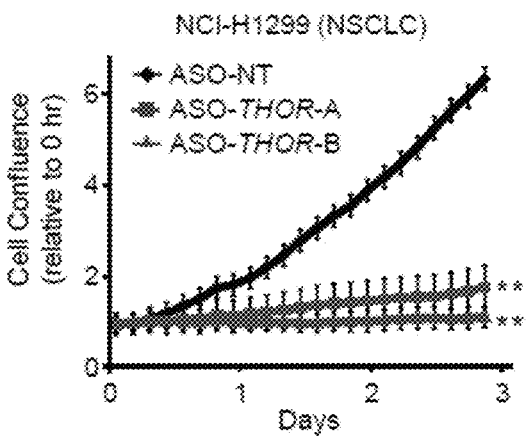
Figure 3H:
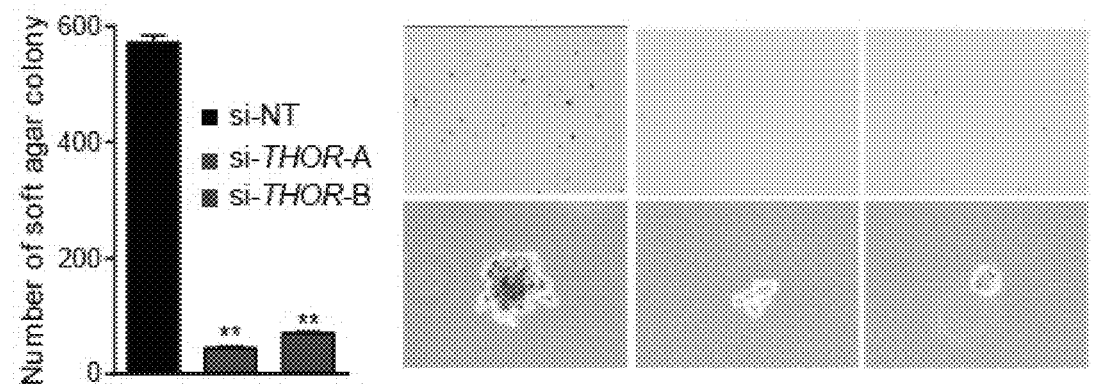
Figure 3I:
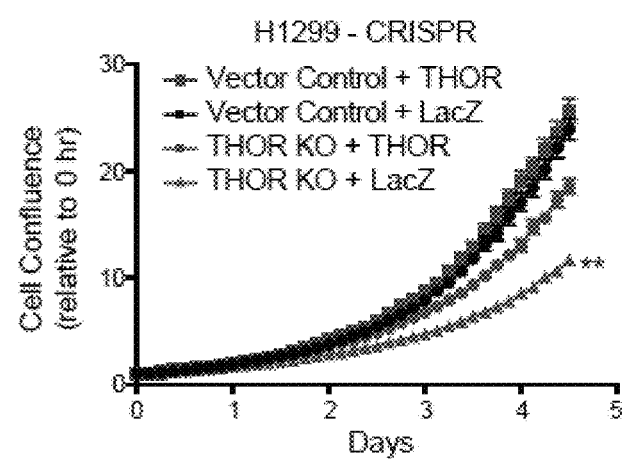
Figure 3J:
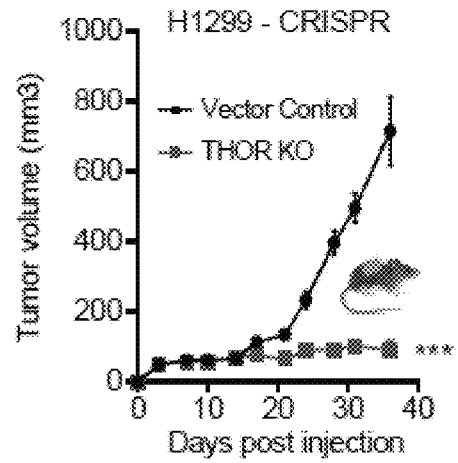
Figure 9J:
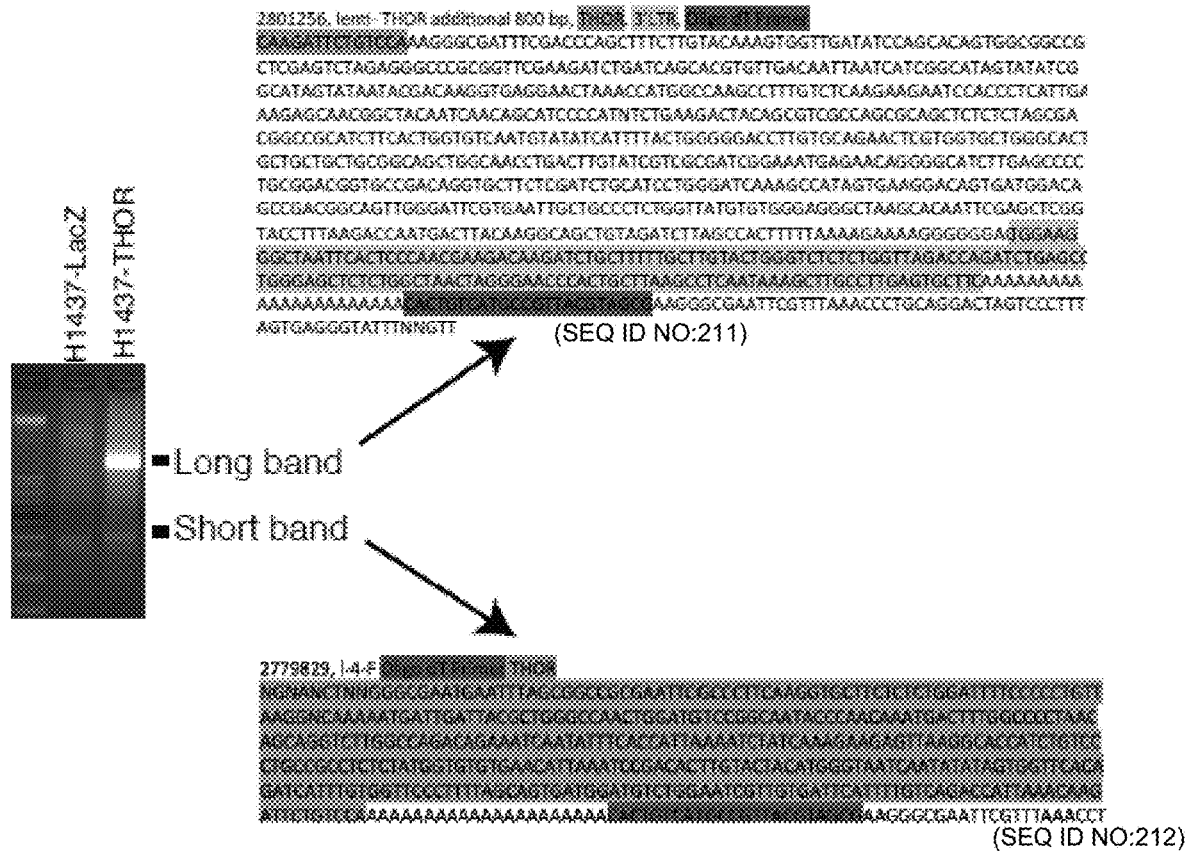
Figure 9K:
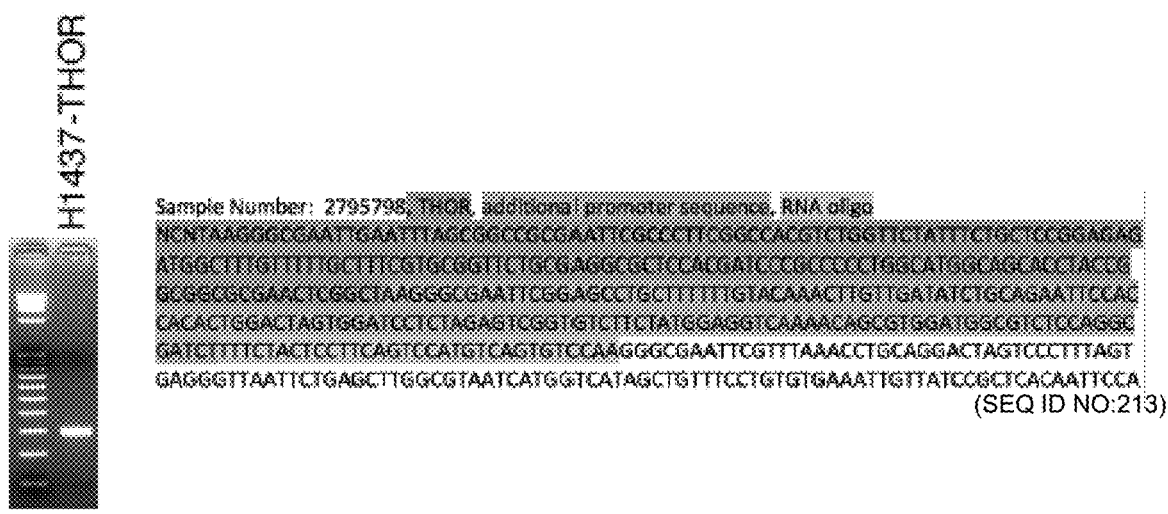
Figure 10G:
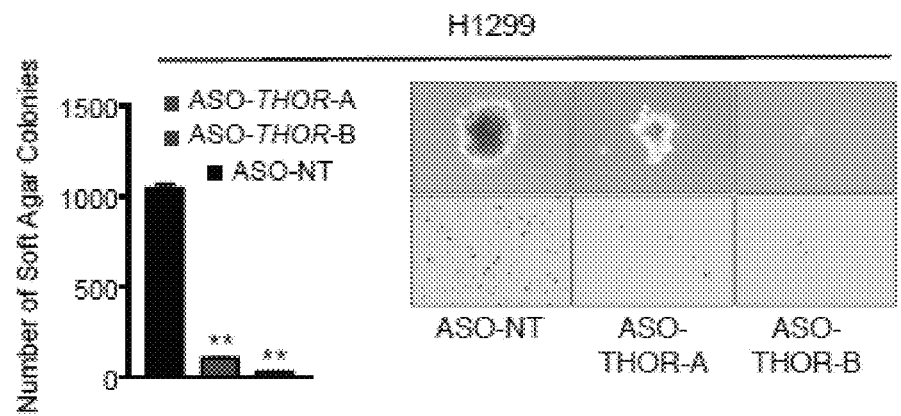
FIG. 10A-U. THOR knockdown efficiency and cancer phenotype assays. A, Knockdown efficiency of two independent siRNAs against THOR in NCI-H1299 and MM603 cells determined by qRT-PCR. Data show mean±S.D. B, Knockdown efficiency of two independent ASOs against THOR in NCI-H1299 and MM603 cells determined by qRT-PCR. Data show mean±S.D. C, Cell proliferation assays for MM603 cells treated with two independent THOR siRNAs. D, Cell proliferation of MM603 cells treated with two independent ASOs. E, Cell proliferation assays for NCI-H1437 cells treated with two independent THOR siRNAs. Data show mean±S.E. from one of the two independent experiments. F, Cell proliferation assays for SK-MEL-5 cells treated with two independent THOR ASOs. Data show mean±S.E. from one of the two independent experiments. G-H, Anchorage-independent growth of (G) H1299 cells transfected with non-targeting ASO or two THOR ASOs, (H) MM603 cells transfected with non-targeting siRNA and siRNAs targeting THOR, and (I) MM603 cells transfected with non-targeting ASO and ASOs targeting THOR. Left, quantification of number of colonies. Right, representative image of surviving colonies and individual colony. K, DNA agarose gel confirming knockout of THOR region flanked by sg #2 and sg #3 vis PCR. L, qPCR validation of THOR expression in control cells compared to knockout cells. M, DNA agarose gel confirming knockout of regions flanked by sgRNAs in the various conditions vis PCR in H1299 cells. N, RNA knockout efficiency for the mosaic CRISPR knockout models determined by qPCR. O, Proliferation assay for the mosaic populations for the THOR knockout H1299 cells produced via various sgRNA combinations compared to non-targeting sgRNA. P, DNA agarose gel confirming knockout of regions flanked by sgRNAs in the various conditions vis PCR in H1437 cells. Q, Proliferation assay for the mosaic populations for the THOR knockout H1437 cells produced via various sgRNA combinations compared to non-targeting sgRNA. R, Overexpression efficiency of THOR in NCI-H1299 and SK-MEL-5 cells. Data show mean±S.D. S, Cell proliferation assay in SK-MEL-5 cells stably transfected with THOR overexpression or LacZ control lentivirus. Data show mean±S.E. from one of the two independent experiments. T, Anchorage-independent growth of LacZ or THOR overexpressing SKMEL5 cells. Left, quantification of number of colonies. Right representative images of surviving soft agar colonies. U, Tumor growth for THOR overexpressing SKMEL5 cell line xenografts (N=10) and control LacZ samples (N=10).
Figure 10H:
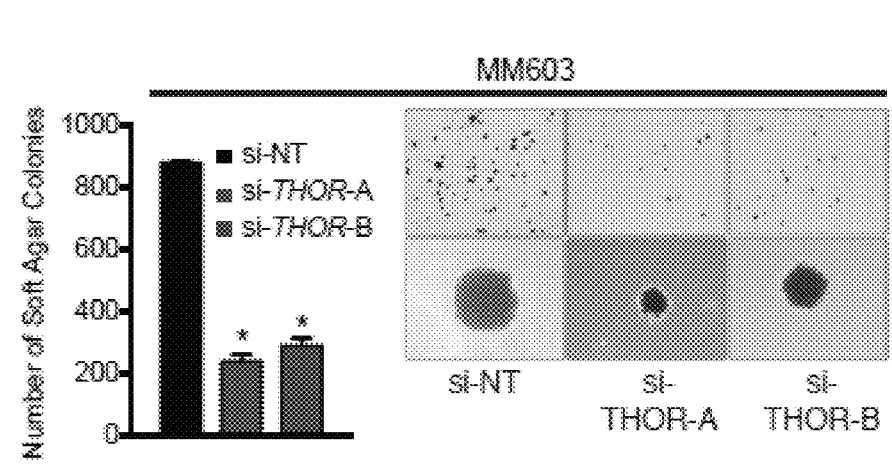
Figure 10L:
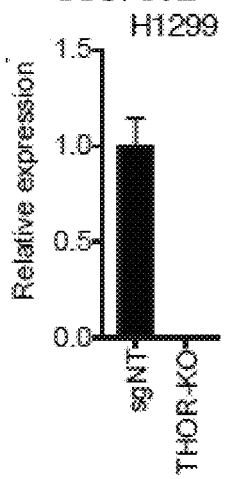
Figure 10I:
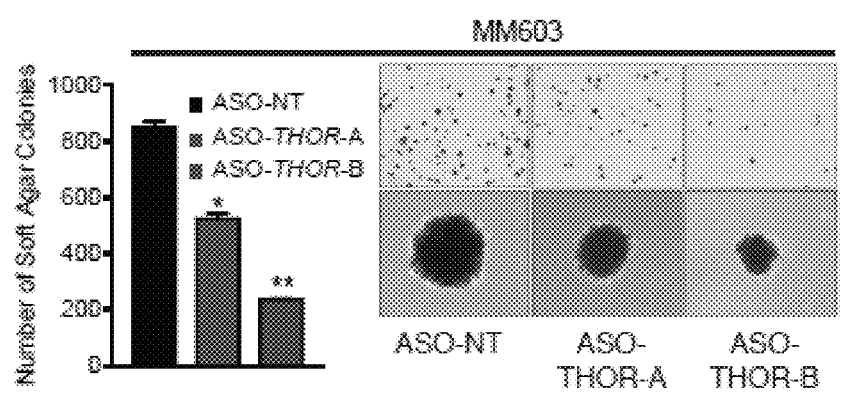
Figure 10K:
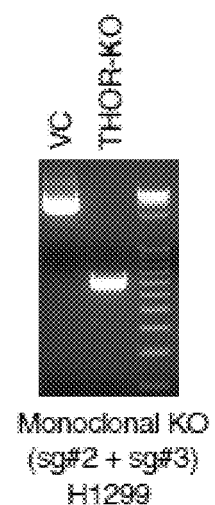
Figure 10J:
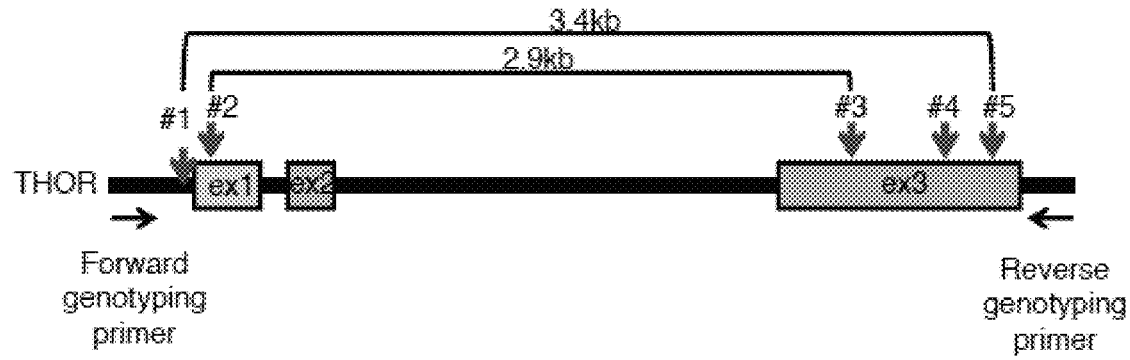
Figure 10M:
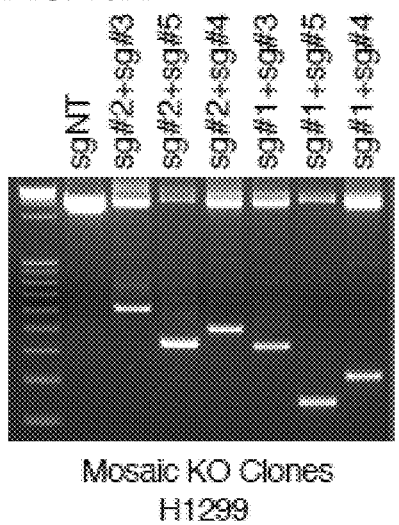
Figure 10N:
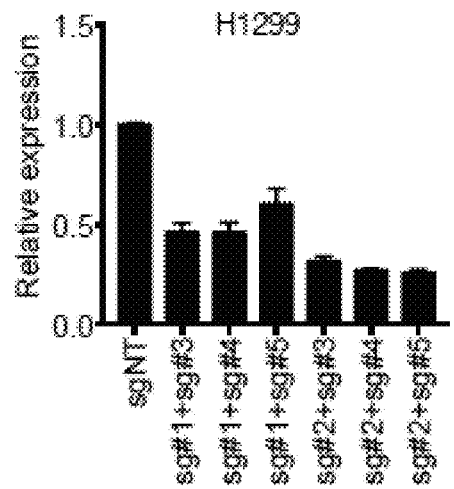
Figure 10O:
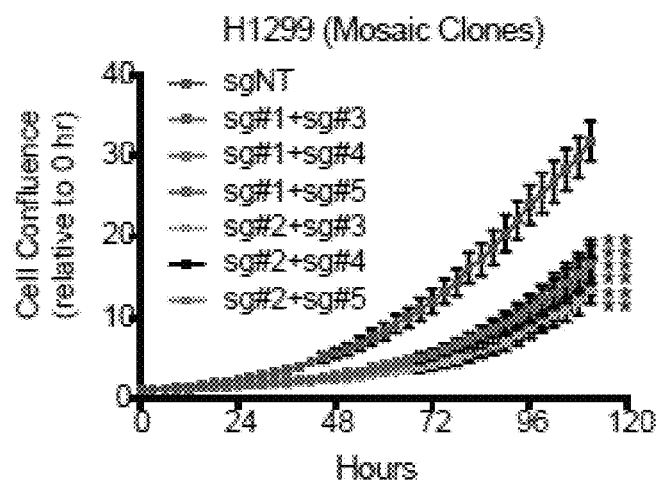
Figure 10P:
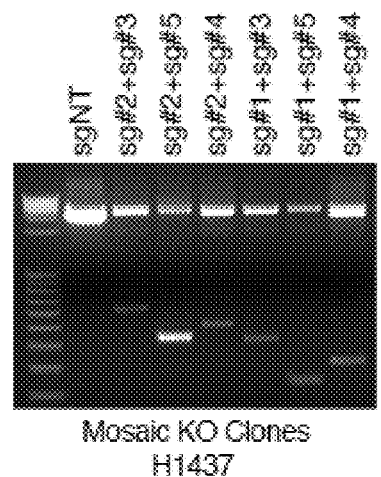
Figure 10Q:
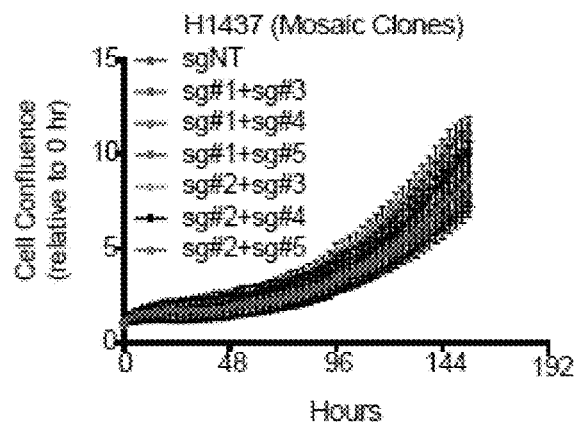
Figure 10R:
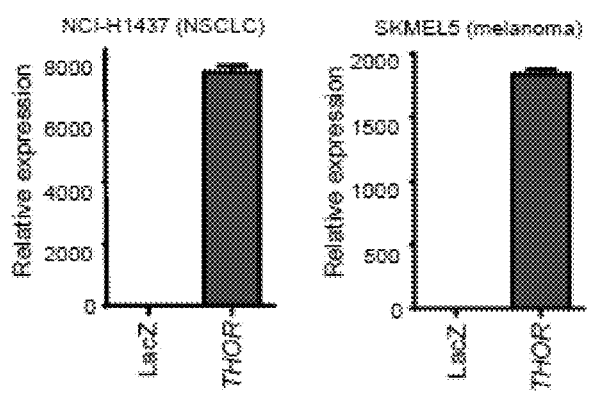
Figure 10S:
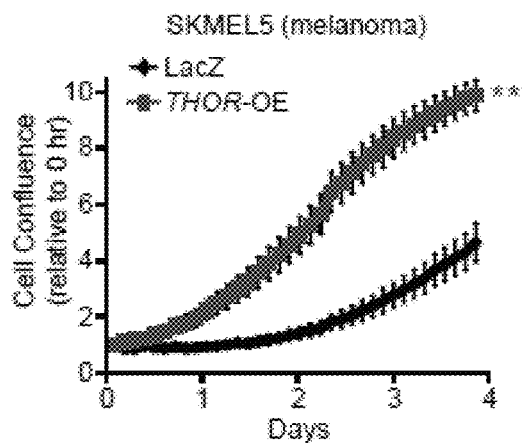
Figure 10T:
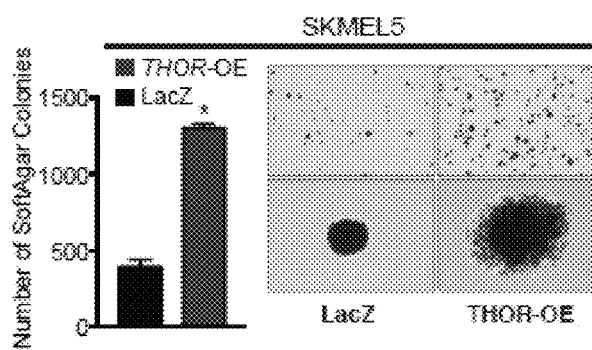
Figure 10U:
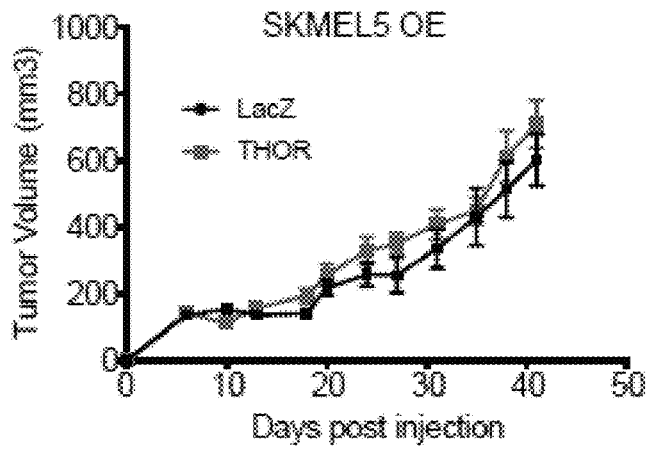

In order to interrogate the potential role of THOR in cancer processes, its function in NSCLC and melanoma cell lines was investigated. Knockdown of THOR via siRNA and ASO in H1299 and MM603, NSCLC and melanoma cell lines with high levels of THOR (FIG. 3E and FIG. 10C,D) resulted in a dramatic reduction in the proliferative capacity of these cells (FIG. 3F,G and FIG. 10C,D). siRNA and ASO knockdown of THOR in H1437 cells (lacking endogenous THOR expression FIG. 3E) exhibited no significant proliferation phenotype (FIG. 10E,F). THOR knockdown resulted in reduced colony formation in soft via both ASO and siRNA knockdown (FIG. 3H and FIG. 10G-I) and siRNA knockdown (FIG. 10H). Additionally, a THOR knockout cell line model was generated via CRISPR-Cas9 technology with paired single-guide RNAs (sgRNAs) targeted to the conserved region of THOR transcript in the H1299 cell line. Multiple sgRNAs were utilized targeting varying regions of THOR (FIG. 10J), and a monoclonal population of one of the sgRNA combinations exhibiting significant knockout of THOR at both the DNA and RNA level was selected for further use (FIG. 10K, L). Similar to the results shown for siRNA and ASO knockdown, the THOR knockout H1299 cells exhibited significantly reduced cell proliferation (FIG. 3I). Further corroborating the capacity for THOR to act in trans, a recovery of the proliferation phenotype when ectopically expressing THOR in the context of CRISPR-mediated knockout was observed (FIG. 3I). These results were also recapitulated in a mosaic population of knockout clones, suggesting that the monoclonal findings are not due to selection bias (FIG. 10M-O). Further corroborating on-target effects, THOR mosaic knockout in H1437 cells (FIG. 10P) did not result in reduced proliferation (FIG. 10Q). Moreover, a mouse xenograft of H1299 cells containing THOR knockout exhibited markedly reduced tumor growth compared to control knockout cells (FIG. 3J). Cells with stable lentiviral THOR overexpression in H1437 and SKMEL5 (FIG. 10R) exhibited significant increases in proliferative capacity (FIG. 3K and FIG. 10S) and soft agar colony formation (FIG. 3L and FIG. 10T). Additionally, murine tumor xenografts derived from cells stably overexpressing THOR in H1437 cells exhibited a significant proliferative advantage when compared to cells stably overexpressing LacZ control (FIG. 3M). However, this finding was not significant in a murine xenograft using SMKELS cells (FIG. 10U). Interrogation of the lentiviral plasmid via Northern blotting revealed an unexpected long isoform of THOR in addition the isoform included in the plasmid (FIG. 9A). 5' and 3' RACE identified a segment of plasmid in the expressed in the longer isoform (FIG. 9J,K), however, THOR targeting siRNAs did reduce levels of this isoform, suggesting functional fidelity of this longer isoform (FIG. 9A).

Characterization of the THOR-IGF2BP1 Interaction

Figure 11A:
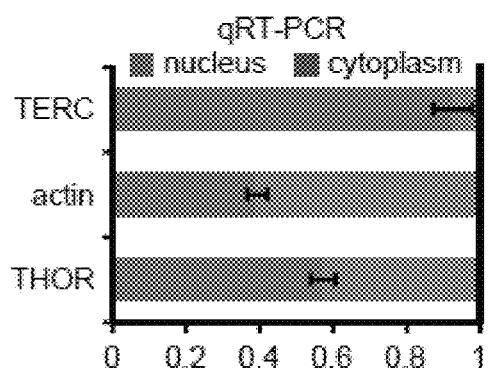
FIG. 11A-N. THOR cellular localization. A, qRT-PCR for TERC, ACTB, and THOR following nuclear and cytoplasmic fractionation of NCI-H1299 cell lysates demonstrates both nuclear and cytoplasmic expression of THOR. B, Single molecule RNA in situ hybridization in NCI-H1299 cells. (C, E, G) Representative, pseuodocolored images of H1299 or H1437 cells, treated with various siRNAs, ASOs or overexpression constructs and stained for DAPI (magenta) and THOR (grey). Scale bar, 10 μm. (D, F, H) Quantification of fold change in THOR expression of samples represented in D, E, G respectively. I, Venn diagram depiction of the proteins preferentially bound to sense THOR (compared to antisense) from nuclear or cytoplasmic lysate from H1299 cells. Jdiagram of the RRM and KH domains on the IGF2BP1 protein. N, Western blot of input (top) and following RNA-pulldown of BrU labelled THOR (bottom) for Halo-tagged mutant IGF2BP1 with various IGF2BP1 protein domains deleted. Error bars, s.e.m. (n=4; >300 cells per replicate, per sample; *$p<0.05$; ****$p<0.0001$).
Figure 11B:
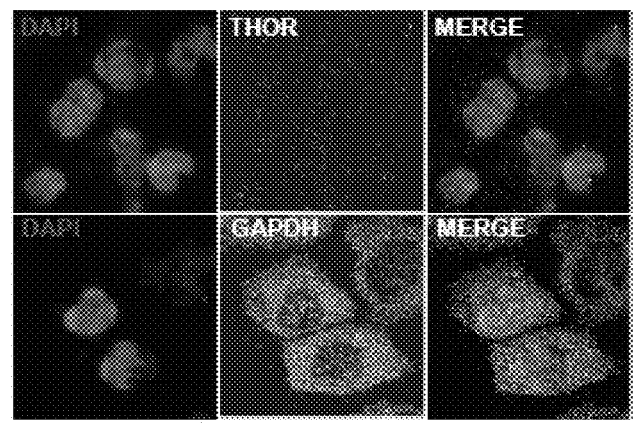
Figure 11C:
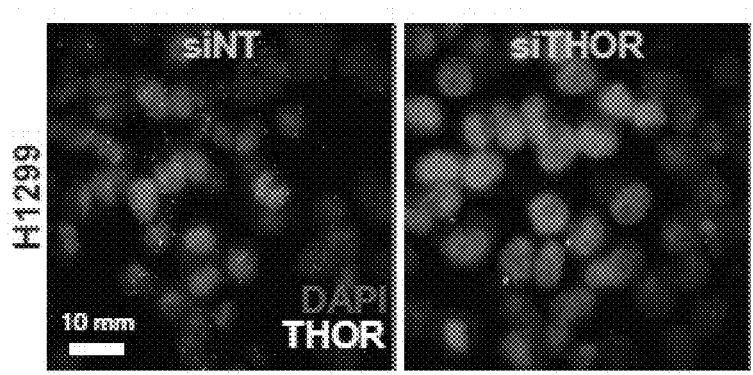
Figure 11D:
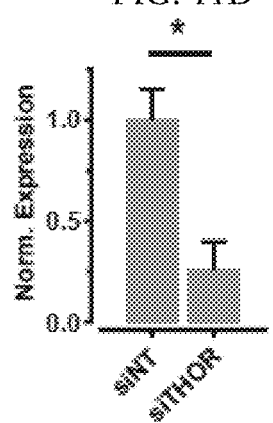
Figure 11E:
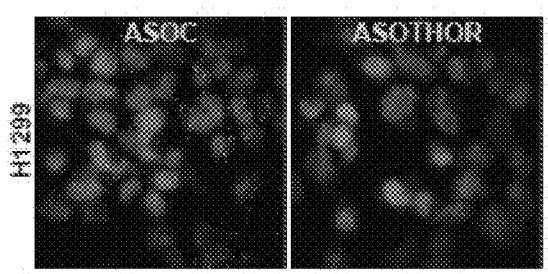
Figure 11F:
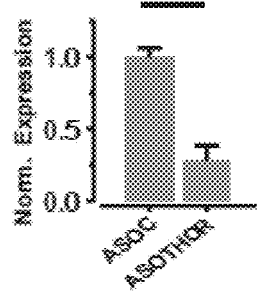
Figure 11G:
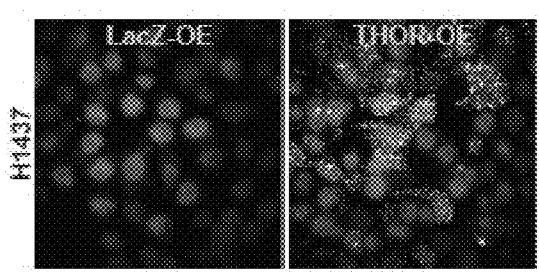
Figure 11H:
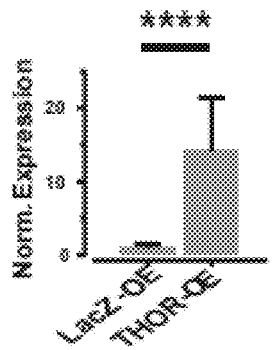
Figure 11I:
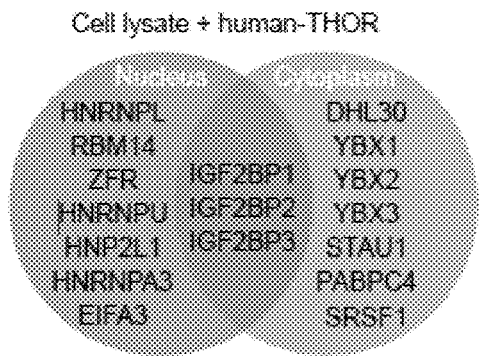
Figure 11J:
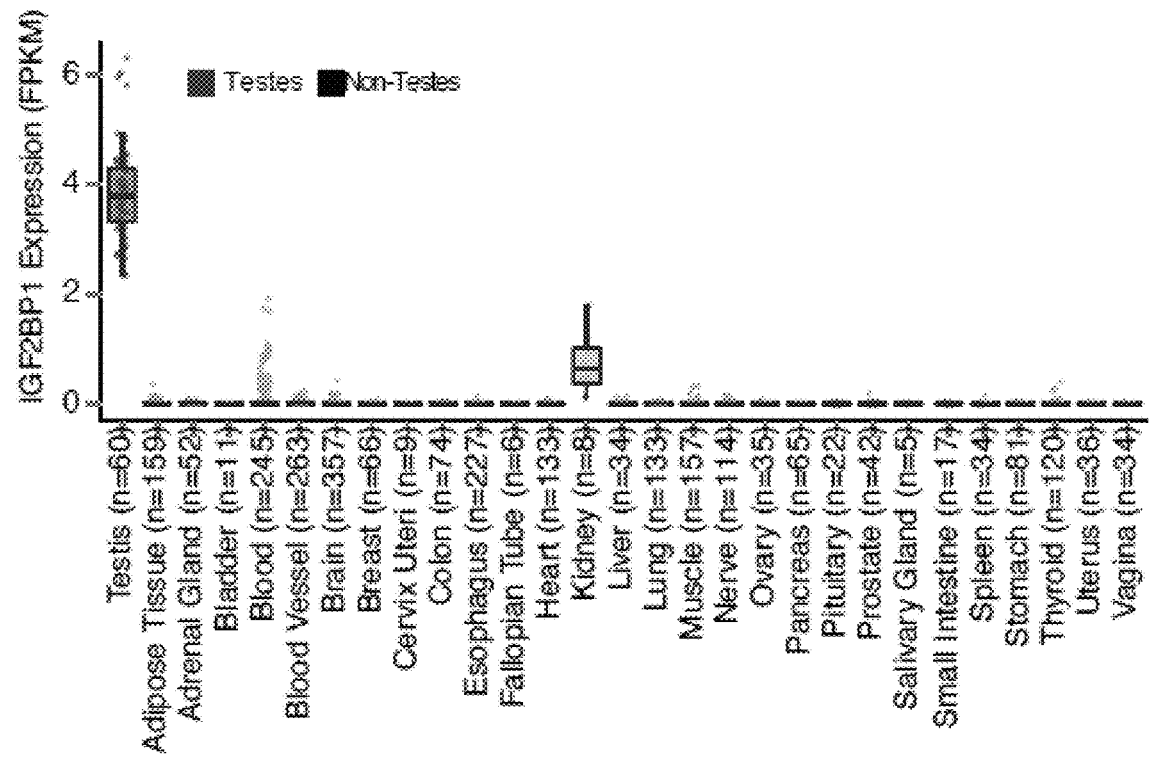

To characterize the mechanism through which THOR is functioning in cells, the cellular localization of THOR was investigated, observing it to be present in both the cytoplasm and nucleus via qRT-PCR following cellular fractionation (FIG. 11A) and via single molecule fluorescence in situ hybridization (ISH) (FIG. 11B-H). THOR protein interactors were identified via RNA-pulldown followed by mass-spectrometry. Building on the sequence conservation of THOR, protein-binding interactions that were also conserved were identified. This was accomplished by utilizing four conditions for RNA-pulldown mass spectrometry: 1) pulldown of h-THOR added to human H1299 cancer cell lysate, 2) pulldown of h-THOR added to zebrafish embryo lysate, 3) pulldown of z-THOR added to human H1299 cancer cell lysate, and 4) pulldown of z-THOR added to zebrafish embryo lysate. In all conditions pulldown of antisense THOR was utilized as a negative control. Two proteins, IGF2BP1 and IGF2BP3, were pulled down in all four conditions (FIG. 4A). The IGF2BP proteins were also the only proteins pulled down by h-THOR in both the nuclear and cytoplasmic fractions of H1299 cells (FIG. 11I). Both IGF2BP1 and IGF2BP3 have been reported to exhibit a cancer/testis expression pattern similar to that of THOR (Bell et al., Cell. Mol. Life Sci. CMLS 70, 2657-2675 2013) (FIG. 11 J,K).

Figure 4B:
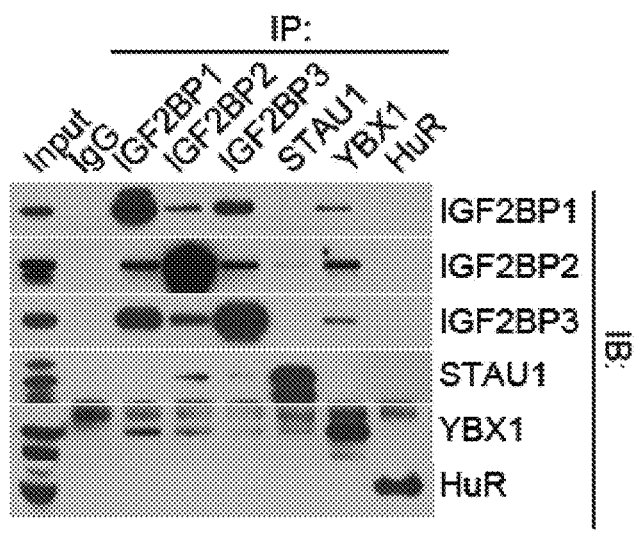
Figure 4C:
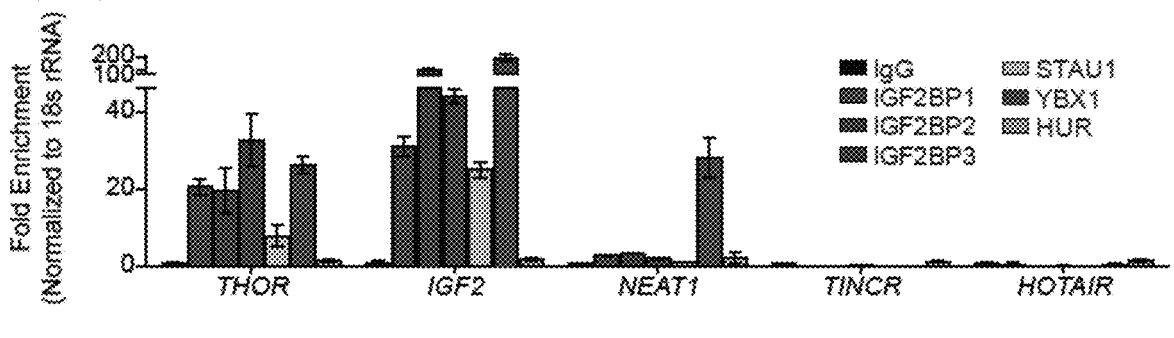

IGF2BP1 and IGF2BP3 have been implicated in mediating RNA-stability and translation through their binding to a number of well-defined mRNA targets (Bell et al., Cell. Mol. Life Sci. CMLS 70, 2657-2675 2013; Hafner et al., Cell 141, 129-141 2010). Additionally, this function has been documented to occur in concert with a number of other proteins comprising a messenger ribonucleoprotein (mRNP) complex (Weidensdorfer et al., RNA N. Y. N 15, 104-115 2009). It was observed that many members of this complex are also pulled down by THOR in the various conditions (FIG. 4A), and confirmed that IGF2BP1, IGF2BP2, IGF2BP3, and YBX1 are present in the complex via immunoprecipitation and Western blotting (FIG. 4B). To further validate the specificity of the interaction between h-THOR and mRNP complex proteins, RNA immunoprecipitation (RIP) assays were performed with antibodies against IGF2BP1-3, YBX1, STAU1 and HuR with subsequent qRT-PCR for THOR and a panel of additional control RNAs (FIG. 4C). Overexpression of THOR in H1437 cells was shown to produce a modest increase in the IGF2BP1 and IGF2BP3 interaction, demonstrated a role for THOR in mediating the mRNP complex formation (FIG. 11L).

Figure 4D:
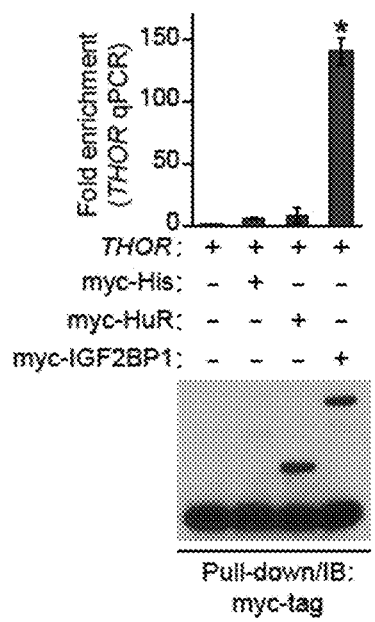

THOR and IGF2 RNAs were pulled down by the various proteins of the mRNP complex, while negative control lncRNAs NEAT1, TINCR, and HOTAIR exhibit a substantially reduced extent of pulldown (FIG. 4C). It was also observed that HuR, a protein not in the mRNP complex (FIG. 4B), does not to pull down any of the RNAs used in the study (FIG. 4C) despite robust pulldown confirmed via immunoblot (FIG. 4B). The relationship of THOR and IGF2BP1 was investigated as a direct binding interaction, showing that in vitro transcribed h-THOR and purified myc-tagged IGF2BP1 exhibit substantial binding compared to negative controls (FIG. 4D).

Figure 4E:
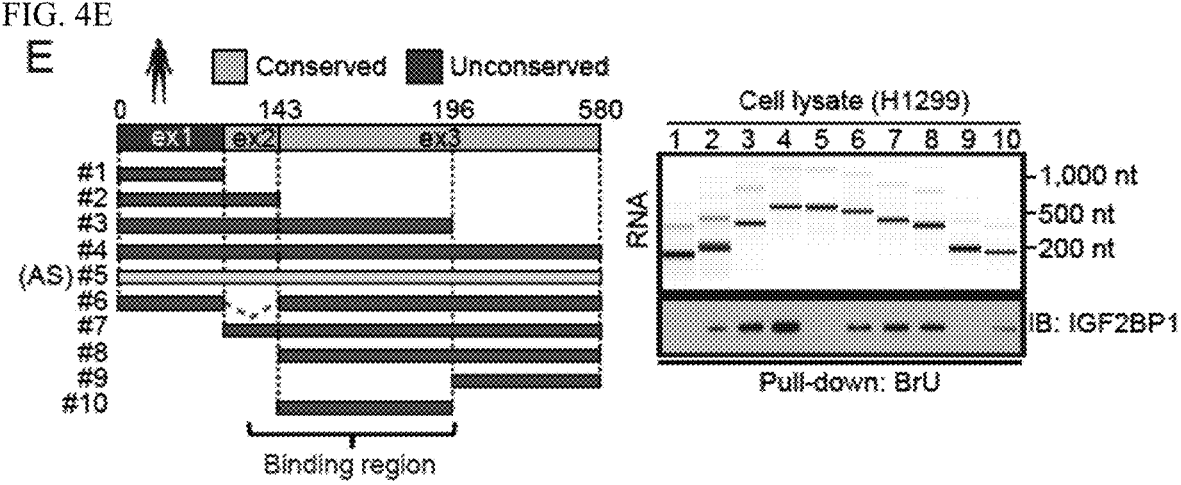
Figure 4F:
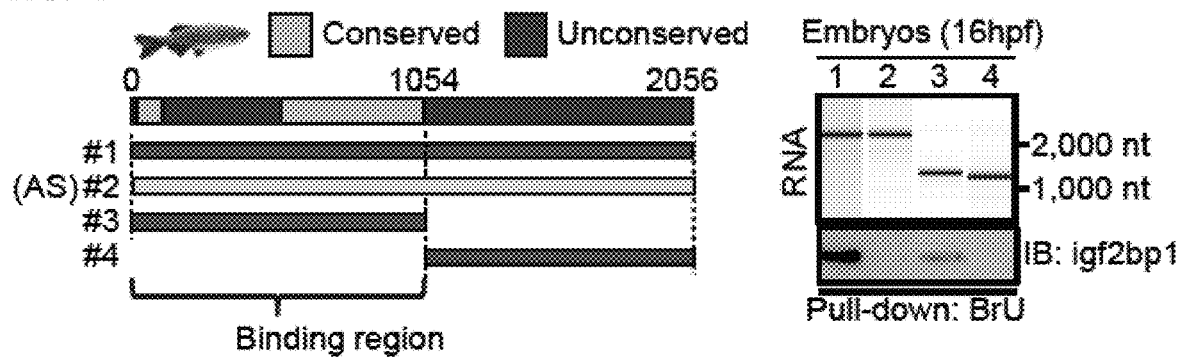

In order to further implicate that the conserved regions of THOR are responsible for its binding to IGF2BP1, indicated that this binding interaction was selected for evolutionarily, multiple deletion isoforms of both h-THOR and z-THOR were added to human H1299 cancer cell lysate and to zebrafish embryo lysate, respectively. Pulldown of the various isoforms of h-THOR followed by Western blot for IGF2BP1 revealed that the region of THOR responsible for IGF2BP1 binding is in exon 2 and 3, the conserved region of h-THOR (FIG. 4E). Additionally, this observation was also observed for z-THOR, wherein the 5' conserved portion of z-THOR was sufficient to result in pulldown of the zebrafish igf2bp1 protein (FIG. 4F).

The localization of binding interaction between THOR and IGF2BP1 on the IGF2BP1 protein was also interrogated. IGF2BP1 possesses 2 RNA recognition motif (RRM) domains and 4 K homology (KH) domains (FIG. 11M). Multiple recombinant deletion isoforms of IGF2BP1 were generated, and their ability to bind THOR was tested using RNA pulldown followed by Western blotting. Deletion of the RRM domains did not affect THOR binding, while the KH1, KH3, and KH4 domains were found to be essential for THOR binding (FIG. 11N).

THOR Regulates IGF2BP1's Target mRNAs Levels

Figure 5A:
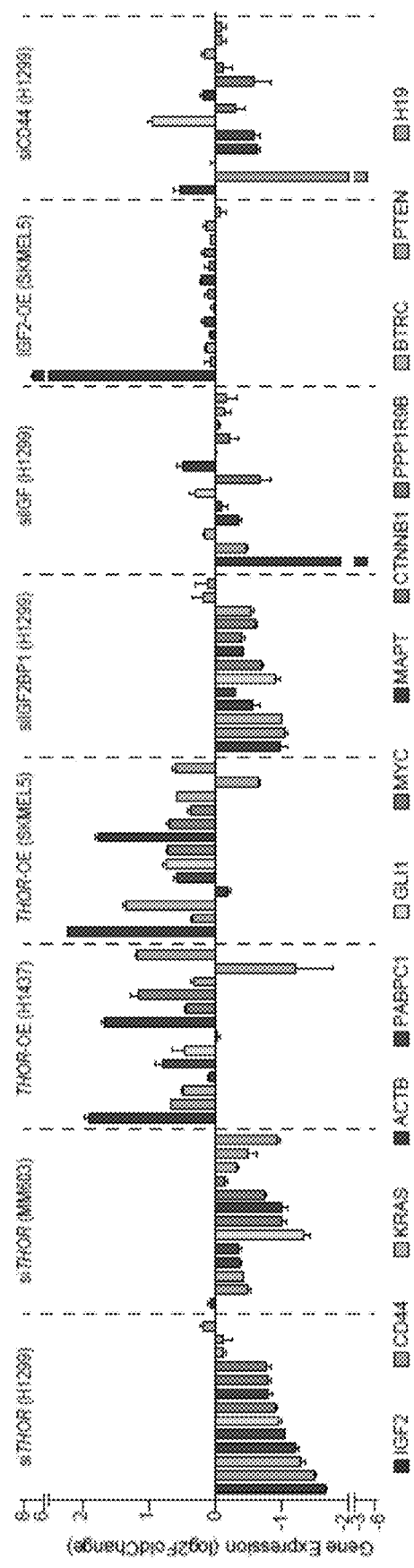
FIG. 5A-E. Interrogation of the functional relationship of THOR and IGF2BP1. A, Bar plot depiction of the expression levels of 13 canonical IGF2BP1 target genes by qRT-PCR in various conditions: THOR knockdown, THOR overexpression, IGF2BP1 knockdown, IGF2 knockdown, IGF2 overexpression, and CD44 knockdown. Data show mean±S.D. from one of the two independent experiments. B, qRT-PCR expression levels for IGF2 (red, black) and CD44 (blue, black) following RIP of IGF2BP1 or IgG as negative control. RIPs performed in H1299 cells under various experimental conditions: THOR siRNA knockdown, IGF2 siRNA knockdown, CD44 siRNA knockdown, and THOR overexpression. Asterisk indicate *P≤0.05; P≤0.01; *P≤0.001 by two-tailed Student's t-test. Data show mean±S.D. from one of the two independent experiments. C, qRT-PCR expression levels for IGF2 (top) and CD44 (bottom) following Actinomycin D treatment in THOR or LacZ overexpressing H1347 cells. Data show mean±S.D. from one of the two independent experiments. D, Cell proliferation assays for H1437 and SKMEL5 cells overexpressing LacZ control and THOR in the context of siRNA control and siRNA knockdown of IGF2BP1. Inset depicts the log 2(fold change) comparing the proliferation at the final time point for control and IGF2BP1 knockdown for the LacZ and THOR-overexpression settings. E, Cell proliferation assay in H1437 cells overexpressing full length THOR, a THOR deletion mutant lacking the IGF2BP1 binding site, and LacZ control. Asterisk indicate *P≤0.05; **P≤0.001 by two-tailed Student's t-test. Data show mean±S.E. from one of the two independent experiments.
Figure 5B:
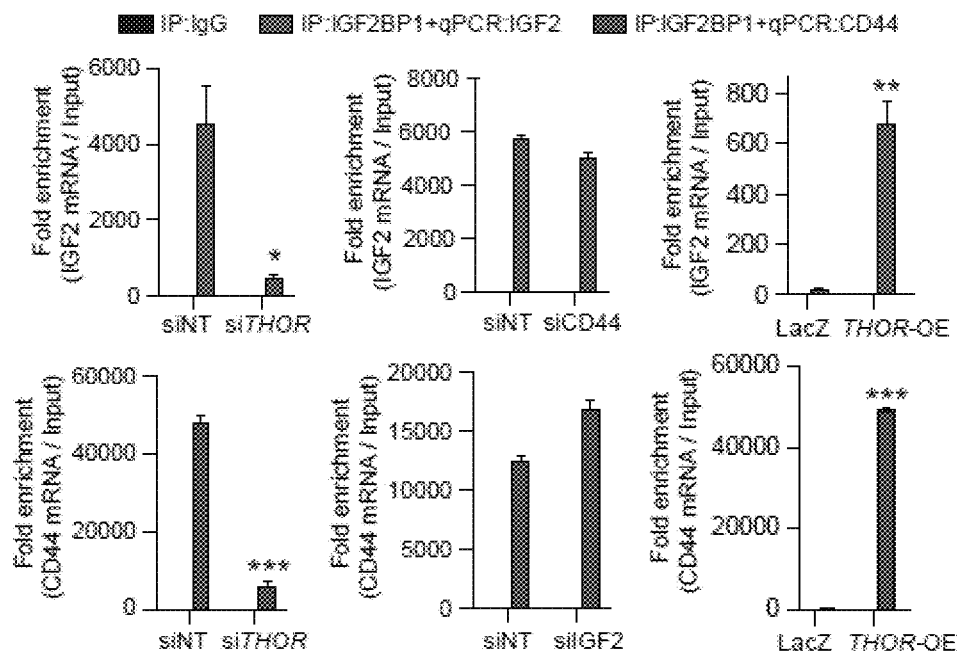
Figure 5C:
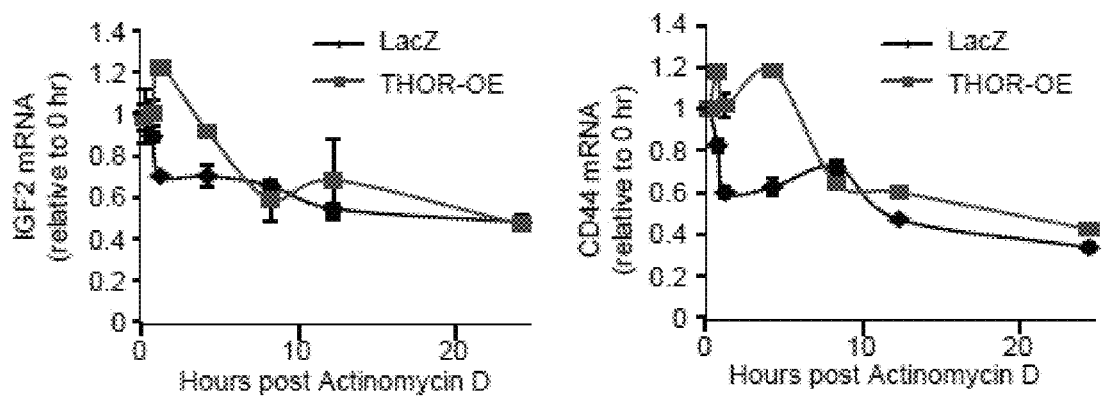
Figure 12A:
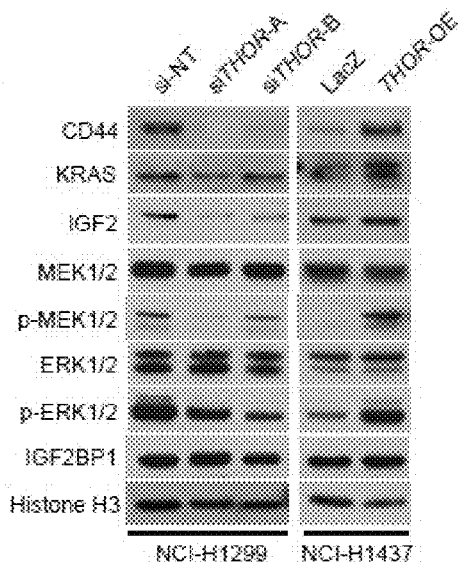
FIG. 12A-J. THOR interaction with IGF2BP proteins. A, The expression of IGF2BP1 targets and IGF2-MEK-ERK axis proteins and their corresponding phosphorylated forms in siTHOR treated H1299 cells (left) and THOR overexpressing H1437 cells (right). B, Bar plot depiction of the expression levels of 13 canonical IGF2BP1 target genes by qRT-PCR in H1299 cells with CRISPR-mediated THOR knockout, and in the same cells with expression of ectopic THOR. Data show mean±S.D. from one of the two independent experiments. C, Western blot confirming IGF2BP1 pull-down utilized for the RIP experiments depicted in FIG. 5C. D, qRT-PCR expression levels for GAPDH (left) and UBC (right) following Actinomycin D treatment in THOR or LacZ overexpressing H1347 cells. Data show mean±S.D. from one of the two independent experiments. E, qRT-PCR expression levels for THOR (red), GAPDH (blue) and MYC (green) following Actinomycin D treatment in H1299 cells. Data show mean±S.D. from one of the two independent experiments. F, Schematic diagram of the IGF2-MEK-ERK signaling cascade. G-H, Cell proliferation assay for cells treated with IGF2BP1 siRNA in (G) H1299 cells and (H) MM603. I-J, Anchorage-independent growth for cells with addition of non-targeting siRNA and siRNA targeting IGF2BP1 in (C) H1299 and (D) MM603 cells.
Figure 12B:
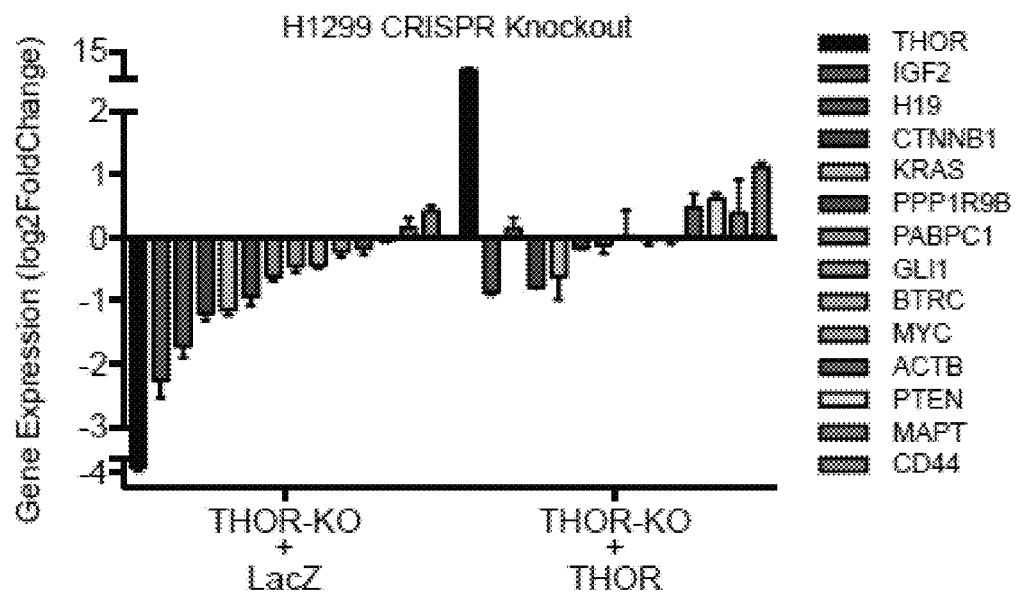
Figure 12C:
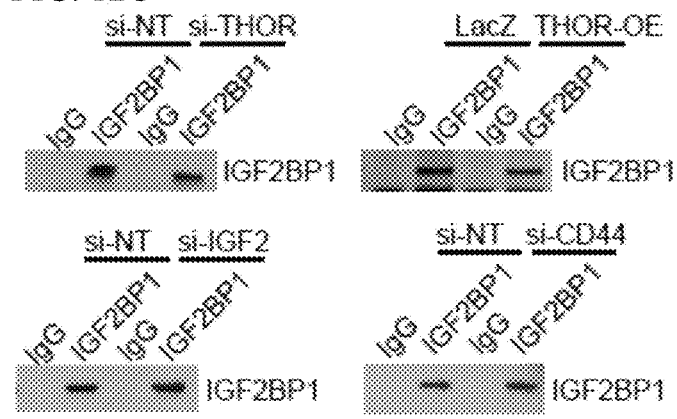
Figure 12D:
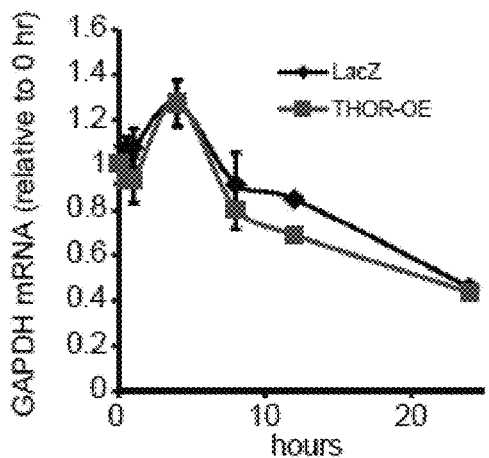
Figure 12D:
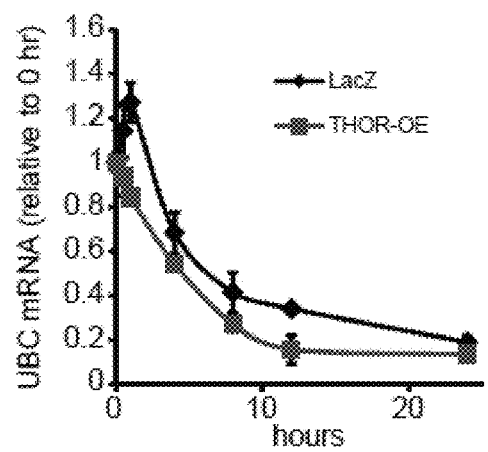
Figure 12E:
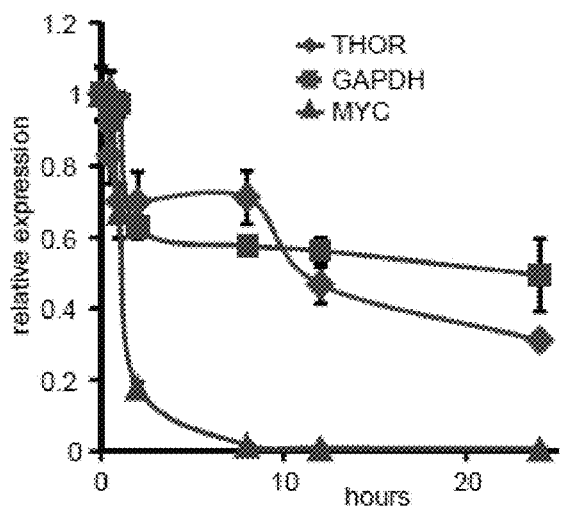
Figure 12F:
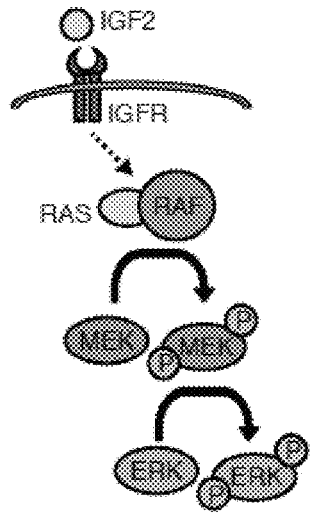
Figure 12G:
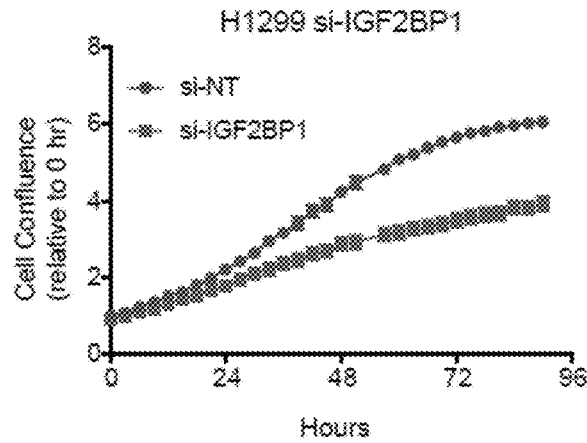
Figure 12H:
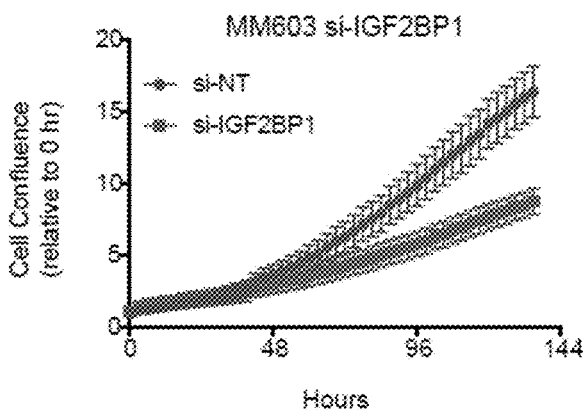

Having identified a specific and evolutionarily conserved interaction between THOR and IGF2BP1, this functional relationship was further characterized. As IGF2BP1 has been reported to regulate the mRNA stability of a set of well-described target RNAs (Bell et al., 2013; supra; Hammerle et al., 2013; supra), it was hypothesized that THOR may be playing a role in IGF2BP1-facilitated mRNA stabilization. To test this hypothesis, the levels of canonical IGF2BP1 targets (IGF2, CD44, KRAS, ACTB, PABPC1, GLI1, MYC, MAPT, CTNNB1, PPP1R9B, BTRC, PTEN and H19) (Bell et al., 2013; supra) were measured in various conditions. The levels of nearly all IGF2BP1 targets were decreased upon knockdown of THOR in both H1299 and MM603 cells, and conversely increased with stable overexpression of THOR in H1437 and SKMEL5 cells (FIG. 5A and FIG. 12A). Knockdown of IGF2BP1 produced a similar reduction in its targets, while altering levels of IGF2 and CD44, two of the canonical IGF2BP1 targets, failed to show a trend in the expression of IGF2BP1 targets (FIG. 5A). This finding was confirmed in CRISPR-mediated THOR knockout H1299 cells, displaying a similar reduction of expression of IGF2BP1 targets. Additionally, a reversal of this phenotype was observed when expressing ectopic THOR in these cells, demonstrating a trans function for THOR (FIG. 12B). IGF2BP1 binds to target mRNAs, and has been shown to mostly increase their stability (Bell et al., 2013; supra; Weidensdorfer et al., RNA N. Y. N 15, 104-115 2009), although there has been a report of an IGF2BP1-mediated destabilization effect (Hammerle et al., Hepatology 58, 1703-1712 2013). Thus, it was hypothesized that the effects of THOR levels on IGF2BP1 targets (FIG. 5A) may be explained by THOR stabilizing the interaction of IGF2BP1 with its targets. To examine this function, qRT-PCR for IGF2BP1 targets, IGF2 and CD44, following IGF2BP1 RIP was performed. Knockdown of THOR reduced binding of both IGF2 and CD44 to IGF2BP1, while overexpression of THOR increased IGF2 and CD44 binding. However, knockdown of IGF2 did not result in an altered binding of CD44 to IGF2BP1, while CD44 knockdown failed to cause an effect of IGF2 binding to IGF2BP1 (FIG. 5B and FIG. 12C). Further corroborating this hypothesis, THOR overexpression substantially increased the mRNA stability of IGF2BP1 targets IGF2 and CD44 following Actinomycin D treatment (FIG. 5C), while having no effect on the stability of the GAPDH and UBC, two control mRNAs that do not interact with IGF2BP1 (FIG. 12D). The THOR mRNA has a half-life of 14 hours (FIG. 12E), which is longer than the dynamic range observed for the stabilization effects on IGF2 and CD44 (FIG. 5C and FIG. 12D), confirming THOR is present in cells long enough to exert these effects.

Figure 5D:
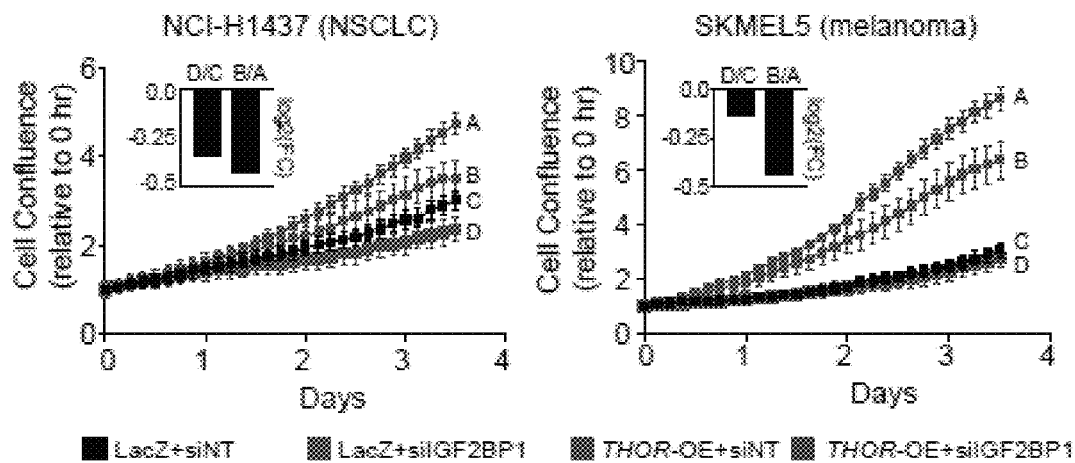
Figure 5E:
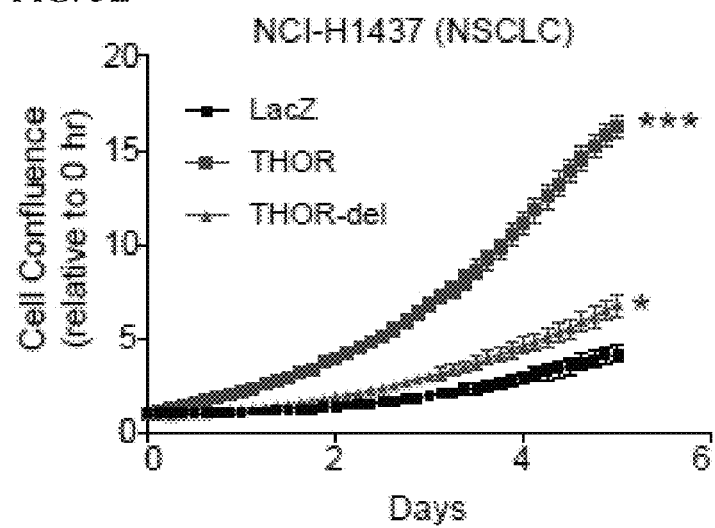
Figure 12I:
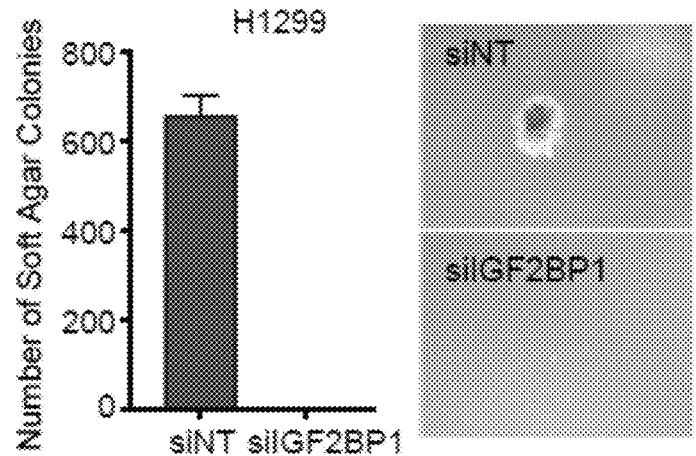
Figure 12J:
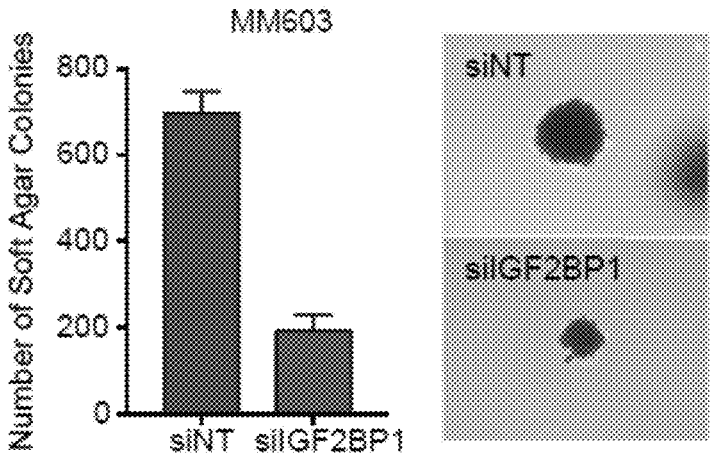

IGF2, one of the canonical IGF2BP1 targets from which it derives its name (Nielsen et al., Mol. Cell. Biol. 19, 1262-1270 1999), is a secreted protein that has been shown to contribute to oncogenesis via mitogenic activation through receptor tyrosine kinase-MEK-ERK signaling (El-Shewy et al., J. Biol. Chem. 282, 26150-26157 2007; Livingstone, Cancer 20, 321-339 2013). It was observed that in addition to altering levels of IGF2 (FIG. 5A) and modulating IGF2-IGF2BP1 binding (FIG. 5B), THOR is also successful in regulating the downstream signaling pathway of IGF2 (FIG. 12A,F), showing that the THOR-mediated changes in IGF2BP1 target expression are sufficient to result in functional downstream signaling. Additionally, the proliferative advantage conferred by THOR overexpression was abrogated by reduction of IGF2BP1 levels in those cells, with a particularly striking phenotype in the SKMEL5 cell line (FIG. 5D), further corroborating the functional relevance of the THOR-IGF2BP1 interaction. Additionally, knockdown of IGF2BP1 in both H1299 and MM603 cells reduced cell proliferation (FIG. 12 G,H) and soft agar colony formation (FIG. 12I,J). Overexpression of a deletion construct of THOR lacking the conserved IGF2BP1 binding sequence failed to exhibit the enhanced proliferation observed with full length THOR overexpression (FIG. 5E). These data indicate that the binding interaction between THOR and IGF2BP1 leads to functionally relevant consequences in cells that have implications for the oncogenicity of THOR.

Figure 13A:
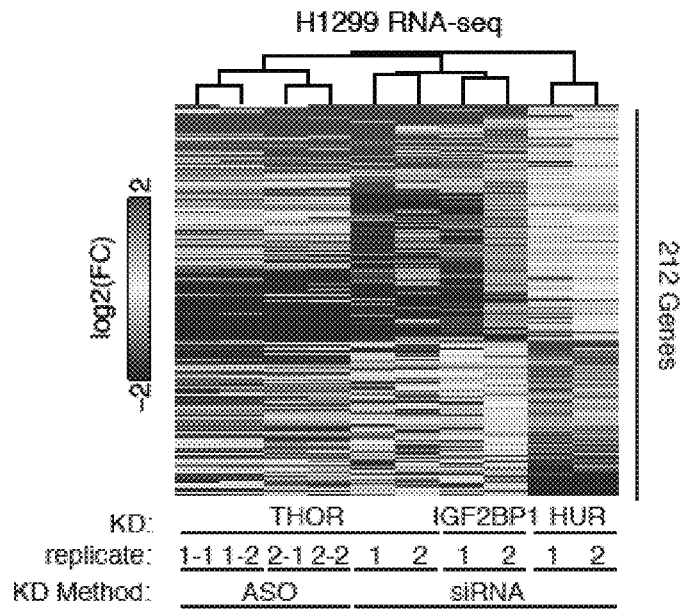
FIG. 13A-J. RNA-seq analysis of THOR function. A, Heatmap depicting the expression of the genes significantly differentially expressed (DESeq FDR<0.05) in knockdown of THOR and IGF2BP1 in H1299 cells via siRNA in addition to those genes with significant differential expression in HUR knockdown via siRNA. B,C, Scatterplot depicting the GSEA performance for MSigDBv5.0 gene signatures with NES<0 for (B) HUR and THOR and (C) HUR and IGF2BP1. Signatures significant upon knockdown of both genes (FWER p-value <0.01) depicted in gold. D, Genomic depiction of THOR. Coverage plots for IGF2BP1 replicates shown for H1437 cells overexpressing THOR and LacZ control (blue). GENCODEv24 gene structure of THOR also shown (green). Peaks called via Piranha for all three iCLIP samples shown (bottom). E-F, Gene expression depicted as log 2(Fold Change) from RNA-seq data comparing the THOR-overexpression condition to LacZ overexpression. Genes identified as IGF2BP1 binding partners via iCLIP are depicted in blue, while all other genes in yellow. Expression differences shown via (E) density plot and (F) cumulative distribution function. G, Coverage plots for IGF2BP1 binding via iCLIP for H1299. H-I, Gene expression depicted as log 2(Fold Change) from RNA-seq data comparing the THOR knockdown to control knockdown in H1299 cells. Genes identified as IGF2BP1 binding partners via iCLIP are depicted in blue, while all other genes in yellow. Expression differences shown via (H) density plot and (I) cumulative distribution function. J, Scatterplot depiction of the RNA-seq expression of genes in the genomic vicinity of THOR.
Figure 13B:
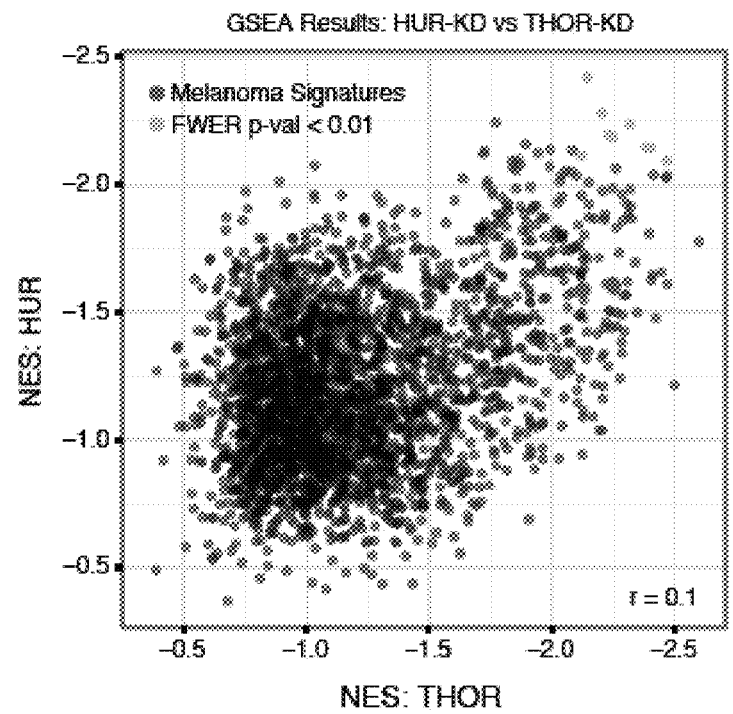
Figure 13C:
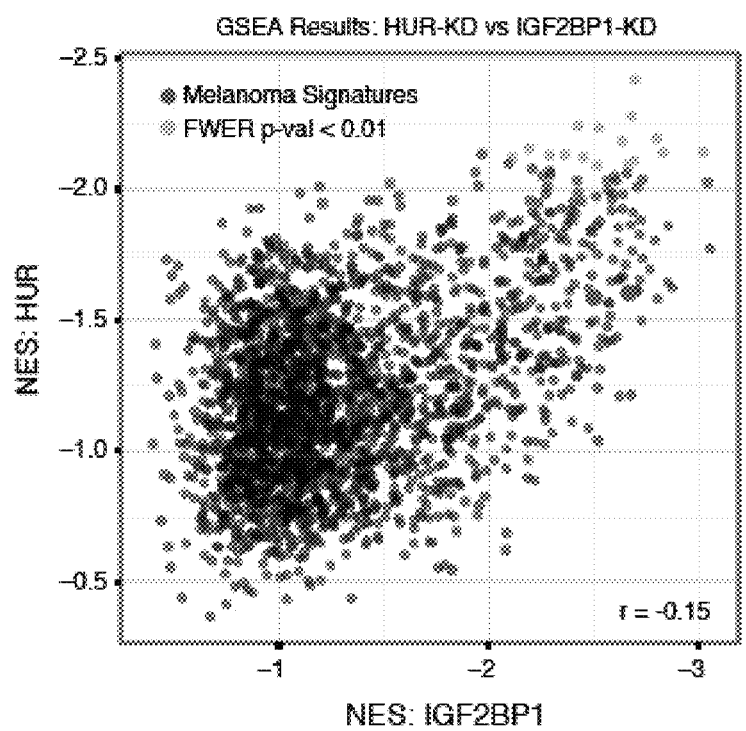
Figure 13D:
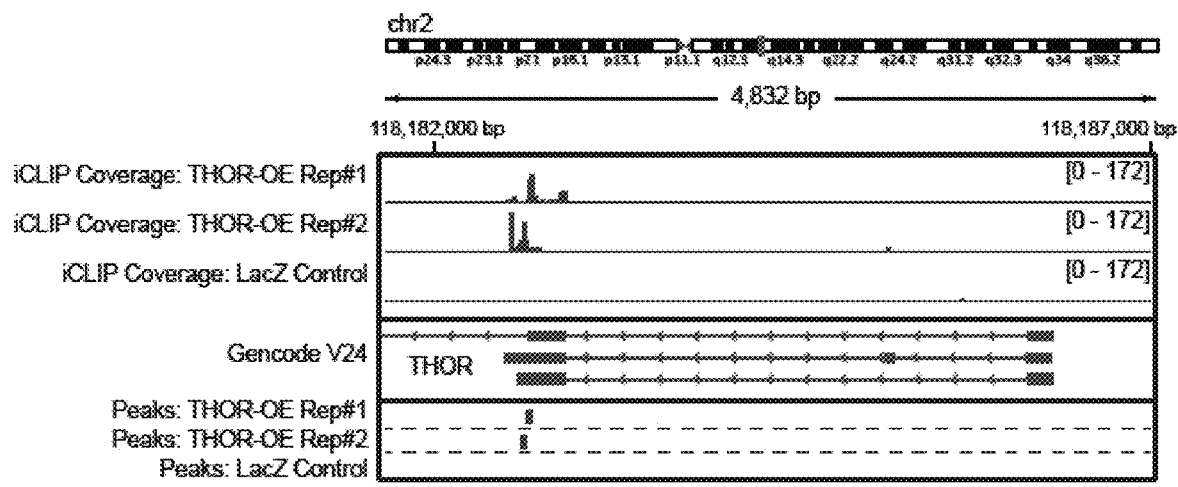
Figure 13E:
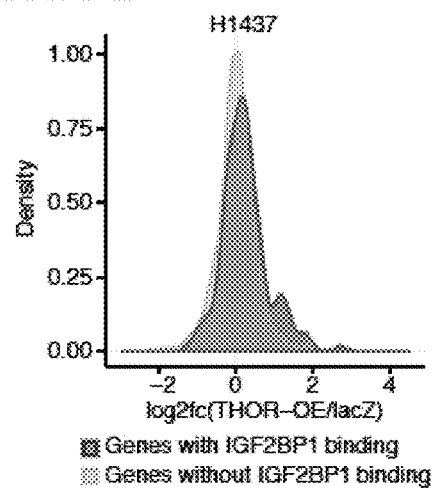
Figure 13F:
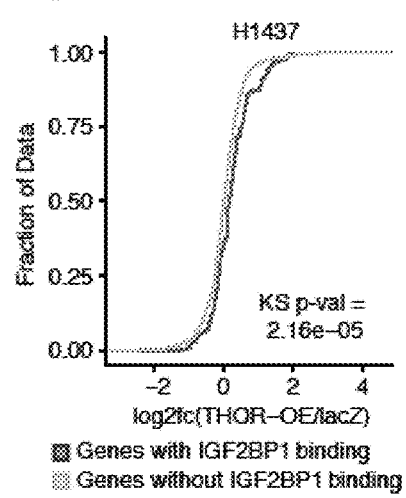

To more broadly assess the transcriptional phenotype of THOR-knockdown in comparison to IGF2BP1-knockdown, differential expression was assessed for RNA-seq performed with two independent siRNAs targeted to THOR, IGF2BP1, and HUR. Providing further evidence for a shared functional role for THOR and IGF2BP1, significant overlap between the genes with significant differential expression upon THOR and IGF2BP1 knockdown was observed (FIG. 6A,B). Knockdown of THOR produced gene expression changes in many more genes than did knockdown of IGF2BP1, demonstrating a potential functional role of THOR beyond that mediated through IGF2BP1. Corroborating that the observed gene expression changes via siRNA knockdown are on-target effects, knockdown of THOR via two independent ASOs produced gene expression changes in line with those produced via siRNA knockdown (FIG. 13A). As a negative control, the transcriptional changes upon knockdown of HUR that failed to exhibit a similar differential expression profile to that of THOR and IGF2BP1 knockdown was demonstrated. The gene signatures most altered upon knockdown of THOR and IGF2BP1 were also highly concordant when comparing GSEA (Subramanian et al., Proc. Natl. Acad. Sci. U.S.A 102, 15545-50 2005) analyses upon gene expression changes following knockdown (Pearson r=0.50; FIG. 6C). The gene signature changes following HUR knockdown, however, were not correlated to those following either THOR (FIG. 6C) or IGF2BP1 (FIG. 6C) knockdown. Two independent gene signatures associated with metastasis and relapse of melanoma (Kauffmann et al., Oncogene 27, 565-573 2007; Winnepenninckx et al., J. Natl. Cancer Inst. 98, 472-482 2006) were among the top gene signatures altered upon knockdown of both IGF2BP1 and THOR (FIG. 6C), further implicating the THOR-IGF2BP1 relationship in cancer progression, particularly in melanoma.

Figure 13G:
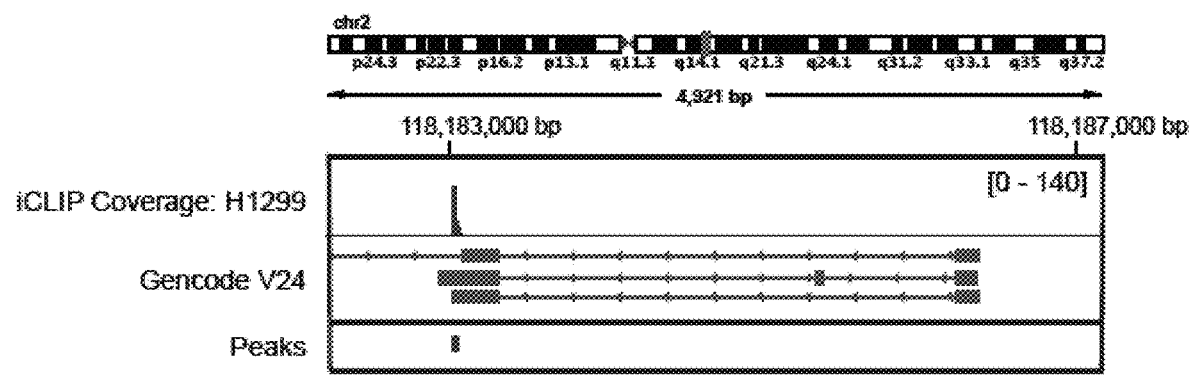
Figure 13H:
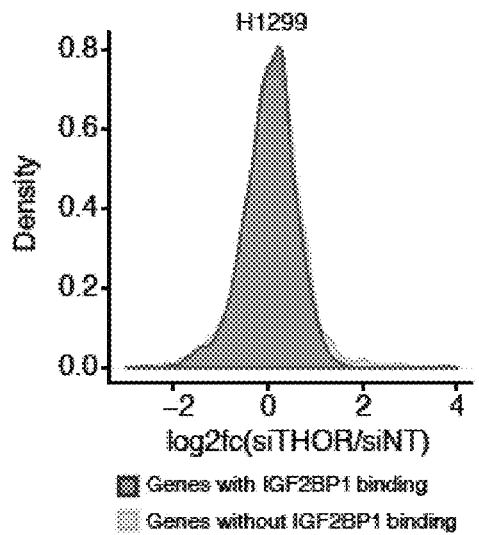
Figure 13I:
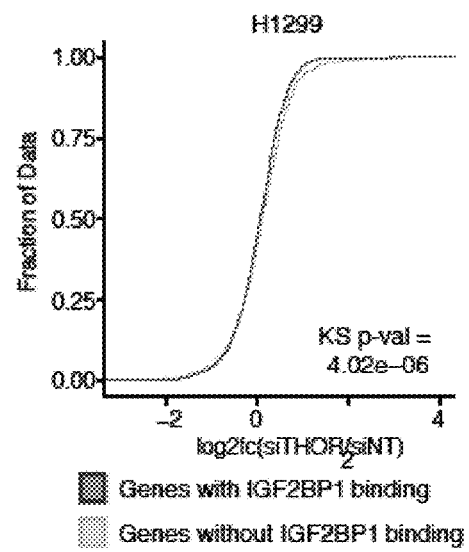
Figure 13J:
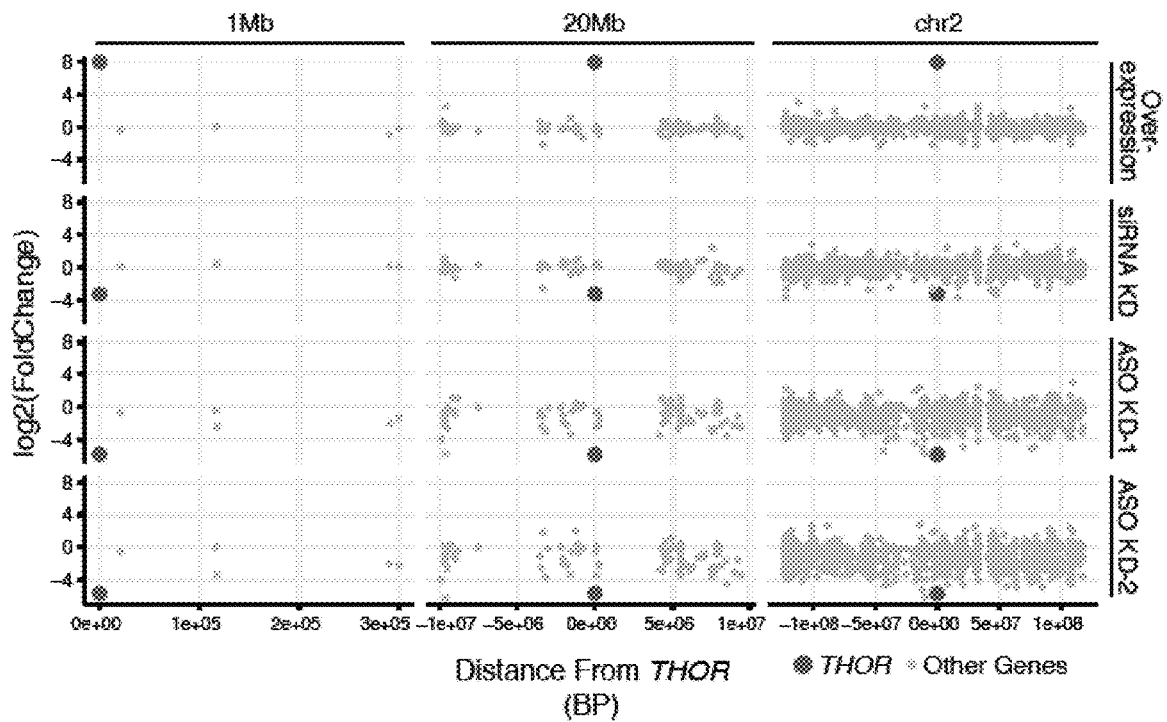

To further implicate a functional relationship of THOR and IGF2BP1, iCLIP was performed on IGF2BP1 in H1437 cells overexpressing THOR. Binding of IGF2BP1 on THOR was observed in the same region identified via deletion construct pulldowns (FIG. 4D), while no binding was observed in the H1437 cells overexpressing the LacZ control (FIG. 13D). 185 genes were identified as IGF2BP1 binding targets via iCLIP, and RNA-sequencing was also performed on to interrogate gene expression changes for these genes bound to IGF2BP1. In the context of THOR overexpression, those genes identified as IGF2BP1 targets were observed to have a significant increase in expression compared to genes that are not IGF2BP1 targets (FIG. 13 E, F). Additionally, iCLIP was performed in H1299 to interrogate IGF2BP1 in the context of endogenous THOR expression. IGF2BP1 binding to THOR was identified as in H1437 cells (FIG. 13G). Additionally, as identified in the THOR overexpression context above, those genes identified as binding targets of IGF2BP1 in the H1299 iCLIP experiment exhibited a significant reduction in expression upon THOR knockdown when compared to those genes without IGF2BP1 binding, although the magnitude of effect was lesser than in the H1437 experiment (FIG. 13 H, I). These data provide a high-throughput corroboration of the potential effects of THOR in mediating RNA-stability of IGF2BP1 targets. Further leveraging these data, cis function for THOR was ruled out by the finding that genes near THOR do not exhibit gene expression changes upon modulation of THOR levels (FIG. 13J).

Figure 7A:
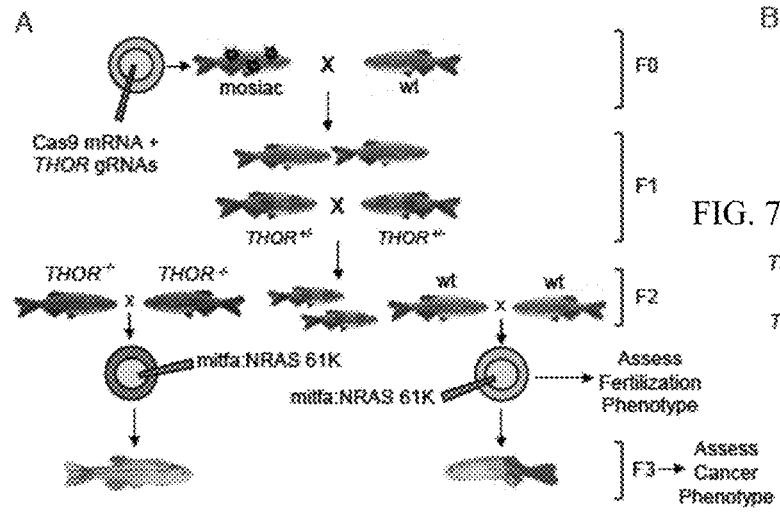
FIG. 7A-J. THOR regulates melanoma onset in zebrafish. A, Schematic depicting creation of THOR knockout zebrafish model. B, Fraction of fertilized zebrafish embryos derived from wild-type, or THOR knockout zebrafish (−/−) 6 hours following mating. Asterisk (*) indicates P≤0.01 by a $\chi 2$ test. Data show mean±S.D. from two independent experiments. C, Fraction of fertilized 6 hpf zebrafish embryos derived from wild-type female crossed with THOR knockout male, or THOR knockout female crossed with wild-type male. Asterisk (*) indicates P≤0.01 by a $\chi 2$ test. Data show mean±S.D. from two independent experiments. D, Expression levels of zTHOR in testicular somatic cells as well as in six Hoechst profiled subpopulations of testicular germ cells. Data show mean±S.D. E, Bar plot demonstrates expression of 12 zebrafish orthologs of the canonical IGF2BP1 target genes by qRT-PCR in zebrafish embryos. Expression represented as log 2 of the fold change of either THOR$^{-/-}$ compared to wild-type embryos (red) or THOR overexpression compared to control mCherry. Data show mean±S.D. from one of the two independent experiments. F, Kaplan-Meier curve of melanoma free period for mitfa promoter driven NRAS 61K zebrafish in either THOR$^{-/-}$ background or wildtype background. P values were determined using a log-rank test. G, Schematic describing the generation of the h-THOR overexpression melanoma zebrafish model. H, Kaplan-Meier curve of melanoma free period for p53−/− zebrafish co-injected with either mitfa promoter driven NRAS 61K+mitfa promoter driven human THOR or mitfa promoter driven NRAS 61K+mCherry. P values were determined using a log-rank test. I, Percentage of body area covered in melanoma for mCherry and h-THOR injected zebrafish also containing mitfa promoter driven NRAS 61K. Asterisk (*) indicates P≤0.01 obtained by a two-tailed Student's t-test. J, Specimen example of NRAS 61K driven melanomas in zebrafish co-injected with mitfa promoter driven h-THOR or mitfa promoter driven mCherry in a p53$^{-/-}$ background.
Figure 8C:
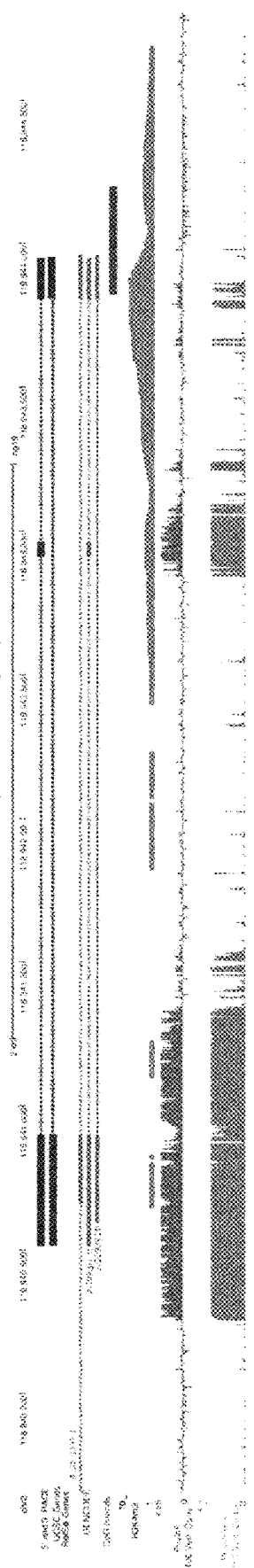
Figure 8C:
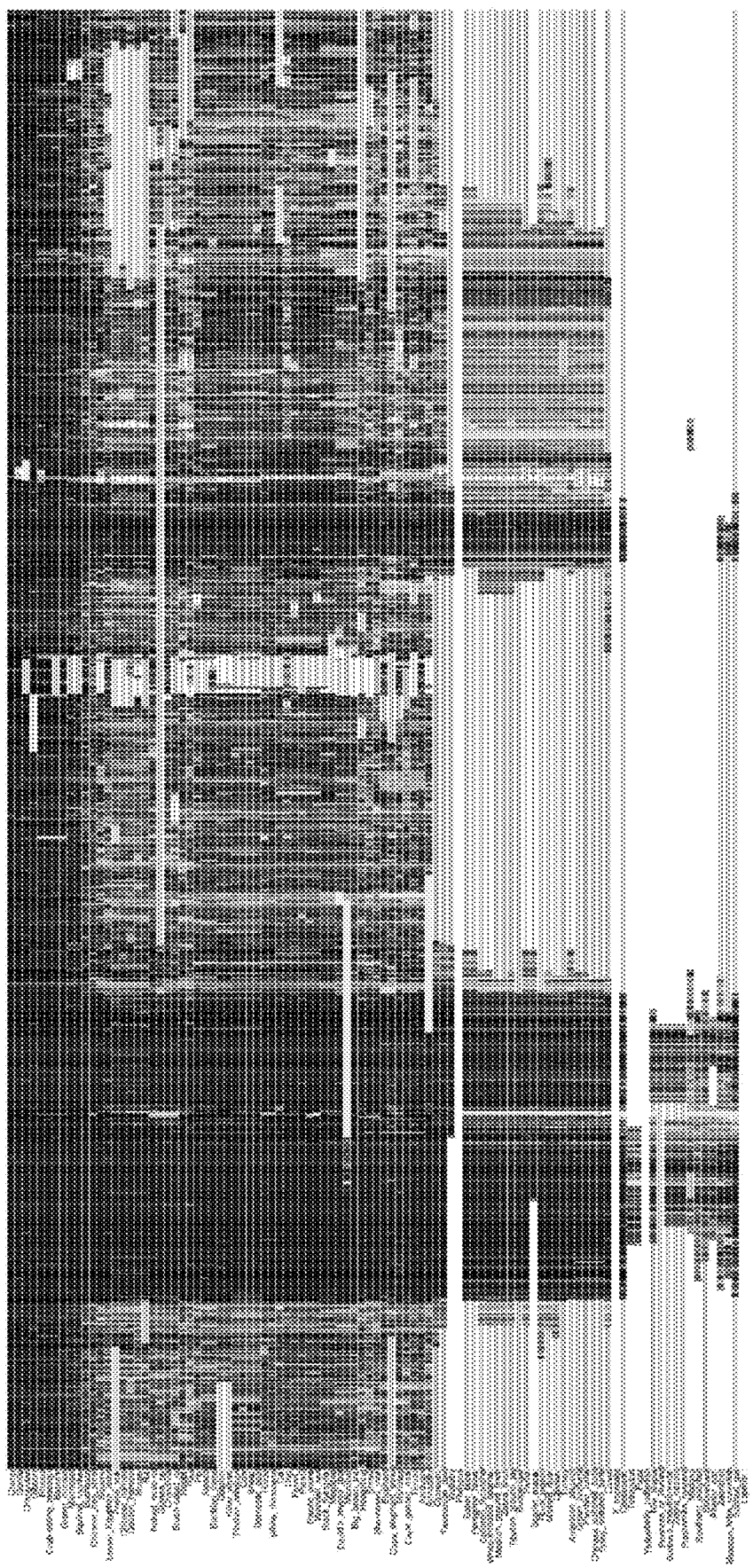
Figure 8D:
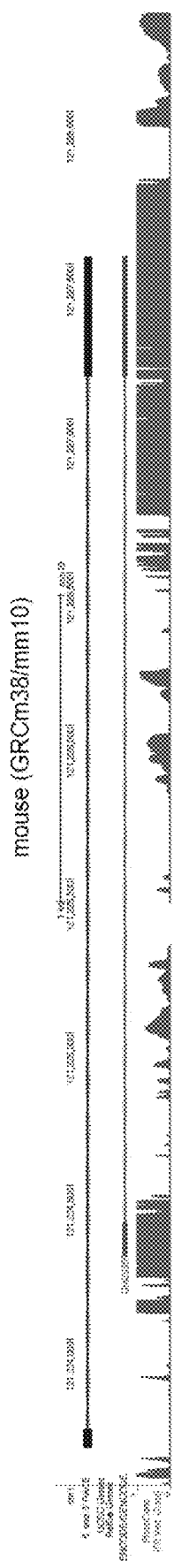
Figure 8E:
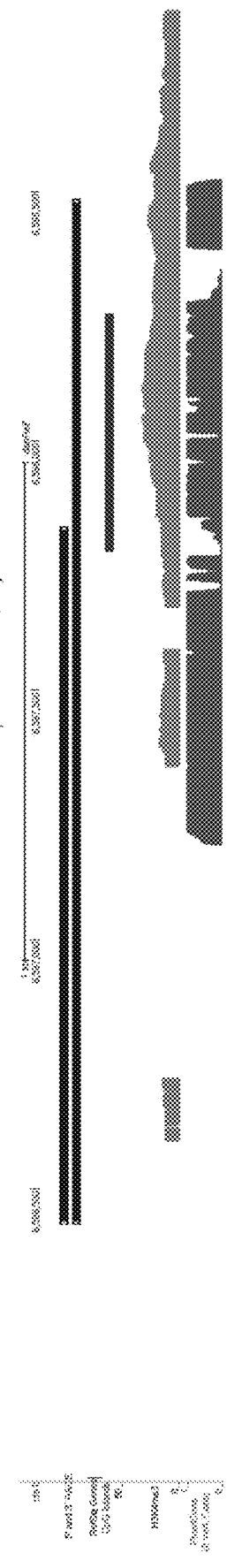
Figure 14A:
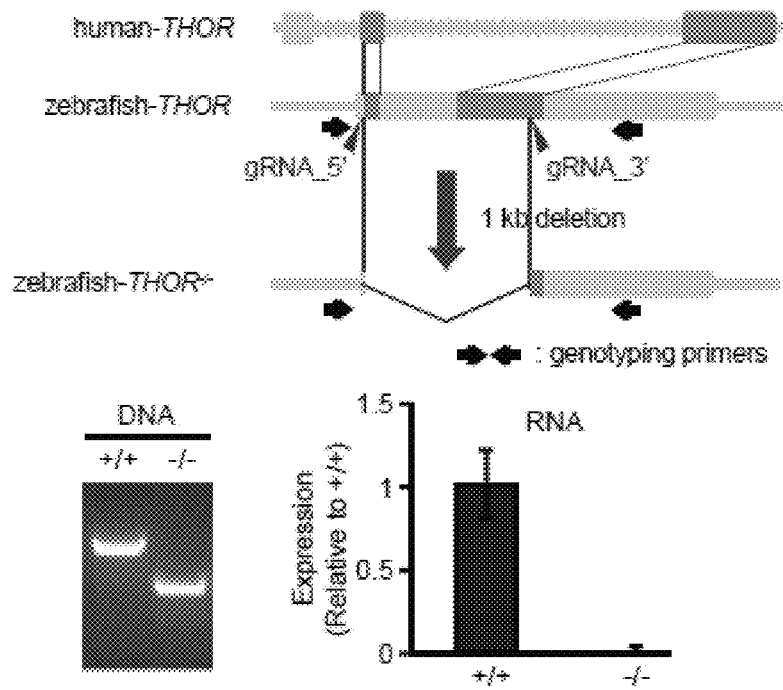

THOR Knockout Zebrafish Exhibit Fertilization Defects and Resistance to Melanoma Formation Given that sequence conservation of THOR (FIG. 1A,B, D, and FIG. 8C-E, a conserved tissue expression pattern (FIG. 2A,C,D), and conservation of its binding interaction to IGF2BP1 (FIG. 4A,E,F) were observed, its potential function in a different animal model was investigated, extending the implications of its functionality beyond human cancer cell lines (FIG. 3 and FIG. 4). The zebrafish animal model has become a commonly used system for investigation of development (Giraldez et al., Science 308, 833-838 2005; Ulitsky et al., Cell 154, 26-46 2011), and more recently it has become a relevant model system for cancer investigation (Lieschke and Currie, Nat. Rev. Genet. 8, 353-367 2007). With the advent of CRISPR-Cas genome editing technology (Cong et al., 2013; surpa), the genomes of model organisms can be molded to interrogate specific genomic questions with ease (Hwang et al., Nat. Biotechnol. 31, 227-229 2013; Sanchez-Rivera and Jacks, Nat. Rev. Cancer 15, 387-395 2015). Thus, utilizing the CRISPR-Cas9 genome editing system, a THOR knockout zebrafish line was generated. Firstly, two sgRNAs targeting the conserved region of z-THOR (FIG. 14A) and Cas9 mRNA were injected into zebrafish embryos, producing a mosaic F0 generation that was subsequently mated to wildtype zebrafish to generate heterozygous F1 offspring (THOR$^{+/-}$). The heterozygotes were then mated with one another to generate a population of homozygous THOR knockout zebrafish (THOR$^{-/-}$) in the F2 generation (FIG. 7A).

Figure 7B:
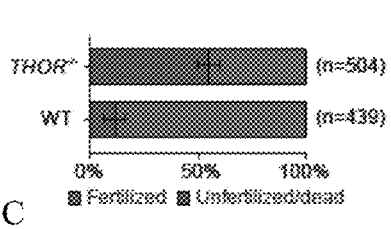
Figure 7C:
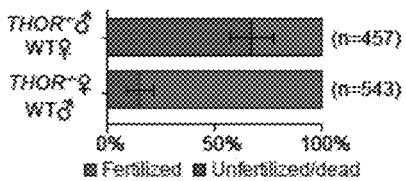
Figure 7D:
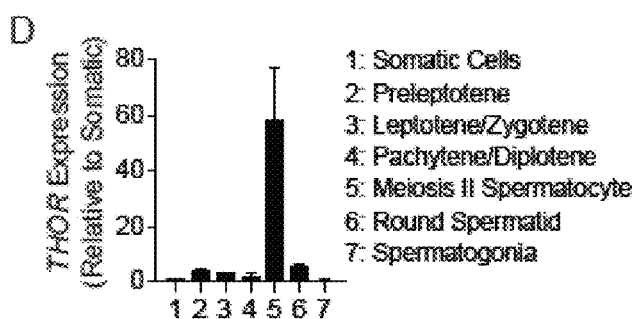
Figure 14B:
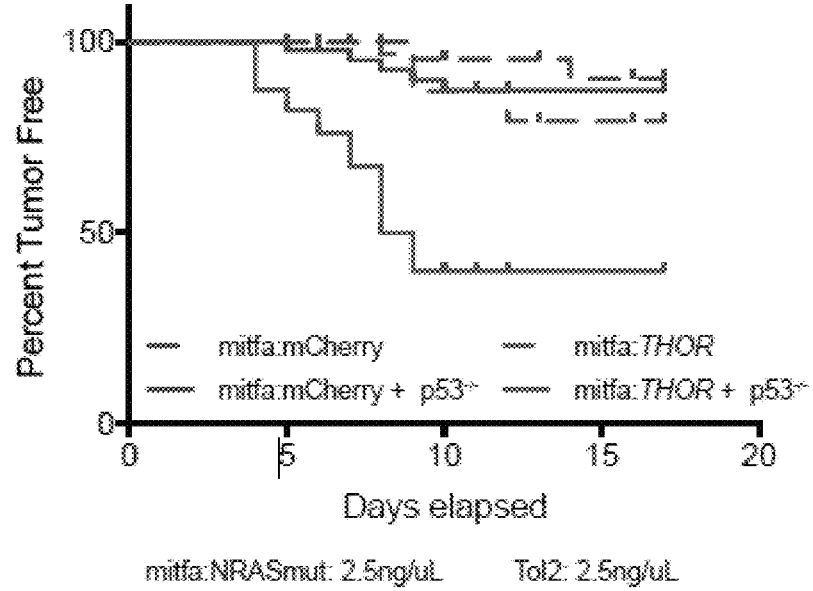
Figure 14C:
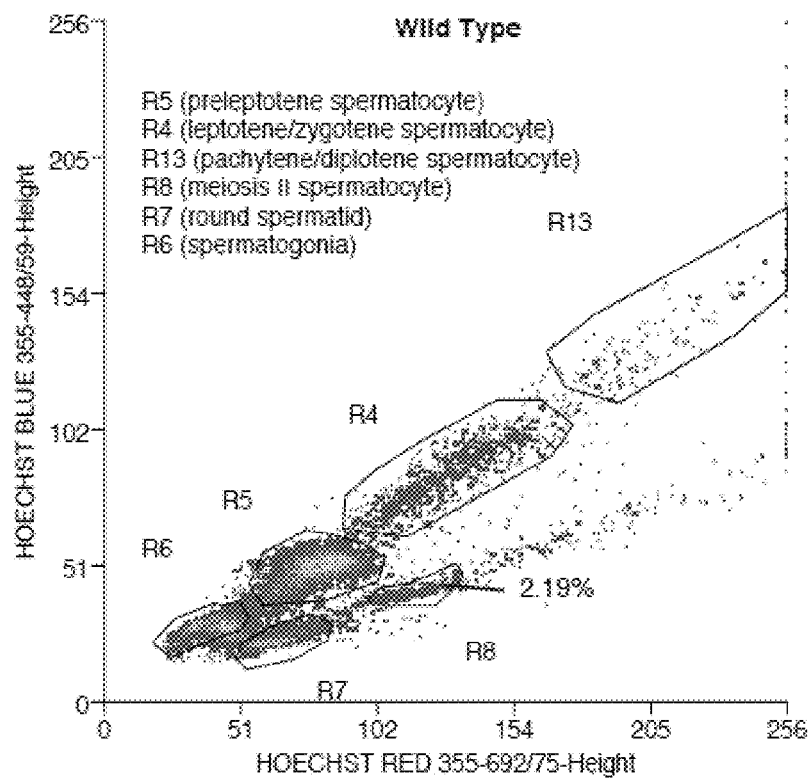
Figure 14D:
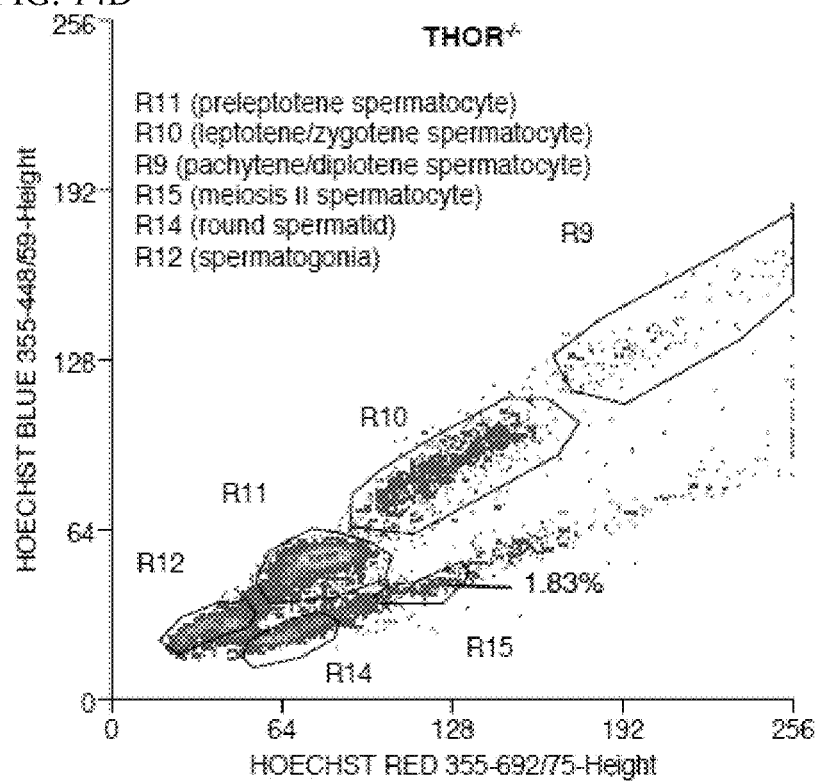
Figure 14E:
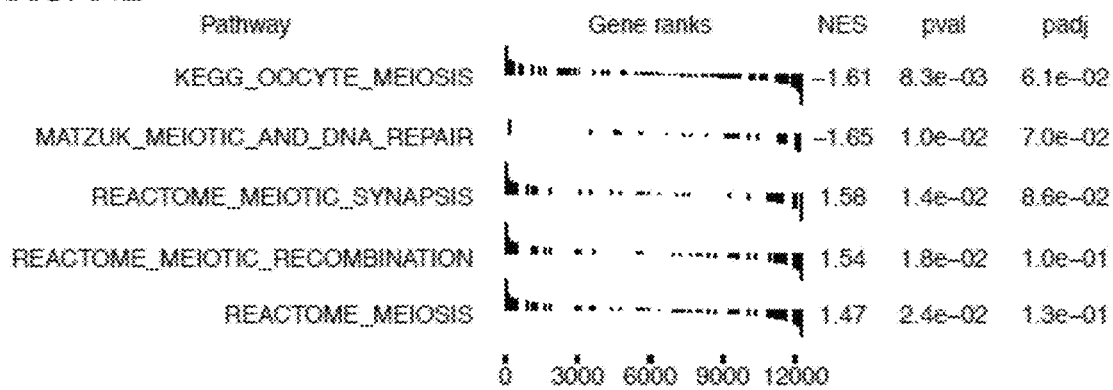
Figure 14F:
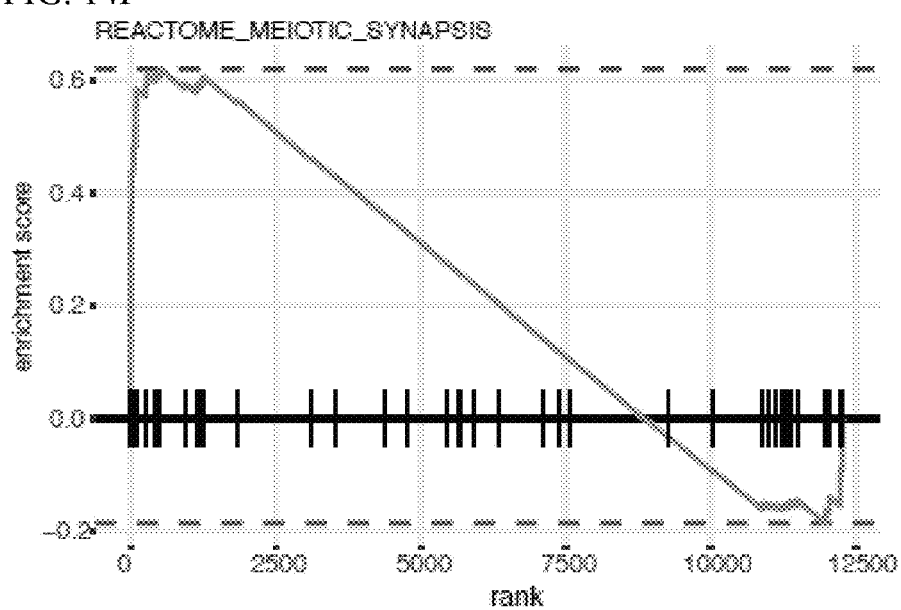
Figure 14G:
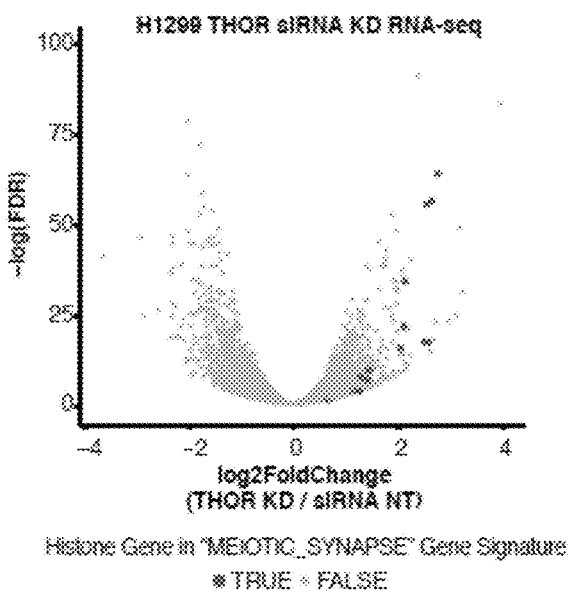

Upon generation of THOR$^{-/-}$ zebrafish, a striking phenotypic effect on the fertility of THOR$^{-/-}$ zebrafish in comparison to wildtype zebrafish was observed, with 55% of embryos from mating of THOR$^{-/-}$ zebrafish either dead or unfertilized 6 hours post fertilization (hpf), compared to only 11% from wildtype mating (FIG. 7B). Moreover, when mating wildtype males to female THOR$^{-/-}$ zebrafish, the fertilization defect was substantially diminished, while mating wildtype females to male THOR$^{-/-}$ zebrafish produced a significant fertilization defect in the zebrafish offspring (FIG. 7C). This finding supports the role of THOR in the testis, and suggests a primary functional role in fertility for THOR in the testis. When assessing the subpopulations of sperm at various stages of development, expression of THOR was found to be isolated to spermatocytes in meiosis II at much higher levels than sperm at any other stage of development (FIG. 7D) and testis of THOR$^{-/-}$ zebrafish contained fewer cells in meiosis II compared to wildtype zebrafish (FIG. 14 C, D). Of note, GSEA performed on siRNA THOR knockdown RNA-seq (FIG. 6C and FIG. 13 B,C) revealed a significant association of THOR expression with all meiosis signatures found within MSigDB v5 (FIG. 14, E, F). Upon THOR knockdown, genes involved in meiotic pathways were significantly upregulated. Within these signatures, a striking preponderance of upregulation in histone genes involved in meiosis was observed. Many of these meiotic histone genes were identified as some of the most positively dysregulated genes upon THOR knockdown (FIG. 14G).

Figure 7E:
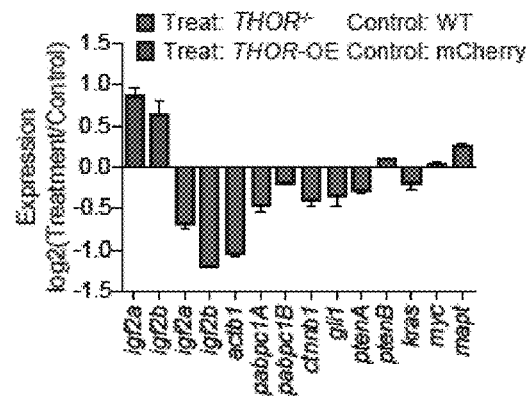

Having shown a shared role transcriptional modulation for THOR and IGF2BP1 in human cancer cell lines, shared gene expression changes in the zebrafish model were investigated, observing a significant decrease in the expression of IGF2BP1 targets in THOR$^{-/-}$ zebrafish embryos compared to wildtype embryos, and a significant increase of igf2a and igf2b in zebrafish embryos ectopically overexpressed h-THOR (FIG. 7E). Additionally, given that the transcriptional changes resulting from THOR and IGF2BP1 knockdown exhibited strong association with previously identified melanoma gene signatures, the oncogenicity of THOR was investigated using a zebrafish melanoma model wherein driver genes are injected into zebrafish to elicit various cancer phenotypes (Langenau et al., Oncogene 27, 4242-4248 2008).

Figure 7F:
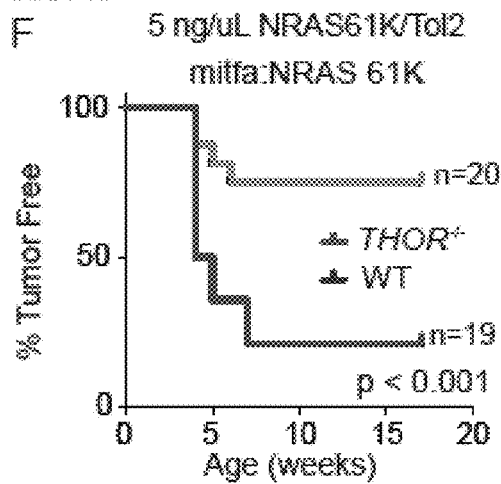

Specifically, a previously described zebrafish melanoma model that employs embryonic injection of human NRAS-K61 driven by the mitfa promoter (a zebrafish gene expressed in melanocytes) resulting in the formation of easily visible zebrafish melanoma (FIG. 7A) (Dovey et al., Zebrafish 6, 397-404 2009) was used. The zebrafish melanoma model is different from that previously reported in the modality of transgenesis. In the previous model, naked DNA containing NRAS61K was injected into single cell zebrafish embryos containing a mutant p53 background (Dovey et al., 2009; supra). The naked DNA transgenesis model is largely inefficient and requires mating of transgenic zebrafish to the F1 generation for successful generation of the transgenic fish, which can negatively impact transgenesis that can be deleterious to animal viability. Here, a Tol2 integration system which has been shown to produce markedly more robust transgenesis (Kwan et al., Dev. Dyn. Off. Publ. Am. Assoc. Anat. 236, 3088-3099 2007) was used. In addition to the more robust integration of the NRAS transgene, this system enables generation of a mosaic F0 generation that can be utilized in functional experimentation. The timeframe of transcription and translation of the transposase injected into the embryos is longer than the time to replication of the single cell embryo, resulting in mosaic expression of the transgene in the adult zebrafish. This phenomenon circumvents the selection against particularly stressful transgenic events in the naked DNA model, enabling robust expression of NRAS61K in these Tol2 mediated transgenic zebrafish. Using this NRAS melanoma system, a striking resistance to melanoma development in the THOR$^{-/-}$ zebrafish was observed (FIG. 7F). Of note, while the previous NRAS61K model of zebrafish melanoma required a p53 mutant background for tumorigenesis, tumor growth in p53 wildtype zebrafish was observed after injection of a high amount of NRAS61K/Tol2 into the single cell embryo (5 ng/uL). The ability to generate tumors in a p53 wildtype context is likely due to the F0 mosaicism and to the increased efficiency of transgenesis of the Tol2 system. The fertilization defect and resistance to melanoma mediated by THOR present compelling evidence for a conserved role of THOR in vertebrate physiology and pathophysiology.

Human THOR Enhances the Onset of Melanoma in Zebrafish

Figure 7G:
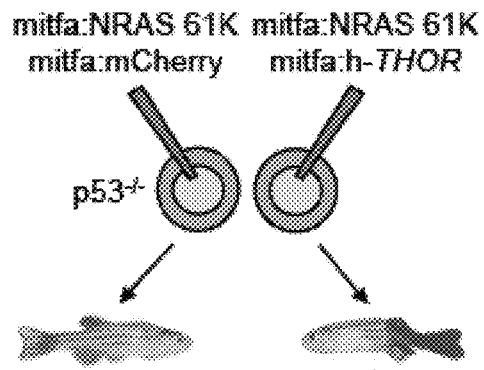
Figure 7H:
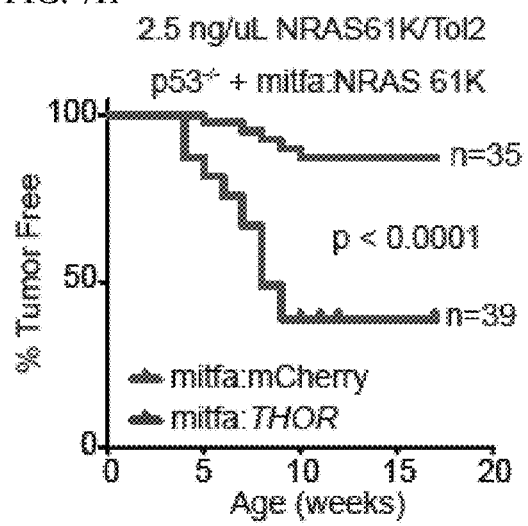
Figure 7I:
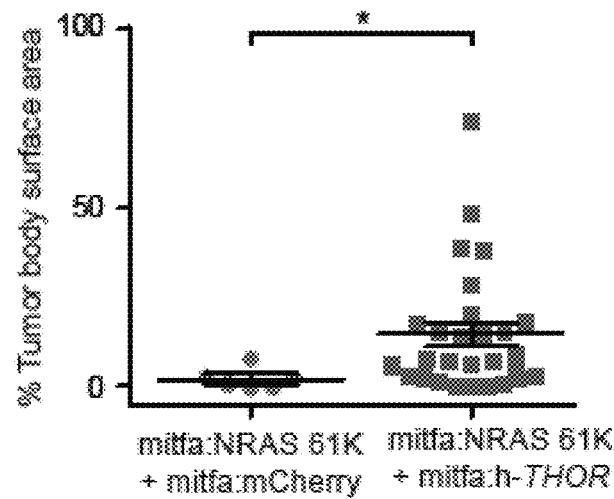
Figure 7J:
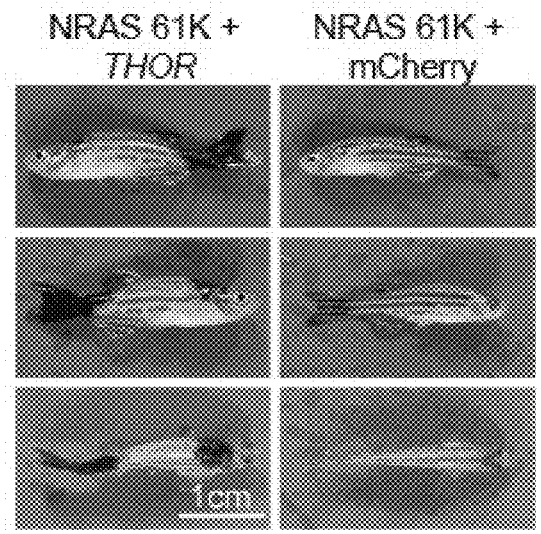

In order to further investigate the role of THOR in zebrafish melanoma development, the function of the addition of human THOR to zebrafish embryos utilizing the mitfa-promoter driven injection method with injection of mCherry used as a negative control was performed (FIG. 7G) (Langenau et al., 2008; supra). Injection was performed on p53 knockout (p53$^{-/-}$) zebrafish to enhance the melanoma phenotype observed, as previously described (Dovey et al., 2009; supra). In this model, embryos were injected with a lower concentration of NRAS61K/Tol2 (2.5 ng/uL) than the THOR knockout model (FIG. 7A,F), resulting in a more indolent phenotype (FIG. 7H), despite the loss of p53. Nevertheless, it was shown that loss of p53, in the context of THOR overexpression significantly reduces tumor-free survival (FIG. 14B). The overexpression of h-THOR in zebrafish was sufficient for a significant increase in not only the onset of melanoma development (FIG. 7H), but also on the size of the melanoma tumors that developed (FIG. 7I, J). NRAS 61K induced melanomas in both p53$^{-/-}$ and wildtype zebrafish (FIGS. 7J and 14 I, K) were positive for Melan-A staining, a mitf target gene and marker for melanoma in human specimens confirming that the lesions were in fact melanoma (FIG. 14J, L). Thus, the striking ability of the human isoform of THOR to promote melanoma in zebrafish argues for an evolutionarily conserved role of THOR in mediating cellular processes that are potentially involved in tumor development.

TABLE 1

| chrom | start | end | maxlength | tcat (tucp = transcript of unknown coding potential) | reference_name | mitranscriptome_name |
|---|---|---|---|---|---|---|
| chr1 | 44969848 | 45026990 | 56307 | lncrna | NA | KCCAT40 |
| chr1 | 98389009 | 98515563 | 26545 | lncrna, tucp | MIR137HG, RP11-272L13.3 | MIR137HG |
| chr1 | 143644576 | 143750106 | 5416 | lncrna, tucp | LINC00875, RP6-206I17.3, LINC01138, RP6-206I17.1 | OVAT215 |
| chr1 | 149576502 | 149577300 | 705 | lncrna, tucp | RP11-277L2.3 | OVAT12 |
| chr1 | 200311566 | 200453140 | 16675 | lncrna, mixed_read_through, protein_coding | LINC00862, ZNF281 | HICLINC26 |

TABLE 1-continued

| chrom | start | end | maxlength | tcat (tucp = transcript of unknown coding potential) | reference_name | mitranscriptome_name |
|---|---|---|---|---|---|---|
| chr1 | 200380708 | 200452674 | 5107 | lncrna | EU250746, RP11-469A15.2 | KCCAT533 |
| chr1 | 244172879 | 244220780 | 8373 | lncrna, mixed_read_through, protein_coding | RP11-278H7.1, ZBTB18, LOC339529, AK310634 | HICLINC32 |
| chr10 | 38092552 | 38108477 | 15925 | lncrna | NA | CAT1248 |
| chr10 | 77001895 | 77121872 | 5532 | lncrna | ZNF503-AS1 | ZNF503-AS1 |
| chr10 | 77220957 | 77275854 | 20332 | lncrna | NA | HICLINC242 |
| chr10 | 77294696 | 77378177 | 46237 | lncrna | NA | HICLINC243 |
| chr10 | 77552200 | 77599462 | 46408 | lncrna | AL731568.1 | KCCAT544 |
| chr10 | 103459280 | 103489889 | 5784 | lncrna | RP11-190J1.3 | CAT1297 |
| chr10 | 104106019 | 104116259 | 6598 | lncrna | MIR_584 | HICLINC250 |
| chr10 | 130452758 | 130494912 | 13203 | lncrna | NA | HICLINC259 |
| chr11 | 119768522 | 119826605 | 8007 | lncrna | NA | HNCAT224 |
| chr12 | 22852032 | 23356838 | 18523 | lncrna | AK094733, RP11-114G22.1, RP11-449P1.1, RP11-153K16.1 | HICLINC274 |
| chr12 | 54101956 | 54150729 | 15635 | lncrna, mixed_read_through, protein_coding | CALCOCO1, CISTR-ACT | LGAT88 |
| chr13 | 97999250 | 98026479 | 27229 | lncrna | RNA5SP37 | HICLINC295 |
| chr14 | 36349494 | 36705454 | 19108 | lncrna, mixed_read_through, pseudogene | RP11-317N8.4, BRMS1L, RP11-116N8.1, LINC00609, RP11-259K15.2 | CAT1653, LINC00609 |
| chr14 | 36738267 | 36742582 | 1211 | lncrna | NA | HICLINC304 |
| chr14 | 50249312 | 50338400 | 8843 | lncrna, mixed_read_through, protein_coding | NEMF, METAZOA_SRP, RN7SL3 | KHCAT459 |
| chr15 | 35837850 | 36341917 | 3178 | lncrna | DPH6-AS1, RP11-684B21.1 | DPH6-AS1 |
| chr15 | 37396029 | 37402163 | 5987 | lncrna | NA | HICLINC318 |
| chr15 | 95869090 | 96051292 | 3747 | lncrna | LINC00924 | LINC00924 |
| chr16 | 54304911 | 54333259 | 10945 | lncrna, tucp | NA | CAT1854 |
| chr16 | 54885553 | 54964563 | 13236 | lncrna | CRNDE | CAT1855, CRNDE |
| chr16 | 72459846 | 72569836 | 7095 | lncrna | AC004158.3, AK095618 | CAT1871 |
| chr16 | 73092989 | 73096990 | 2413 | lncrna | RP11-346C20.3 | HICLINC335 |
| chr18 | 39041057 | 39212203 | 9553 | lncrna | RP11-142I20.1, KC6 | LSCAT30 |
| chr18 | 53346311 | 53540358 | 15142 | lncrna | RP11-397A16.1 | CAT2020 |
| chr18 | 53440321 | 53464004 | 13719 | lncrna | AK127787, RP11-397A16.2 | HICLINC356 |
| chr18 | 53670978 | 53859225 | 7403 | lncrna | RP11-456O19.4, RP11-456O19.5, LOC100505474, CTD-2008L17.2 | CAT2021 |
| chr18 | 73926337 | 73938535 | 11083 | lncrna | RP11-94B19.1 | HICLINC362 |
| chr2 | 19165588 | 19558440 | 10815 | lncrna, mixed_read_through | AC092594.1, OSR1 | CAT215 |
| chr2 | 25450706 | 25455918 | 5067 | lncrna, tucp | NA | HICLINC40 |
| chr2 | 60781023 | 60783714 | 2420 | lncrna | NA | CAT245 |
| chr2 | 60898696 | 60965989 | 1947 | lncrna, pseudogene | RP11-416L21.2 | HICLINC50 |
| chr2 | 66654202 | 66959175 | 15117 | lncrna, mixed_read_through | AC007392.3, MEIS1 | HICLINC53 |
| chr2 | 105022724 | 105035698 | 4799 | lncrna | AC068535.2 | CAT284 |
| chr2 | 105315691 | 105322361 | 5627 | lncrna | AC068057.1 | PRCAT310 |
| chr2 | 118940511 | 118944639 | 2100 | lncrna | AC093901.1 | HICLINC62 |
| chr2 | 144386688 | 144667222 | 9863 | lncrna | AC092652.1, RP11-434H14.1 | LACAT234 |
| chr2 | 156840544 | 157111546 | 22110 | lncrna, tucp | AC093375.1, BC032407 | LSCAT223 |
| chr2 | 157192442 | 157224262 | 9962 | lncrna, tucp | NA | HICLINC71 |
| chr2 | 157582258 | 157599808 | 11646 | lncrna | NA | HICLINC73 |
| chr2 | 177293899 | 177690269 | 23452 | lncrna | AC017048.4 | CAT339 |
| chr2 | 177475747 | 177505108 | 13894 | lncrna, tucp | RP11-324L17.1, AC017048.3 | CAT338 |
| chr2 | 219933448 | 219940404 | 5849 | lncrna | NA | HICLINC86 |
| chr20 | 20950791 | 20955373 | 3417 | lncrna | RP5-1177M21.1 | LGAT73 |
| chr20 | 21068793 | 21073177 | 3741 | lncrna | NA | LGAT90 |
| chr20 | 21206871 | 21224948 | 18077 | lncrna | NA | THCAT569 |

TABLE 1-continued

| chrom | start | end | maxlength | tcat (tucp = transcript of unknown coding potential) | reference_name | mitranscriptome_name |
|---|---|---|---|---|---|---|
| chr20 | 22509221 | 22559600 | 11882 | lncrna | LINC00261 | LINC00261 |
| chr20 | 29507940 | 29554859 | 20944 | lncrna | RP4-610C12.4, RP4-610C12.3 | PRCAT186 |
| chr21 | 17442467 | 18018743 | 9992 | lncrna | LINC00478, AP000473.8, AP000473.5 | LINC00478 |
| chr21 | 17663062 | 17682186 | 5305 | lncrna | AP001172.2 | HICLINC384 |
| chr21 | 17905940 | 17949011 | 6191 | lncrna | AP000962.2 | CAT2192 |
| chr3 | 52584100 | 52596258 | 12158 | lncrna | RNU6ATAC16P | AMAT96 |
| chr3 | 114034977 | 114108032 | 8763 | lncrna | ZBTB20-AS1 | CAT434 |
| chr3 | 114812496 | 114825853 | 5199 | lncrna | ZBTB20-AS4 | ZBTB20-AS4 |
| chr3 | 181132104 | 181162548 | 5313 | lncrna | RP11-275H4.1 | LGAT79 |
| chr3 | 181916542 | 182131010 | 23537 | lncrna | NA | CAT477 |
| chr3 | 188651106 | 188667032 | 10698 | lncrna | TPRG1-AS1 | TPRG1-AS1 |
| chr4 | 41872093 | 41893020 | 4422 | lncrna | RP11-457P14.5, BC025350, LINC00682 | LINC00682 |
| chr4 | 54738988 | 54876128 | 16468 | lncrna | RP11-89B16.1 | CAT547 |
| chr5 | 87830417 | 87907735 | 6814 | lncrna | LINC00461 | LINC00461 |
| chr5 | 87960173 | 87987573 | 10449 | lncrna | LINC00461 | LINC00461 |
| chr5 | 91726221 | 92275609 | 12050 | lncrna, pseudogene | CTC-529L17.2, CTC-458G6.2, CCT7P2, RP11-133F8.2 | CAT691 |
| chr5 | 139028390 | 139059331 | 29236 | lncrna | CTD-3224K15.2 | HICLINC139 |
| chr5 | 141201511 | 141258811 | 13854 | lncrna, protein_coding | PCDH1 | HICLINC142 |
| chr5 | 175848245 | 175861702 | 2235 | lncrna | NA | HNCAT169 |
| chr6 | 50059498 | 50071660 | 2441 | lncrna | RP11-397G17.1 | HICLINC150 |
| chr6 | 108439973 | 108480892 | 4361 | lncrna | OSTM1-AS1 | OSTM1-AS1 |
| chr6 | 156241778 | 156310880 | 37387 | lncrna | MIR1202 | BRCAT280 |
| chr7 | 26623027 | 26904974 | 11311 | lncrna, protein_coding | SKAP2 | HICLINC169 |
| chr8 | 28894032 | 29127341 | 15757 | lncrna, protein_coding | KIF13B | HICLINC185 |
| chr8 | 77315031 | 77437350 | 6168 | lncrna | RP11-706J10.1, RP11-706J10.3 | HICLINC201 |
| chr8 | 99999693 | 100013023 | 3873 | lncrna | AC104986.1 | HICLINC207 |
| chr8 | 130886169 | 130934817 | 29107 | lncrna | RP11-473O4.4 | THCAT385 |
| chr9 | 96327492 | 96338734 | 10823 | lncrna, tucp | AL353629.1 | CAT1166 |
| chr9 | 109040241 | 109465042 | 2376 | lncrna, tucp | RP11-308N19.1, AK093363, RP11-308N19.4 | MEAT55 |
| chrX | 41092072 | 41095828 | 3545 | lncrna | NA | HICLINC387 |

TABLE 2

| Species | Sequence | SEQ ID NO.: |
|---|---|---|
| Human | AGCCGAGTTCGCGCCGCCGGTAGGTGCTGCC ATGCCAGGGGGCGGGATCGTGGAGCGCCTCG CAGAACCGCACGAAAGCAAAACAAAGCCAT CTCTCCGGAGCAGAAATAGAACAGACGTGGC CGGGGAAAGCCAAATATTTCCTGCCGTCCTG GTGAACACAATCGACAAGGCAGTGAAGCAA ACATCATTAGGTGGCTGGACTCAGACACATC ACGCTCCAGTTTGGGTTCCAAGGTGCTTCTC TCTGGATTTTCACCTGCCTTGCCAAAAATGA TTGATTACGCTGGGCCAACTGGGTGTCCGGC AATACCCAACAAATGACTTTGGCCCCTAACA GCAGGTCTTGGCCAGACAGAAATCAATATTT CACCATTAAAATCTATCAAAGAAGAGTTAAG GCACCATCTGTCCCTGCCGCCTCTCTATGGT GTGTGAACATTAAATCCGACACTTGTACTAC ATGGGTAATCAATATATAGGTTCACAGAT CATTTGTGGTTCCCTTTTAGCAGTGATGGAT GTCTGGAATCGTTGTGATTCATTTTGTCAGA CCATTAAACAAGATTCTGTCCA | 1 |
| Mouse | GGCACACGCCTTTAATCCCAGCACTTGGGAG GCACGGAATAGAGTCACCTTATCCAGGTCAT | 2 |

TABLE 2-continued

| Species | Sequence | SEQ ID NO.: |
|---|---|---|
| | CTGTCCTTACTAGCAGAGCCAGCAGGAGCCA AGTAGTTTGCCTTCATAATTTAGGTTTTCTT CACCCTGTGCTGATTCATGAAAACATTAATC AAAGAGAGAAAGTGCTACATTGTTTTTTGG GGAAAAAAACAAGTATATTCCTTTCTGAAT GTATGCATTTACATATGTACATGATACACAC ATACCTGTGTGAACACCCAAAACAAGCAAGG CATGACAAACCATGTCTTTGTGTGCACGTGT GCATGTGCCTGAGTGTGTGTGTGTGTGTGTG TGTGTGTGTCTATACTTCCTAGCAGTAAT AGGGGGAGGAAGCCGAGAAAAAGGAGGAGGA AGAGGAGCCAGCAGCAAGAGGTCAATGTTGG GTGTCTTCTTTGATTACTTTCTATCTGATTT TTTGAGATAAAAGTTTCTGACTCAACCTTGA GCTTACCAATACAGCTAGACAGGCTGTCCAG CAAACCCTTACATAGATCTGCCTCATTTCCCAA CACAGAACTAGAGTTCCAGACACACATCCCA GTGCCTAGGTTCTTATTTGAATGCTGAGGAT CTGAACTTAGTTTGATATGCTTGAGCAGCAA GCACCTTACCAACTGAGCCAATTCCCCAGCC CATGACTATTTTCCAATGCAAATGCTGACCT CGGCTTATGCCTCAGAGACACCCATATTGTG | |

TABLE 2-continued

| Species | Sequence | SEQ ID NO.: |
|---|---|---|
|  | GACACTCTGTGAATCCTTAGACTGTAGCTAG GGTACATAGCCCTTCAACTACCTCATACCCT ACAGAGAAATCAAACAGGAAATAAATAGGT GGCTAACCTTGAGGGCTAGAGGCTGAGGATC ACTCTGGGGACATGCAGCTGCTCGCTCCTGAC ACCTACTTCTAAGCAGATGTCACCCCTTCCC TATCAGTCTTCCTGGGAAGCCACCCACTTAA CCCCATCATTACAAACTATAAGGGGCTCCAT CTGAGAACTGTCTTTAAGACCATGTTCTAAG CTACACAAGAAAAATTAACCTTGTTACTTGG CAATTACACACACTCACACCCCTTTCTAAGA AAGGTTGCAGGAATGACGTCACAAAACCCTG GGAGCAGGCTACTATAGGCGGTTCTCTTGTT GGAGCCCCACCCTCCCAGCTGTTCCTTGCCC TTCCCAGCACAGAGCAGTTTCCCCTGGTTGC TGACTTGGCAAGCCCTTCACTTTATGAATAT GACCCTCGGCGGGAGAGTCCCTCTCTGCAT CCCCCAACTATGTTATCACCATTATTAAGGA GCTTAAAAGAGGAGCTGGGAGGACGAGACAC TGCTGGAATTGCAGGCTGATTGTGATTGATG TGTTCCTATTAGTGCCTCAGTGTTATCTCTC TGGATGGCAAGAACAACCAGTGAGGTTGTAAC ACAACAGATTACCTGAGTTCCCAGCCTTAGA AGGGTGTTTAAATAAAATATAGTCCCTCTTA GCAAGAGGCTCATTTCTCCGCGGAGCTCCC GGACTATGTCATGTCAGCTCTGATTCGCTGT GCCTCTCCTCAGTAAACATGTCTTATCATTA ATAATTCCTTACAGGCACCGTCTCCGAGAGT CCTCTCTCACGCTCTCCCCCCACATTCTTCC TCTAGGTGGCTGGATTCAGACACATCACGCA TCGGCATGGGTTCCAAGGTGCTTCTCTCTGG ATTTTCACCTGCCTTGCCAAAAATGATTGAT TACGCTAGGCCAACTGGGTGTCCGGCAATAC CCAACAAATGACTTTGGCCCCTAACAGCAGG CCTTGGCCAGATAGAAATCAATATTTCACCA TTAAAATCTATCAAAGAAGAGTTAAGGCACC ATCTGTCCCTGCCGCCTCTCTATGGTGTGTG AACATTAAATCCGACACTTGTACCACACGGG TAATCAATATATAGTGGTTCACAGATCATTT GTGGTCCCCCTTTAGCAGTGATGGATGTCTG GAATCGTTGTGATTCATTTTGTCAGACCATT AAACAAGATTCTGTCAGTT |  |
| Zebrafish | ACTACCGCAGCCACTATGCATTTATCTCTTC TAGTAGGTCTTTCTCACCGTGTGTGTATCTG TGAGAGAGAGACCGAGAGAGAGACGATTCCA GTTACCTTGACACCCTAATAGACTGCCTTTT CTCAACCAGTGCAATGAGCAAACCACTGGA GCAAAATCATTAGGTAAGCAACGTAATCAC AATCAAATCTCCCCGCTTCCATCTGTGTACT TTTGCCCTCTCTCAAGGATACCTGTGTTTTT ACATGCAGCTCTTCTCTGCCTCACTCTTCTC GGAATCTCGTCACTTTCCTCCTCGTATATTA CATCTCCCAGTTAAAAGAGATGCTGACTTCA CCGCTGTTTAATCTGCGCGAGGTAAATGACC TCTCGGATGAGCTCGGGCCGCTATCTGCGGC TATAGAAGTATGTTATCACCGTTATTAGAGC | 3 |
|  | ACGTTAAACAGTGGCTGAGAGTGTAGAGACA CCGGGCGAAATTGGAAGCTTATTGTGATTGA TGGGTTCCTATTAGGCGCTCGCTGTTATCGC GGCGGATGGAGGGGAACGGGGCACTGAGTTG TAACACAACAGATTACCTGAGCCTGTAGTCT CCCGAAGGATGTTTAAATAAAACATAGTCGC TCCTTTTCTCTCTCCTTTTTTTCTCCCCACA CCTTCATTTCCACTCGCGGGCCACTCCACCT ACCCGACGTCATGTGCAATTTGCCCGAGCCT CTCCACTCAATAAACTGACATGGCGCTCATA TTTCCTTTTATTTCCCCGACGATAAAGGAGT GCCGCCGCGAGACTAGCACGAGGAGGGAATC GTATTTTGGTCCGCAGCTCCTTTTTCTTTC CCTTTCTTCCCTTTTTGGCGCACTGTGCCAA CATGATTGATTGTGACTCGCAAACCGGGTGT CCAGCTCTGCCCAACAAATGACTTTGGCCCC TACCAGTAGACCTTGACCAGACAGAAATCAA TATTTCACCATTAAAATCTATCAAAGAAGAG TTAAGGCTGCAGCTGTCCAAGGCGCCCTTTT GAACATTAAATCCGACACTTGTAGTACACGG GTAATCAATATATAGTGGTTCACAGATCATT TGTGGTCACCTTTTTGGTCGTGATGGATACT TGGAGGAGTCGTGATTCATTTTGTCACCCCA TTAAAGCGAACTGTGTCAAGTCGTTCCTTCA TTTTTATCTGGAAGAGATTCCTATTGCTCAAA CTATGAGGGAAAGTATATGGGGAAAGGGGGG TTGTAGCGGTAAATGAAGAGCACCAGCCTCC AGGTTCCCATTTCAATGGGAATCTATAGAGA TTTTGTGTCCAGCGGAGTGTGAAAATCCCTT TGAGATAGAACAAACATTCTAGGAGACCAAG CCACACGGCTGATACATACAGAATAGATGGG AGTACATTTACAAGCCATTACAGATTAAGTT TAGCTTGGACAAACAGAATTTTAGATGAATA TAATCATTATGCAATATCCACCAGCCTTAGC GGACAAAGCCATTTAACAAACAGTTATCAG TAAATGTATATGCTCCTCTTTTTGTATATGT TTTAGCTTTGATCGACTGCATGCTATTTAGT GTTTTCAGGTCAACCTAAAATAAAAAGGATG GTGTCTTTTAATCATCTGAGGAAGGGGTTATC TTATTCAGTCAATCCCAAGAGCAGACTCCTG CCTGCCTACTTGTTTTATTCTCCAAGACTGT ATCCCGTTTTTACAGTAGCTCATCCAGTGAC TGAAGTGATCGTCCCATAGCCCTCACATAAC CCATATGCTGTCGTATACCTGCTGCGGGGAA GATTATTAGTTACAAGCTACTGTCATTAAAA ATGGATTTATTCACCCTCTGCAGGGAGCAGA TCTGCCCTCCTGTTCACAAATGTACCATAAC AGTATGCATGGTGGGCTTTCTCCGACTCAGG CTCATTCTGATTATGTACCCCTATATACATT TCTGGAGAGCGCCAAATACGCCCCAGGAGGT ATGTTTTTTTGCAGTTTTTGTTTTCGCAAA TCTGCCAGAGGTCACTGTATGCCTTTTCAGA CCTTAAATTTCTCTGGCGTGTGCCATTTGTG CCTGCTCTTCTCGCGTAAATCCACCAGAGGC TGCCGTCGACTGACTGACTGACCGACCAATG CCAACACAAAGTGGTTCGATAAACAATCC |  |

TABLE 3

|  | application | Forward (5'-3') | SEQ ID NO.: | Reverse (5'-3') | SEQ ID NO.: |
|---|---|---|---|---|---|
| THOR | qRT-PCR | CAAGGTGCTTCTC TCTGGATTT | 4 | GCCAAAGTCATTT GTTGGGTAT | 5 |
| IGF2 | qRT-PCR | GCGGCTTCTACTT CAGCAG | 6 | CAGGTGTCATATT GGAAGAAC | 7 |
| CD44 | qRT-PCR | AGAAGGTGTGGG CAGAAGAA | 8 | AAATGCACCATTT CCTGAGA | 9 |
| UBC | qRT-PCR | AAGATGGACGCA CCCTGTC | 10 | CCTCAAGCGCAG GACCAAGT | 11 |

TABLE 3-continued

|  | application | Forward (5'-3') | SEQ ID NO.: | Reverse (5'-3') | SEQ ID NO.: |
|---|---|---|---|---|---|
| ACTB | qRT-PCR | AAGGCCAACCGC GAGAAG | 12 | ACAGCCTGGATAG CAACGTACA | 13 |
| MAPT | qRT-PCR | TACACCATGCACC AAGAC | 14 | GTCTCCAATGCCT GCTTCTT | 15 |
| PABPC1 | qRT-PCR | AGCAAATGTTGGG TGAACGG | 16 | ACCGGTGGCACTG TTAACTG | 17 |
| KRAS | qRT-PCR | ACACAAAACAGG CTCAGGACT | 18 | AGGCATCATCAAC ACCCTGT | 19 |
| MYC | qRT-PCR | CTTCTCTCCGTCC TCGGATTCT | 20 | GAAGGTGATCCA GACTCTGACCTT | 21 |
| PTEN | qRT-PCR | GCTACCTGTTAAA GAATCATCTGG | 22 | CATGAACTTGTCT TCCCGT | 23 |
| GLI1 | qRT-PCR | AGGGAGTGCAGC CAATACAG | 24 | ATTGGCCGGAGTT GATGTAG | 25 |
| BTRC | qRT-PCR | CCCGTGCTCCTGC AGGGACA | 26 | CGGAATGCTCCAC AAGGGTCCG | 27 |
| PPP1R9B | qRT-PCR | AGCCGGAAGATC CATTTCA | 28 | GTTGCGACGATCG TAATCCT | 29 |
| H19 | qRT-PCR | AGAAGCGGGTCT GTTTCTTT | 30 | TGCAGCATATTCA TTTCCAA | 31 |
| CTNNB1 | qRT-PCR | CACAAGCAGAGT GCTGAAGGTG | 32 | GATTCCTGAGAGT CCAAAGACAG | 33 |
| GAPDH | qRT-PCR | TGCACCACCAACT GCTTAGC | 34 | GGCATGGACTGTG GTCATGAG | 35 |
| HMBS | qRT-PCR | GATGGGCAACTGT ACCTGACTGGA | 36 | TGGGGCCCTCGTG GAATGTTA | 37 |
| TERC | qRT-PCR | GTGGTGGCCATTT TTTGTCTAAC | 38 | TGCTCTAGAATGA ACGGTGGAA | 39 |
| TINCR | qRT-PCR | TGTGGCCCAAACT CAGGGATACAT | 40 | AGATGACAGTGG CTGGAGTTGTCA | 41 |
| HOTAIR | qRT-PCR | CCAGTTCTCAGGC GAGAGC | 42 | GTTTTACATGTGG TGAATAT | 43 |
| NEAT1 | qRT-PCR | GCTGGACCTTTCA TGTAACGGG | 44 | TGAACTCTGCCGG TACAGGGAA | 45 |
| m-THOR | qRT-PCR | CCGACACTTGTAC CACACGGGTAA | 46 | GAACTGGACAGA ATCTTGT | 47 |
| m-Gapdh | qRT-PCR | ACCACAGTCCATG CCATCAC | 48 | CACCACCCTGTTG CTGTAGCC | 49 |
| z-THOR | qRT-PCR | GAGTTAAGGCTGC AGCTGTCCAA | 50 | CCCGTGTACTACA AGTGTCGGATT | 51 |
| z-gapdh | qRT-PCR | CCAAGGCTGTAGG CAAAGTAAT | 52 | GGACTGTCAGATC CACAACAGA | 53 |
| z-myca | qRT-PCR | AAGAAGGCGACA GAGTGCAT | 54 | TTTCGCCTCAGCT GTTCTTT | 55 |
| z-igf2a | qRT-PCR | GAGTCCCATCCAT TCTGTTG | 56 | TCCTTTGTTTGTTG CCATTTG | 57 |
| z-igf2b | qRT-PCR | CTGCCATGGATGA TTACCATGTATT | 58 | CATGGACAATGAC AGAACGAAGAC | 59 |
| z-kras | qRT-PCR | GGCTTCCTCTGTG TCTTTGC | 60 | CTTATTCCCCACC AGAACCA | 61 |
| z-actb1 | qRT-PCR | CGAGCAGGAGAT GGGAACC | 62 | CAACGGAAACGC TCATTGC | 63 |

TABLE 3-continued

| | application | Forward (5'-3') | SEQ ID NO.: | Reverse (5'-3') | SEQ ID NO.: |
|---|---|---|---|---|---|
| z-gli1 | qRT-PCR | CAGACGTCCTCTCGCCTTAC | 64 | AGTAGCGCTGTCCTTGCATT | 65 |
| z-ctnnb1 | qRT-PCR | ATCCTGTCCAACCTGACCTG | 66 | TCTCTGCATCCTGGTGTCTG | 67 |
| z-ptena | qRT-PCR | CAAGGGTGAGCGAGGCACGG | 68 | CGGCTGGAAAGCCCATGGCA | 69 |
| z-ptenb | qRT-PCR | TCGCCTCTGACTGGGAATAGTC | 70 | TGAGGCTAGACGGAGCGCGA | 71 |
| z-pabpc1a | qRT-PCR | CGGGACCCATTCTGTCTATC | 72 | GATGTTACCCACACCGCTCT | 73 |
| z-pabpc1b | qRT-PCR | TCCACAGGAACAGAAGCAGA | 74 | TCCACAGGAACAGAAGCAGA | 75 |
| h-THOR-in vitro-#1 | in vitro RNA transcription | CTAATACGACTCACTATAGGGAGAAGCCGAGTTCGCGCCGCCGGTA | 76 | AAATATTTGGCTTTCCCCGGCC | 77 |
| h-THOR-in vitro-#2 | in vitro RNA transcription | CTAATACGACTCACTATAGGGAGAAGCCGAGTTCGCGCCGCCGGTA | 78 | CTAATGATGTTTGCTTCACTGCC | 79 |
| h-THOR-in vitro-#3 | in vitro RNA transcription | CTAATACGACTCACTATAGGGAGAAGCCGAGTTCGCGCCGCCGGTA | 80 | ATAGATTTTAATGGTGAAA | 81 |
| h-THOR-in vitro-#4 | in vitro RNA transcription | CTAATACGACTCACTATAGGGAGAAGCCGAGTTCGCGCCGCCGGTA | 82 | TGGACAGAATCTTGTTTAATGG | 83 |
| h-THOR-in vitro-#5 | in vitro RNA transcription | CTAATACGACTCACTATAGGGAGATGGACAGAATCTTGTTTAATGG | 84 | AGCCGAGTTCGCGCCGCCGGTA | 85 |
| h-THOR-in vitro-#6 | in vitro RNA transcription | CTAATACGACTCACTATAGGGAGAAGCCGAGTTCGCGCCGCCGGTA | 86 | TGGACAGAATCTTGTTTAATGG | 87 |
| h-THOR-in vitro-#7 | in vitro RNA transcription | CTAATACGACTCACTATAGGGAGACCTGCCGTCCTGGTGAACACAAT | 88 | TGGACAGAATCTTGTTTAATGG | 89 |
| h-THOR-in vitro-#8 | in vitro RNA transcription | CTAATACGACTCACTATAGGGAGAGTGGCTGGACTCAGACACAT | 90 | TGGACAGAATCTTGTTTAATGG | 91 |
| h-THOR-in vitro-#9 | in vitro RNA transcription | CTAATACGACTCACTATAGGGAGACAAAGAAGAGTTAAGGCACC | 92 | TGGACAGAATCTTGTTTAATGG | 93 |
| h-THOR-in vitro-#10 | in vitro RNA transcription | CTAATACGACTCACTATAGGGAGAGTGGCTGGACTCAGACACAT | 94 | ATAGATTTTAATGGTGAAA | 95 |
| z-THOR-in vitro-#1 | in vitro RNA transcription | CTAATACGACTCACTATAGGGAGAACTACCGCAGCCACTATGCA | 96 | GGATTGTTTATCGAACCACT | 97 |
| z-THOR-in vitro-#2 | in vitro RNA transcription | CTAATACGACTCACTATAGGGAGAAGTGGTTCGATAAACAATCC | 98 | TGCATAGTGGCTGCGGTAGT | 99 |

TABLE 3-continued

| | application | Forward (5'-3') | SEQ ID NO.: | Reverse (5'-3') | SEQ ID NO.: |
|---|---|---|---|---|---|
| z-THOR-in vitro-#3 | in vitro RNA transcription | CTAATACGACTCACTATAGGGAGAACTACCGCAGCCACTATGCA | 100 | TTGACACAGTTCGCTTTAATG | 101 |
| z-THOR-in vitro-#4 | in vitro RNA transcription | CTAATACGACTCACTATAGGGAGAGTCGTTCCTTCATTTTATCTG | 102 | GGATTGTTTATCGAACCACT | 103 |
| z-THOR-gRNA-5' | CRISPR | TACGATTGCACTGGTTGAGAAA | 104 | AAACTTTCTCAACCAGTGCAAT | 105 |
| z-THOR-gRNA-3' | CRISPR | TAGGTCACCTTTTTGGTCGTGA | 106 | AAACTCACGACCAAAAAGGTGA | 107 |
| z-THOR-genotyping | CRISPR | CCGAGAGAGAGACGATTCCA | 108 | CTGCTCTTGGGATTGACTGAA | 109 |
| GeneRacer 5' Primer | RACE | NA | | CGACTGGAGCACGAGGACACTGA | 110 |
| GeneRacer 5' Nested Primer | RACE | NA | | GGACACTGACATGGACTGAAGGAGTA | 111 |
| GeneRacer 3' Primer | RACE | GCTGTCAACGATACGCTACGTAACG | 112 | NA | |
| GeneRacer 3' Nested Primer | RACE | CGCTACGTAACGGCATGACAGTG | 113 | NA | |
| z-THOR 5' Primer | RACE | NA | | GACCAAAAGGTGACCACAAAT | 114 |
| z-THOR 5' Nested Primer | RACE | NA | | CCCGTGTACTACAAGTGTCGGATT | 115 |
| z-THOR 3' Primer | RACE | CAAATGACTTTGGCCCCTACCA | 116 | NA | |
| z-THOR 3' Nested Primer | RACE | GAGTTAAGGCTGCAGCTGTCCAA | 117 | NA | |
| m-THOR 5' Primer | RACE | NA | | TCACACACCATAGAGAGGCGGCAGGGA | 118 |
| m-THOR 5' Nested Primer | RACE | NA | | GCCGGACACCCAGTTGGCCTAGCGTAATC | 119 |
| m-THOR 3' Primer | RACE | TCCCTGCCGCCTCTCTATGGTGTGTA | 120 | NA | |
| m-THOR 3' Nested Primer | RACE | TTGTGGTCCCCCTTTAGCAGTGATGGA | 121 | NA | |
| h-THOR-cloning | Cloning | AGCCGAGTTCGCGCCGCCGGTA | 122 | TGGACAGAATCTTGTTTAATGG | 123 |
| z-THOR-cloning | Cloning | ACTACCGCAGCCACTATGCA | 124 | TGGATTGTTTATCGAACCAC | 125 |
| EGFP-pME | zebrafish melanoma model | AAAAAGTCGACGCCACCATGGTGAGCAAGGGCGAGGA | 126 | AAAAGATCTGAGTCCGGACTTGTACAGCTCGTCCATGC | 127 |
| NRAS61K-pME | zebrafish melanoma model | AAAAGATCTATGACTGAGTACAAACTGGTG | 128 | AAAGGATCCTTACATCACCACACATGGCA | 129 |
| mitfa-promoter-p5E | zebrafish melanoma model | AAAGGTACCGTTAAGGCAGACTCATTTTTTAC | 130 | AAAGGATCCGTTAAGGCAGACTCATTTTTTAC | 131 |

TABLE 3-continued

| application | Forward (5'-3') | SEQ ID NO.: | Reverse (5'-3') | SEQ ID NO.: |
| --- | --- | --- | --- | --- |
| Halo-IGF2BP1-WT cloning | cloning | GACCGCGATCGCCAACAAGCTTTACATCGGCAACCTCAA | 132 | GTGAGTTTAAACCTTCCTCCGTGCCTGGGCCT | 133 |
| Halo-IGF2BP1-del-RRM | inverse PCR | GAGCAGATAGCACAGGGACC | 134 | CATGGTGGGCCTTGACGGCCCTT | 135 |
| Halo-IGF2BP1-del-KH1 | inverse PCR | TTGGAGATTATGCATAAAGAGGC | 136 | CACTTGCTGCTGCTTGGCTG | 137 |
| Halo-IGF2BP1-del-KH2 | inverse PCR | ATGAAGAAAGTTCGGGAGGC | 138 | GTCAGCCGTTTTGGTGTCCT | 139 |
| Halo-IGF2BP1-del-KH3 | inverse PCR | ATCTATGGCAAACTCAAGG | 140 | GGGAGCCTGCATAAAGGAGC | 141 |
| Halo-IGF2BP1-del-KH4 | inverse PCR | ATCCGAGACATCCTGGCCCA | 142 | TTCCTCCTTGGGACCAAAGA | 143 |
| Halo-IGF2BP1-del-KH(1 + 2) | inverse PCR | ATGAAGAAAGTTCGGGAGGC | 144 | CACTTGCTGCTGCTTGGCTG | 145 |
| Halo-IGF2BP1-del-KH(3 + 4) | inverse PCR | ATCCGAGACATCCTGGCCCA | 146 | GGGAGCCTGCATAAAGGAGC | 147 |
| Halo-IGF2BP1-del-KH(1 + 2 + 3 + 4) | inverse PCR | ATCCGAGACATCCTGGCCCA | 148 | CACTTGCTGCTGCTTGGCTG | 149 |
| h-THOR | Northern blotting probe | GTGGCTGGACTCAGACACAT | 150 | cTAATACGACTCACTATAGggagaTGGACAGAATCTTGTTTAATGGTCTGAC | 151 |
| h-GAPDH | Northern blotting probe | CCCTTCATTGACCTCAACTACATGG | 152 | CTAATACGACTCACTATAGGGAGAAGTCTTCTGGGTGGCAGTGAT | 153 |
| z-THOR | Northern blotting probe | AGTGCCGCCGCGAGACTAGCA | 154 | cTAATACGACTCACTATAGggagaTTGACACAGTTCGCTTTAATG | 155 |
| z-gapdh | Northern blotting probe | GTATGACAATGAGTTCGGTT | 156 | CTAATACGACTCACTATAGGGAGACATTTCTCACAAACAGAGGAC | 157 |
| h-THOR-gRNA-#1 | CRISPR | CACCgAGGGTGTAGCGCGGGCTAGA | 158 | AAACTCTAGCCCGCGCTACACCCTc | 159 |
| h-THOR-gRNA-#2 | CRISPR | CACCgGTAGGTGCTGCCATGCCAG | 160 | AAACCTGGCATGGCAGCACCTACc | 161 |
| h-THOR-gRNA-#3 | CRISPR | CACCgGTTCCAAGGTGCTTCTCTC | 162 | AAACGAGAGAAGCACCTTGGAACc | 163 |
| h-THOR-gRNA-#4 | CRISPR | CACCgTGAAATATTGATTTCTGTC | 164 | AAACGACAGAAATCAATATTTCAc | 165 |
| h-THOR-gRNA-#5 | CRISPR | CACCgTTCACACACCATAGAGAGG | 166 | AAACCCTCTCTATGGTGTGTGAAc | 167 |
| h-THOR-genotyping | CRISPR | cgaggaacgaaaatgagatttgg | 168 | tggacagaatcttgtttaatgg | 169 |
| h-18S | qRT-PCR | ctcaacacgggaaacctcac | 170 | cgctccaccaactaagaacg | 171 |
| h-THOR-ex1 | qRT-PCR | CGGTAGGTGCTGCCATGC | 172 | CGGCCACGTCTGTTCTATTT | 173 |
| Pre-adenylated adapter L3 | iCLIP | rAppAGATCGGAAGAGCGGTTCAG/ddc/ | 174 | | |

TABLE 3-continued

|  | application | Forward (5'-3') | SEQ ID NO.: | Reverse (5'-3') | SEQ ID NO.: |
|---|---|---|---|---|---|
| iCLIP RT primer-LacZ-#1 | iCLIP | NNatcacgNNNNNNNAGATCGGAAGAGCGTCGTGgatcCTGAACCGC | 175 |  |  |
| iCLIP RT primer-LacZ-#2 | iCLIP | NNcgatgtNNNNNNAGATCGGAAGAGCGTCGTGgatcCTGAACCGC | 176 |  |  |
| iCLIP RT primer-THOR-#1 | iCLIP | NNttaggcNNNNNNAGATCGGAAGAGCGTCGTGgatcCTGAACCGC | 177 |  |  |
| iCLIP RT primer-THOR-#2 | iCLIP | NNtgaccaNNNNNNAGATCGGAAGAGCGTCGTGgatcCTGAACCGC | 178 |  |  |
| h-THOR-ex1 | cloning | AGCCGAGTTCGCGCCGCCGGTA | 179 | AAATATTTGGCTTTCCCCGGCC | 180 |
| lenti-THOR 5' Primer | RACE | NA |  | GCCAAAGTCATTTGTTGGGTAT | 181 |
| lenti-THOR 5' Nested Primer | RACE | NA |  | CGGCCACGTCTGTTCTATTT | 182 |
| lenti-THOR 3' Primer | RACE | CGGTAGGTGCTGCCATGC | 183 | NA |  |
| lenti-THOR 3' Nested Primer | RACE | CAAGGTGCTTCTCTCTGGATTT | 184 | NA |  |

TABLE 4

|  | sequence (5'-3') | SEQ ID NO.: | catalog number |
|---|---|---|---|
| siNT |  |  | D-001810-10 |
| siTHOR-#A | CUACAUGGGUAAUCAAUAU | 185 | custom |
| siTHOR-#B | CUAUGGUGUGUGAACAUUA | 186 | custom |
| siIGF2-#1 |  |  | J-004093-05 |
| siIGF2-#2 |  |  | J-004093-07 |
| siCD44-#1 |  |  | J-009999-07 |
| siCD44-#2 |  |  | J-009999-09 |
| siIGF2BP1-#1 |  |  | J-003977-06 |
| siIGF2BP1-#2 |  |  | J-003977-07 |

TABLE 5

|  | application | sequence (5'-3') | SEQ ID NO.: |
|---|---|---|---|
| THOR-probe-#1 | cell line FISH | catcagccggcgtttcag | 187 |
| THOR-probe-#2 | cell line FISH | cgctctcgccttgtcag | 188 |
| THOR-probe-#3 | cell line FISH | cgaactcggctgctgtgg | 189 |
| THOR-probe-#4 | cell line FISH | tggcatggcagcacctac | 190 |
| THOR-probe-#5 | cell line FISH | cgtctgttctatttctgct | 191 |
| THOR-probe-#6 | cell line FISH | aaatatttggctttccccg | 192 |
| THOR-probe-#7 | cell line FISH | cgattgtgttcaccaggac | 193 |
| THOR-probe-#8 | cell line FISH | tgtttgcttcactgccttg | 194 |
| THOR-probe-#9 | cell line FISH | ctgagtccagccacctaat | 195 |
| THOR-probe-#10 | cell line FISH | ccaaactggagcgtgatgt | 196 |
| THOR-probe-#11 | cell line FISH | tccagagagaagcaccttg | 197 |
| THOR-probe-#12 | cell line FISH | tttttggcaaggcaggtga | 198 |
| THOR-probe-#13 | cell line FISH | ttggcccagcgtaatcaat | 199 |

TABLE 5-continued

| application | sequence (5'-3') | SEQ ID NO.: |
|---|---|---|
| THOR-probe-#14 cell line FISH | gttgggtattg ccggacac | 200 |
| THOR-probe-#15 cell line FISH | tgttaggggcc aaagtcat | 201 |
| THOR-probe-#16 cell line FISH | tttctgtctgg ccaagacc | 202 |
| THOR-probe-#17 cell line FISH | atggtgcctta actcttct | 203 |
| THOR-probe-#18 cell line FISH | atagagaggcg gcagggac | 204 |
| THOR-probe-#19 cell line FISH | gtgtcggattt aatgttca | 205 |
| THOR-probe-#20 cell line FISH | ttgattaccca tgtagtac | 206 |
| THOR-probe-#21 cell line FISH | atgatctgtga accactatat | 207 |
| THOR-probe-#22 cell line FISH | tcactgctaaa agggaaccac | 208 |
| THOR-probe-#23 cell line FISH | atcacaacgat tccagacatc | 209 |
| THOR-probe-#24 cell line FISH | atcttgtttaa tggtctgaca | 210 |

TABLE 6

| | application | company | catalog number |
|---|---|---|---|
| IGF2 | WB | Sigma | SAB1408589 |
| CD44 | WB | Cell Signaling Technology | #3578 |
| IGF2BP1 | WB, RIP | MBL | RN007P |
| HuR | WB, RIP | Millipore | 03-102 |
| Total H3 | WB | Cell Signaling Technology | #9715 |
| Myc-Tag | WB, pull-down | MBL | M047-3 |
| MEK | WB | Cell Signaling Technology | #9146 |
| p-MEK | WB | Cell Signaling Technology | #9121 |
| ERK | WB | Cell Signaling Technology | #9102 |
| p-ERK | WB | Cell Signaling Technology | #9101 |
| Rabbit Polyclonal IgG | RIP | MBL | PM035 |
| IGF2BP2 | WB, RIP | MBL | RN008P |
| IGF2BP3 | WB, RIP | MBL | RN009P |
| STAU1 | WB, RIP | MBL | RN012P |
| YBX1 | WB, RIP | MBL | RN015P |
| Melan-A | IHC | DAKO | M719629-2 |
| p-ERK | IHC | Cell Signaling Technology | #9106 |
| Halo-tag | WB | Promega | G9281 |

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of treating cancer in a human subject, comprising:
administering an agent that blocks the expression or activity of human THOR to a human subject diagnosed with cancer under conditions such that a sign or symptom of said cancer is reduced.

2. The method of claim 1, wherein said agent is a nucleic acid that inhibits expression of THOR.

3. The method of claim 1, wherein said nucleic acid is selected from the group consisting of an siRNA, miRNA, an antisense nucleic acid, and an shRNA.

4. The method of claim 1, wherein said cancer is lung cancer or melanoma.

5. The method of claim 1, wherein said cancer expresses THOR.

6. The method of claim 5, wherein THOR is overexpressed in said cancer relative to the level of expression in non-cancerous cells.

7. The method of claim 1, wherein said method further comprises the step of assaying a sample of said cancer for the level of expression of THOR.

8. A method, comprising:
a) assaying a sample from a human subject diagnosed with cancer, wherein said sample comprises cancer tissue or cells for the level of expression of human THOR; and
b) administering an agent that blocks the expression or activity of said human THOR when expression of said human THOR is present in said sample.

9. The method of claim 8, wherein said agent is a nucleic acid that inhibits expression of THOR.

10. The method of claim 8, wherein said nucleic acid is selected from the group consisting of an siRNA, miRNA, an antisense nucleic acid, and an shRNA.

11. The method of claim 8, wherein said cancer is lung cancer or melanoma.

* * * * *

SEQUENCE LISTING

<160> NUMBER OF SEQ ID NOS: 213

<210> SEQ ID NO 1
<211> LENGTH: 580
<212> TYPE: DNA
<213> ORGANISM: Homo sapiens

<400> SEQUENCE: 1

```
agccgagttc gcgccgccgg taggtgctgc catgccaggg ggcgggatcg tggagcgcct    60
cgcagaaccg cacgaaagca aaaacaaagc catctctccg gagcagaaat agaacagacg   120
tggccgggga aagccaaata tttcctgccg tcctggtgaa cacaatcgag caaggcagtg   180
aagcaaacat cattaggtgg ctggactcag acacatcacg ctccagtttg ggttccaagg   240
tgcttctctc tggattttca cctgccttgc caaaaatgat tgattacgct gggccaactg   300
ggtgtccggc aatacccaac aaatgacttt ggcccctaac agcaggtctt ggccagacag   360
aaatcaatat ttcaccatta aaatctatca aagaagagtt aaggcaccat ctgtccctgc   420
cgcctctcta tggtgtgtga acattaaatc cgacacttgt actacatggg taatcaatat   480
atagtggttc acagatcatt tgtggttccc ttttagcagt gatggatgtc tggaatcgtt   540
gtgattcatt ttgtcagacc attaaacaag attctgtcca                          580
```

<210> SEQ ID NO 2
<211> LENGTH: 2035
<212> TYPE: DNA
<213> ORGANISM: Unknown
<220> FEATURE:
<223> OTHER INFORMATION: Murinae

<400> SEQUENCE: 2

| | | | | | |
|---|---|---|---|---|---|
| ggcacacgcc | tttaatccca | gcacttggga | ggcacggaat | agagtcacct | tatccaggtc | 60 |
| atctgtcctt | actagcagag | ccagcaggag | ccaagtagtt | tgccttcata | atttaggttt | 120 |
| tcttcaccct | gtgctgattc | atgaaaacat | taatcaaaga | gagaaaagtg | ctacattgtt | 180 |
| ttttggggaa | aaaaaacaag | tatattcctt | tctgaatgta | tgcatttaca | tatgtacatg | 240 |
| atacacacat | acctgtgtga | acacccaaaa | caagcaaggc | atgacaaacc | atgtctttgt | 300 |
| gtgcacgtgt | gcatgtgcct | gagtgtgtgt | gtgtgtgtgt | gtgtgtgtgt | gtctatactt | 360 |
| cctagcagta | ataggggag | gaagccgaga | aaaggagga | ggaagaggag | ccagcagcaa | 420 |
| gaggtcaatg | ttgggtgtct | tctttgatta | cttttctatct | gatttttga | gataaaagtt | 480 |
| tctgactcaa | ccttgagctt | accaatacag | ctagacaggc | tgtccagcaa | acctataga | 540 |
| tctgcctcat | ttccccaaca | cagaactaga | gttccagaca | cacatcccag | tgcctaggtt | 600 |
| cttatttgaa | tgctgaggat | ctgaacttag | tttgatatgc | ttgagcagca | agcaccttac | 660 |
| caactgagcc | aattccccag | cccatgacta | ttttccaatg | caaatgctga | cctcggctta | 720 |
| tgcctcagag | acaccatat | tgtggacact | ctgtgaatcc | ttagactgta | gctagggtac | 780 |
| atagcccttc | aactacctca | taccctacag | agaaatcaaa | caggaaaata | aataggtggc | 840 |
| taaccttgag | ggctagaggc | tgaggatcac | tctggggaca | tgcagtgctc | gctcctgaca | 900 |
| cctacttcta | agcagatgtc | accccttccc | tatcagtctt | cctgggaagc | cacccactta | 960 |
| acccatcat | tacaaactat | aagggctcc | atctgagaac | tgtctttaag | accatgttct | 1020 |
| aagctacaca | agaaaaatta | accttgttac | ttggcaatta | cacacactca | cacccctttc | 1080 |
| taagaaaggt | tgcaggaatg | acgtcacaaa | accctgggag | caggctacta | taggcggttc | 1140 |
| tcttgttgga | gccccacccct | cccagctgtt | ccttgccctt | cccagcacag | agcagtttcc | 1200 |
| cctggttgct | gacttggcaa | gcccttcact | ttatgaatat | gaccctcggc | ggggagagtc | 1260 |
| cctctctgca | tccccccaact | atgttatcac | cattattaag | gagcttaaaa | gaggagctgg | 1320 |
| gaggacgaga | cactgctgga | attgcaggct | gattgtgatt | gatgtgttcc | tattagtgcc | 1380 |
| tcagtgttat | ctctctggat | ggcaagaaca | accagtgagt | tgtaacacaa | cagattacct | 1440 |
| gagttcccag | ccttagaagg | gtgtttaaat | aaaatatagt | ccctcttagc | aagaggctca | 1500 |
| ttttctccgc | ggagctcccg | gactatgtca | tgtcagctct | gattcgctgt | gcctctcctc | 1560 |
| agtaaacatg | tcttatcatt | aataattcct | tacaggcacc | gtctccgaga | gtcctctctc | 1620 |
| acgctctccc | cccacattct | tcctctaggt | ggctggattc | agacacatca | cgcatcggca | 1680 |
| tgggttccaa | ggtgcttctc | tctggatttt | cacctgcctt | gccaaaaatg | attgattacg | 1740 |
| ctaggccaac | tgggtgtccg | gcaatacca | acaaatgact | ttggcccta | acagcaggcc | 1800 |
| ttggccagat | agaaatcaat | atttcaccat | taaaatctat | caaagaagag | ttaaggcacc | 1860 |
| atctgtccct | gccgcctctc | tatggtgtgt | gaacattaaa | tccgacactt | gtaccacacg | 1920 |
| ggtaatcaat | atatagtggt | tcacagatca | tttgtggtcc | cccttttagca | gtgatggatg | 1980 |
| tctggaatcg | ttgtgattca | ttttgtcaga | ccattaaaca | agattctgtc | cagtt | 2035 |

<210> SEQ ID NO 3
<211> LENGTH: 2168
<212> TYPE: DNA
<213> ORGANISM: Danio rerio

<400> SEQUENCE: 3

```
actaccgcag ccactatgca tttatctctt ctagtaggtc tttctcaccg tgtgtgtatc      60
tgtgagagag agaccgagag agagacgatt ccagttacct tgacaccta atagactgcc      120
ttttctcaac cagtgcaatc gagcaaacca ctggagcaaa atcattagg taagcaacgt      180
aatcacaatc aaatctcccc gcttccatct gtgtactttt gccctctctc aaggatacct     240
gtgttttac atgcagctct tctctgcgtc actcttctcg gaatctcgtc actttcctcc      300
tcgtatatta catctcccag ttaaaagaga tgctgacttc accgctgttt aatctgcgcg     360
aggtaaatga cctctcggat gagctcgggc cgctatctgc ggctatagaa gtatgttatc    420
accgttatta gagcacgtta aacagtggct gagagtgtag agacaccggg cgaaattgga     480
agcttattgt gattgatggg ttcctattag gcgctcgctg ttatcgcggc ggatggaggg     540
gaacggggca ctgagttgta acacaacaga ttacctgagc ctgtagtctc ccgaaggatg    600
tttaaataaa acatagtcgc tccttttctc tctccttttt ttctcccac accttcattt     660
ccactcgcgg gccactccac ctacccgacg tcatgtgcaa tttgcccgag cctctccact    720
caataaactg acatggcgct catatttcct tttatttccc cgacgataaa ggagtgccgc    780
cgcgagacta gcacgaggag ggaatcgtat tttggtccgc agctccttt ttctttccct     840
ttcttccctt tttggcgcac tgtgccaaca tgattgattg tgactcgcaa accgggtgtc    900
cagctctgcc caacaaatga ctttggcccc taccagtaga ccttgaccag acagaaatca    960
atatttcacc attaaaatct atcaaagaag agttaaggct gcagctgtcc aaggcgccct    1020
tttgaacatt aaatccgaca cttgtagtac acgggtaatc aatatatagt ggttcacaga    1080
tcatttgtgg tcacctttt ggtcgtgatg gatacttgga ggagtcgtga ttcattttgt     1140
caccccatta aagcgaactg tgtcaagtcg ttccttcatt ttatctggaa gagattccta    1200
ttgctcaaac tatgagggaa agtatatggg gaaggggg ttgtagcggt aaatgaagag     1260
caccagcctc caggttccca tttcaatggg aatctataga gattttgtgt ccagcggagt    1320
gtgaaaatcc ctttgagata gaacaaacat tctaggagac caagccacac ggctgataca    1380
tacagaatag atgggagtac atttacaagc cattacagat taagtttagc ttggacaaac    1440
agaattttag atgaatataa tcattatgca atatccacca gccttagcgg acaaagccat    1500
ttaacaaaac agttatcagt aaatgtatat gctcctcttt ttgtatatgt tttagctttg    1560
atcgactgca tgctatttag tgttttcagg tcaacctaaa ataaaaagga tggtgtcttt    1620
taatcactga ggaaggggtt atcttattca gtcaatccca agagcagact cctgcctgcc    1680
tacttgtttt attctccaag actgtatccc gtttttacag tagctcatcc agtgactgaa    1740
gtgatcgtcc catagccctc acataaccca tatgctgtcg tatacctgct gcggggaaga    1800
ttattagtta caagctactg tcattaaaaa tggatttatt caccctctgc agggagcaga    1860
tctgccctcc tggtcacaaa tgtaccataa cagtatgcat ggtgggcttt ctccgactca    1920
ggctcattct gattatgtac ccctatatac atttctggag agcgccaaat acgcccagg    1980
aggtatgttt ttttgcagt ttttgttttc gcaaatctgc cagaggtcac tgtatgcctt     2040
ttcagacctt aaatttctct ggcgtgtgcc atttgtgcct gctcttctcg cgtaaatcca    2100
ccagaggctg ccgtcgactg actgactgac cgaccaatgc caacacaaag tggttcgata    2160
aacaatcc                                                              2168
```

<210> SEQ ID NO 4
<211> LENGTH: 22
<212> TYPE: DNA
<213> ORGANISM: Artificial sequence

```
<220> FEATURE:
<223> OTHER INFORMATION: Synthetic

<400> SEQUENCE: 4
caaggtgctt ctctctggat tt                                              22

<210> SEQ ID NO 5
<211> LENGTH: 22
<212> TYPE: DNA
<213> ORGANISM: Artificial sequence
<220> FEATURE:
<223> OTHER INFORMATION: Synthetic

<400> SEQUENCE: 5
gccaaagtca tttgttgggt at                                              22

<210> SEQ ID NO 6
<211> LENGTH: 19
<212> TYPE: DNA
<213> ORGANISM: Artificial sequence
<220> FEATURE:
<223> OTHER INFORMATION: Synthetic

<400> SEQUENCE: 6
gcggcttcta cttcagcag                                                  19

<210> SEQ ID NO 7
<211> LENGTH: 21
<212> TYPE: DNA
<213> ORGANISM: Artificial sequence
<220> FEATURE:
<223> OTHER INFORMATION: Synthetic

<400> SEQUENCE: 7
caggtgtcat attggaagaa c                                               21

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
agaaggtgtg ggcagaagaa                                                 20

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
aaatgcacca tttcctgaga                                                 20

<210> SEQ ID NO 10
<211> LENGTH: 19
<212> TYPE: DNA
<213> ORGANISM: Artificial sequence
<220> FEATURE:
<223> OTHER INFORMATION: Synthetic

<400> SEQUENCE: 10
aagatggacg caccctgtc                                                  19
```

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
cctcaagcgc aggaccaagt                                           20

<210> SEQ ID NO 12
<211> LENGTH: 18
<212> TYPE: DNA
<213> ORGANISM: Artificial sequence
<220> FEATURE:
<223> OTHER INFORMATION: Synthetic

<400> SEQUENCE: 12
aaggccaacc gcgagaag                                             18

<210> SEQ ID NO 13
<211> LENGTH: 22
<212> TYPE: DNA
<213> ORGANISM: Artificial sequence
<220> FEATURE:
<223> OTHER INFORMATION: Synthetic

<400> SEQUENCE: 13
acagcctgga tagcaacgta ca                                        22

<210> SEQ ID NO 14
<211> LENGTH: 18
<212> TYPE: DNA
<213> ORGANISM: Artificial sequence
<220> FEATURE:
<223> OTHER INFORMATION: Synthetic

<400> SEQUENCE: 14
tacaccatgc accaagac                                             18

<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
gtctccaatg cctgcttctt                                           20

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
agcaaatgtt gggtgaacgg                                           20

<210> SEQ ID NO 17
<211> LENGTH: 20
<212> TYPE: DNA
<213> ORGANISM: Artificial sequence
<220> FEATURE:
<223> OTHER INFORMATION: Synthetic

```
<400> SEQUENCE: 17
accggtggca ctgttaactg                                                    20

<210> SEQ ID NO 18
<211> LENGTH: 21
<212> TYPE: DNA
<213> ORGANISM: Artificial sequence
<220> FEATURE:
<223> OTHER INFORMATION: Synthetic

<400> SEQUENCE: 18
acacaaaaca ggctcaggac t                                                  21

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
aggcatcatc aacaccctgt                                                    20

<210> SEQ ID NO 20
<211> LENGTH: 22
<212> TYPE: DNA
<213> ORGANISM: Artificial sequence
<220> FEATURE:
<223> OTHER INFORMATION: Synthetic

<400> SEQUENCE: 20
cttctctccg tcctcggatt ct                                                 22

<210> SEQ ID NO 21
<211> LENGTH: 24
<212> TYPE: DNA
<213> ORGANISM: Artificial sequence
<220> FEATURE:
<223> OTHER INFORMATION: Synthetic

<400> SEQUENCE: 21
gaaggtgatc cagactctga cctt                                               24

<210> SEQ ID NO 22
<211> LENGTH: 24
<212> TYPE: DNA
<213> ORGANISM: Artificial sequence
<220> FEATURE:
<223> OTHER INFORMATION: Synthetic

<400> SEQUENCE: 22
gctacctgtt aaagaatcat ctgg                                               24

<210> SEQ ID NO 23
<211> LENGTH: 19
<212> TYPE: DNA
<213> ORGANISM: Artificial sequence
<220> FEATURE:
<223> OTHER INFORMATION: Synthetic

<400> SEQUENCE: 23
catgaacttg tcttcccgt                                                     19

<210> SEQ ID NO 24
```

```
<211> LENGTH: 20
<212> TYPE: DNA
<213> ORGANISM: Artificial sequence
<220> FEATURE:
<223> OTHER INFORMATION: Synthetic

<400> SEQUENCE: 24
agggagtgca gccaatacag                                                   20

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
attggccgga gttgatgtag                                                   20

<210> SEQ ID NO 26
<211> LENGTH: 20
<212> TYPE: DNA
<213> ORGANISM: Artificial sequence
<220> FEATURE:
<223> OTHER INFORMATION: Synthetic

<400> SEQUENCE: 26
cccgtgctcc tgcagggaca                                                   20

<210> SEQ ID NO 27
<211> LENGTH: 22
<212> TYPE: DNA
<213> ORGANISM: Artificial sequence
<220> FEATURE:
<223> OTHER INFORMATION: Synthetic

<400> SEQUENCE: 27
cggaatgctc cacaagggtc cg                                                22

<210> SEQ ID NO 28
<211> LENGTH: 19
<212> TYPE: DNA
<213> ORGANISM: Artificial sequence
<220> FEATURE:
<223> OTHER INFORMATION: Synthetic

<400> SEQUENCE: 28
agccggaaga tccatttca                                                    19

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
gttgcgacga tcgtaatcct                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
```
agaagcgggt ctgtttcttt                                               20

<210> SEQ ID NO 31
<211> LENGTH: 20
<212> TYPE: DNA
<213> ORGANISM: Artificial sequence
<220> FEATURE:
<223> OTHER INFORMATION: Synthetic

<400> SEQUENCE: 31
tgcagcatat tcatttccaa                                               20

<210> SEQ ID NO 32
<211> LENGTH: 22
<212> TYPE: DNA
<213> ORGANISM: Artificial sequence
<220> FEATURE:
<223> OTHER INFORMATION: Synthetic

<400> SEQUENCE: 32
cacaagcaga gtgctgaagg tg                                            22

<210> SEQ ID NO 33
<211> LENGTH: 23
<212> TYPE: DNA
<213> ORGANISM: Artificial sequence
<220> FEATURE:
<223> OTHER INFORMATION: Synthetic

<400> SEQUENCE: 33
gattcctgag agtccaaaga cag                                           23

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
tgcaccacca actgcttagc                                               20

<210> SEQ ID NO 35
<211> LENGTH: 21
<212> TYPE: DNA
<213> ORGANISM: Artificial sequence
<220> FEATURE:
<223> OTHER INFORMATION: Synthetic

<400> SEQUENCE: 35
ggcatggact gtggtcatga g                                             21

<210> SEQ ID NO 36
<211> LENGTH: 24
<212> TYPE: DNA
<213> ORGANISM: Artificial sequence
<220> FEATURE:
<223> OTHER INFORMATION: Synthetic

<400> SEQUENCE: 36
gatgggcaac tgtacctgac tgga                                          24

<210> SEQ ID NO 37
<211> LENGTH: 21
<212> TYPE: DNA

```
<213> ORGANISM: Artificial sequence
<220> FEATURE:
<223> OTHER INFORMATION: Synthetic

<400> SEQUENCE: 37
tggggccctc gtggaatgtt a                                             21

<210> SEQ ID NO 38
<211> LENGTH: 23
<212> TYPE: DNA
<213> ORGANISM: Artificial sequence
<220> FEATURE:
<223> OTHER INFORMATION: Synthetic

<400> SEQUENCE: 38
gtggtggcca tttttttgtct aac                                          23

<210> SEQ ID NO 39
<211> LENGTH: 22
<212> TYPE: DNA
<213> ORGANISM: Artificial sequence
<220> FEATURE:
<223> OTHER INFORMATION: Synthetic

<400> SEQUENCE: 39
tgctctagaa tgaacggtgg aa                                            22

<210> SEQ ID NO 40
<211> LENGTH: 24
<212> TYPE: DNA
<213> ORGANISM: Artificial sequence
<220> FEATURE:
<223> OTHER INFORMATION: Synthetic

<400> SEQUENCE: 40
tgtggcccaa actcagggat acat                                          24

<210> SEQ ID NO 41
<211> LENGTH: 24
<212> TYPE: DNA
<213> ORGANISM: Artificial sequence
<220> FEATURE:
<223> OTHER INFORMATION: Synthetic

<400> SEQUENCE: 41
agatgacagt ggctggagtt gtca                                          24

<210> SEQ ID NO 42
<211> LENGTH: 19
<212> TYPE: DNA
<213> ORGANISM: Artificial sequence
<220> FEATURE:
<223> OTHER INFORMATION: Synthetic

<400> SEQUENCE: 42
ccagttctca ggcgagagc                                                19

<210> SEQ ID NO 43
<211> LENGTH: 20
<212> TYPE: DNA
<213> ORGANISM: Artificial sequence
<220> FEATURE:
<223> OTHER INFORMATION: Synthetic

<400> SEQUENCE: 43
gttttacatg tggtgaatat                                               20
```

<210> SEQ ID NO 44
<211> LENGTH: 22
<212> TYPE: DNA
<213> ORGANISM: Artificial sequence
<220> FEATURE:
<223> OTHER INFORMATION: Synthetic

<400> SEQUENCE: 44
gctggacctt tcatgtaacg gg                                    22

<210> SEQ ID NO 45
<211> LENGTH: 22
<212> TYPE: DNA
<213> ORGANISM: Artificial sequence
<220> FEATURE:
<223> OTHER INFORMATION: Synthetic

<400> SEQUENCE: 45
tgaactctgc cggtacaggg aa                                    22

<210> SEQ ID NO 46
<211> LENGTH: 24
<212> TYPE: DNA
<213> ORGANISM: Artificial sequence
<220> FEATURE:
<223> OTHER INFORMATION: Synthetic

<400> SEQUENCE: 46
ccgacacttg taccacacgg gtaa                                  24

<210> SEQ ID NO 47
<211> LENGTH: 19
<212> TYPE: DNA
<213> ORGANISM: Artificial sequence
<220> FEATURE:
<223> OTHER INFORMATION: Synthetic

<400> SEQUENCE: 47
gaactggaca gaatcttgt                                        19

<210> SEQ ID NO 48
<211> LENGTH: 20
<212> TYPE: DNA
<213> ORGANISM: Artificial sequence
<220> FEATURE:
<223> OTHER INFORMATION: Synthetic

<400> SEQUENCE: 48
accacagtcc atgccatcac                                       20

<210> SEQ ID NO 49
<211> LENGTH: 21
<212> TYPE: DNA
<213> ORGANISM: Artificial sequence
<220> FEATURE:
<223> OTHER INFORMATION: Synthetic

<400> SEQUENCE: 49
caccaccctg ttgctgtagc c                                     21

<210> SEQ ID NO 50
<211> LENGTH: 23
<212> TYPE: DNA
<213> ORGANISM: Artificial sequence
<220> FEATURE:

<223> OTHER INFORMATION: Synthetic

<400> SEQUENCE: 50
gagttaaggc tgcagctgtc caa                                        23

<210> SEQ ID NO 51
<211> LENGTH: 24
<212> TYPE: DNA
<213> ORGANISM: Artificial sequence
<220> FEATURE:
<223> OTHER INFORMATION: Synthetic

<400> SEQUENCE: 51
cccgtgtact acaagtgtcg gatt                                       24

<210> SEQ ID NO 52
<211> LENGTH: 22
<212> TYPE: DNA
<213> ORGANISM: Artificial sequence
<220> FEATURE:
<223> OTHER INFORMATION: Synthetic

<400> SEQUENCE: 52
ccaaggctgt aggcaaagta at                                         22

<210> SEQ ID NO 53
<211> LENGTH: 22
<212> TYPE: DNA
<213> ORGANISM: Artificial sequence
<220> FEATURE:
<223> OTHER INFORMATION: Synthetic

<400> SEQUENCE: 53
ggactgtcag atccacaaca ga                                         22

<210> SEQ ID NO 54
<211> LENGTH: 20
<212> TYPE: DNA
<213> ORGANISM: Artificial sequence
<220> FEATURE:
<223> OTHER INFORMATION: Synthetic

<400> SEQUENCE: 54
aagaaggcga cagagtgcat                                            20

<210> SEQ ID NO 55
<211> LENGTH: 20
<212> TYPE: DNA
<213> ORGANISM: Artificial sequence
<220> FEATURE:
<223> OTHER INFORMATION: Synthetic

<400> SEQUENCE: 55
tttcgcctca gctgttcttt                                            20

<210> SEQ ID NO 56
<211> LENGTH: 20
<212> TYPE: DNA
<213> ORGANISM: Artificial sequence
<220> FEATURE:
<223> OTHER INFORMATION: Synthetic

<400> SEQUENCE: 56
gagtcccatc cattctgttg                                            20

<210> SEQ ID NO 57
<211> LENGTH: 21
<212> TYPE: DNA
<213> ORGANISM: Artificial sequence
<220> FEATURE:
<223> OTHER INFORMATION: Synthetic

<400> SEQUENCE: 57
tcctttgttt gttgccattt g                                              21

<210> SEQ ID NO 58
<211> LENGTH: 25
<212> TYPE: DNA
<213> ORGANISM: Artificial sequence
<220> FEATURE:
<223> OTHER INFORMATION: Synthetic

<400> SEQUENCE: 58
ctgccatgga tgattaccat gtatt                                          25

<210> SEQ ID NO 59
<211> LENGTH: 24
<212> TYPE: DNA
<213> ORGANISM: Artificial sequence
<220> FEATURE:
<223> OTHER INFORMATION: Synthetic

<400> SEQUENCE: 59
catggacaat gacagaacga agac                                           24

<210> SEQ ID NO 60
<211> LENGTH: 20
<212> TYPE: DNA
<213> ORGANISM: Artificial sequence
<220> FEATURE:
<223> OTHER INFORMATION: Synthetic

<400> SEQUENCE: 60
ggcttcctct gtgtctttgc                                                20

<210> SEQ ID NO 61
<211> LENGTH: 20
<212> TYPE: DNA
<213> ORGANISM: Artificial sequence
<220> FEATURE:
<223> OTHER INFORMATION: Synthetic

<400> SEQUENCE: 61
cttattcccc accagaacca                                                20

<210> SEQ ID NO 62
<211> LENGTH: 19
<212> TYPE: DNA
<213> ORGANISM: Artificial sequence
<220> FEATURE:
<223> OTHER INFORMATION: Synthetic

<400> SEQUENCE: 62
cgagcaggag atgggaacc                                                 19

<210> SEQ ID NO 63
<211> LENGTH: 19
<212> TYPE: DNA
<213> ORGANISM: Artificial sequence
<220> FEATURE:
<223> OTHER INFORMATION: Synthetic

```
<400> SEQUENCE: 63
caacggaaac gctcattgc                                          19

<210> SEQ ID NO 64
<211> LENGTH: 20
<212> TYPE: DNA
<213> ORGANISM: Artificial sequence
<220> FEATURE:
<223> OTHER INFORMATION: Synthetic

<400> SEQUENCE: 64
cagacgtcct ctcgccttac                                         20

<210> SEQ ID NO 65
<211> LENGTH: 20
<212> TYPE: DNA
<213> ORGANISM: Artificial sequence
<220> FEATURE:
<223> OTHER INFORMATION: Synthetic

<400> SEQUENCE: 65
agtagcgctg tccttgcatt                                         20

<210> SEQ ID NO 66
<211> LENGTH: 20
<212> TYPE: DNA
<213> ORGANISM: Artificial sequence
<220> FEATURE:
<223> OTHER INFORMATION: Synthetic

<400> SEQUENCE: 66
atcctgtcca acctgacctg                                         20

<210> SEQ ID NO 67
<211> LENGTH: 20
<212> TYPE: DNA
<213> ORGANISM: Artificial sequence
<220> FEATURE:
<223> OTHER INFORMATION: Synthetic

<400> SEQUENCE: 67
tctctgcatc ctggtgtctg                                         20

<210> SEQ ID NO 68
<211> LENGTH: 20
<212> TYPE: DNA
<213> ORGANISM: Artificial sequence
<220> FEATURE:
<223> OTHER INFORMATION: Synthetic

<400> SEQUENCE: 68
caagggtgag cgaggcacgg                                         20

<210> SEQ ID NO 69
<211> LENGTH: 20
<212> TYPE: DNA
<213> ORGANISM: Artificial sequence
<220> FEATURE:
<223> OTHER INFORMATION: Synthetic

<400> SEQUENCE: 69
cggctggaaa gcccatggca                                         20

<210> SEQ ID NO 70
<211> LENGTH: 22
```

```
<212> TYPE: DNA
<213> ORGANISM: Artificial sequence
<220> FEATURE:
<223> OTHER INFORMATION: Synthetic

<400> SEQUENCE: 70
tcgcctctga ctgggaatag tc                                              22

<210> SEQ ID NO 71
<211> LENGTH: 20
<212> TYPE: DNA
<213> ORGANISM: Artificial sequence
<220> FEATURE:
<223> OTHER INFORMATION: Synthetic

<400> SEQUENCE: 71
tgaggctaga cggagcgcga                                                 20

<210> SEQ ID NO 72
<211> LENGTH: 20
<212> TYPE: DNA
<213> ORGANISM: Artificial sequence
<220> FEATURE:
<223> OTHER INFORMATION: Synthetic

<400> SEQUENCE: 72
cgggacccat tctgtctatc                                                 20

<210> SEQ ID NO 73
<211> LENGTH: 20
<212> TYPE: DNA
<213> ORGANISM: Artificial sequence
<220> FEATURE:
<223> OTHER INFORMATION: Synthetic

<400> SEQUENCE: 73
gatgttaccc acaccgctct                                                 20

<210> SEQ ID NO 74
<211> LENGTH: 20
<212> TYPE: DNA
<213> ORGANISM: Artificial sequence
<220> FEATURE:
<223> OTHER INFORMATION: Synthetic

<400> SEQUENCE: 74
tccacaggaa cagaagcaga                                                 20

<210> SEQ ID NO 75
<211> LENGTH: 20
<212> TYPE: DNA
<213> ORGANISM: Artificial sequence
<220> FEATURE:
<223> OTHER INFORMATION: Synthetic

<400> SEQUENCE: 75
tccacaggaa cagaagcaga                                                 20

<210> SEQ ID NO 76
<211> LENGTH: 46
<212> TYPE: DNA
<213> ORGANISM: Artificial sequence
<220> FEATURE:
<223> OTHER INFORMATION: Synthetic

<400> SEQUENCE: 76
```
ctaatacgac tcactatagg gagaagccga gttcgcgccg ccggta               46

<210> SEQ ID NO 77
<211> LENGTH: 22
<212> TYPE: DNA
<213> ORGANISM: Artificial sequence
<220> FEATURE:
<223> OTHER INFORMATION: Synthetic

<400> SEQUENCE: 77
aaatatttgg ctttccccgg cc                                         22

<210> SEQ ID NO 78
<211> LENGTH: 46
<212> TYPE: DNA
<213> ORGANISM: Artificial sequence
<220> FEATURE:
<223> OTHER INFORMATION: Synthetic

<400> SEQUENCE: 78
ctaatacgac tcactatagg gagaagccga gttcgcgccg ccggta               46

<210> SEQ ID NO 79
<211> LENGTH: 23
<212> TYPE: DNA
<213> ORGANISM: Artificial sequence
<220> FEATURE:
<223> OTHER INFORMATION: Synthetic

<400> SEQUENCE: 79
ctaatgatgt ttgcttcact gcc                                        23

<210> SEQ ID NO 80
<211> LENGTH: 46
<212> TYPE: DNA
<213> ORGANISM: Artificial sequence
<220> FEATURE:
<223> OTHER INFORMATION: Synthetic

<400> SEQUENCE: 80
ctaatacgac tcactatagg gagaagccga gttcgcgccg ccggta               46

<210> SEQ ID NO 81
<211> LENGTH: 19
<212> TYPE: DNA
<213> ORGANISM: Artificial sequence
<220> FEATURE:
<223> OTHER INFORMATION: Synthetic

<400> SEQUENCE: 81
atagatttta atggtgaaa                                             19

<210> SEQ ID NO 82
<211> LENGTH: 46
<212> TYPE: DNA
<213> ORGANISM: Artificial sequence
<220> FEATURE:
<223> OTHER INFORMATION: Synthetic

<400> SEQUENCE: 82
ctaatacgac tcactatagg gagaagccga gttcgcgccg ccggta               46

<210> SEQ ID NO 83
<211> LENGTH: 22
<212> TYPE: DNA
<213> ORGANISM: Artificial sequence

```
<220> FEATURE:
<223> OTHER INFORMATION: Synthetic

<400> SEQUENCE: 83
tggacagaat cttgtttaat gg                                              22

<210> SEQ ID NO 84
<211> LENGTH: 46
<212> TYPE: DNA
<213> ORGANISM: Artificial sequence
<220> FEATURE:
<223> OTHER INFORMATION: Synthetic

<400> SEQUENCE: 84
ctaatacgac tcactatagg gagatggaca gaatcttgtt taatgg                    46

<210> SEQ ID NO 85
<211> LENGTH: 22
<212> TYPE: DNA
<213> ORGANISM: Artificial sequence
<220> FEATURE:
<223> OTHER INFORMATION: Synthetic

<400> SEQUENCE: 85
agccgagttc gcgccgccgg ta                                              22

<210> SEQ ID NO 86
<211> LENGTH: 46
<212> TYPE: DNA
<213> ORGANISM: Artificial sequence
<220> FEATURE:
<223> OTHER INFORMATION: Synthetic

<400> SEQUENCE: 86
ctaatacgac tcactatagg gagaagccga gttcgcgccg ccggta                    46

<210> SEQ ID NO 87
<211> LENGTH: 22
<212> TYPE: DNA
<213> ORGANISM: Artificial sequence
<220> FEATURE:
<223> OTHER INFORMATION: Synthetic

<400> SEQUENCE: 87
tggacagaat cttgtttaat gg                                              22

<210> SEQ ID NO 88
<211> LENGTH: 47
<212> TYPE: DNA
<213> ORGANISM: Artificial sequence
<220> FEATURE:
<223> OTHER INFORMATION: Synthetic

<400> SEQUENCE: 88
ctaatacgac tcactatagg gagacctgcc gtcctggtga acacaat                   47

<210> SEQ ID NO 89
<211> LENGTH: 22
<212> TYPE: DNA
<213> ORGANISM: Artificial sequence
<220> FEATURE:
<223> OTHER INFORMATION: Synthetic

<400> SEQUENCE: 89
tggacagaat cttgtttaat gg                                              22
```

```
<210> SEQ ID NO 90
<211> LENGTH: 44
<212> TYPE: DNA
<213> ORGANISM: Artificial sequence
<220> FEATURE:
<223> OTHER INFORMATION: Synthetic

<400> SEQUENCE: 90
ctaatacgac tcactatagg gagagtggct ggactcagac acat          44

<210> SEQ ID NO 91
<211> LENGTH: 22
<212> TYPE: DNA
<213> ORGANISM: Artificial sequence
<220> FEATURE:
<223> OTHER INFORMATION: Synthetic

<400> SEQUENCE: 91
tggacagaat cttgtttaat gg                                   22

<210> SEQ ID NO 92
<211> LENGTH: 44
<212> TYPE: DNA
<213> ORGANISM: Artificial sequence
<220> FEATURE:
<223> OTHER INFORMATION: Synthetic

<400> SEQUENCE: 92
ctaatacgac tcactatagg gagacaaaga agagttaagg cacc            44

<210> SEQ ID NO 93
<211> LENGTH: 22
<212> TYPE: DNA
<213> ORGANISM: Artificial sequence
<220> FEATURE:
<223> OTHER INFORMATION: Synthetic

<400> SEQUENCE: 93
tggacagaat cttgtttaat gg                                   22

<210> SEQ ID NO 94
<211> LENGTH: 44
<212> TYPE: DNA
<213> ORGANISM: Artificial sequence
<220> FEATURE:
<223> OTHER INFORMATION: Synthetic

<400> SEQUENCE: 94
ctaatacgac tcactatagg gagagtggct ggactcagac acat            44

<210> SEQ ID NO 95
<211> LENGTH: 19
<212> TYPE: DNA
<213> ORGANISM: Artificial sequence
<220> FEATURE:
<223> OTHER INFORMATION: Synthetic

<400> SEQUENCE: 95
atagatttta atggtgaaa                                       19

<210> SEQ ID NO 96
<211> LENGTH: 44
<212> TYPE: DNA
<213> ORGANISM: Artificial sequence
<220> FEATURE:
<223> OTHER INFORMATION: Synthetic
```

<400> SEQUENCE: 96
ctaatacgac tcactatagg gagaaactacc gcagccacta tgca                44

<210> SEQ ID NO 97
<211> LENGTH: 20
<212> TYPE: DNA
<213> ORGANISM: Artificial sequence
<220> FEATURE:
<223> OTHER INFORMATION: Synthetic

<400> SEQUENCE: 97
ggattgttta tcgaaccact                                             20

<210> SEQ ID NO 98
<211> LENGTH: 44
<212> TYPE: DNA
<213> ORGANISM: Artificial sequence
<220> FEATURE:
<223> OTHER INFORMATION: Synthetic

<400> SEQUENCE: 98
ctaatacgac tcactatagg gagaagtggt tcgataaaca atcc                  44

<210> SEQ ID NO 99
<211> LENGTH: 20
<212> TYPE: DNA
<213> ORGANISM: Artificial sequence
<220> FEATURE:
<223> OTHER INFORMATION: Synthetic

<400> SEQUENCE: 99
tgcatagtgg ctgcggtagt                                             20

<210> SEQ ID NO 100
<211> LENGTH: 44
<212> TYPE: DNA
<213> ORGANISM: Artificial sequence
<220> FEATURE:
<223> OTHER INFORMATION: Synthetic

<400> SEQUENCE: 100
ctaatacgac tcactatagg gagaaactacc gcagccacta tgca                44

<210> SEQ ID NO 101
<211> LENGTH: 21
<212> TYPE: DNA
<213> ORGANISM: Artificial sequence
<220> FEATURE:
<223> OTHER INFORMATION: Synthetic

<400> SEQUENCE: 101
ttgacacagt tcgctttaat g                                           21

<210> SEQ ID NO 102
<211> LENGTH: 45
<212> TYPE: DNA
<213> ORGANISM: Artificial sequence
<220> FEATURE:
<223> OTHER INFORMATION: Synthetic

<400> SEQUENCE: 102
ctaatacgac tcactatagg gagagtcgtt ccttcattt atctg                  45

<210> SEQ ID NO 103

-continued

```
<211> LENGTH: 20
<212> TYPE: DNA
<213> ORGANISM: Artificial sequence
<220> FEATURE:
<223> OTHER INFORMATION: Synthetic

<400> SEQUENCE: 103
ggattgttta tcgaaccact                                               20

<210> SEQ ID NO 104
<211> LENGTH: 22
<212> TYPE: DNA
<213> ORGANISM: Artificial sequence
<220> FEATURE:
<223> OTHER INFORMATION: Synthetic

<400> SEQUENCE: 104
tacgattgca ctggttgaga aa                                            22

<210> SEQ ID NO 105
<211> LENGTH: 22
<212> TYPE: DNA
<213> ORGANISM: Artificial sequence
<220> FEATURE:
<223> OTHER INFORMATION: Synthetic

<400> SEQUENCE: 105
aaactttctc aaccagtgca at                                            22

<210> SEQ ID NO 106
<211> LENGTH: 22
<212> TYPE: DNA
<213> ORGANISM: Artificial sequence
<220> FEATURE:
<223> OTHER INFORMATION: Synthetic

<400> SEQUENCE: 106
taggtcacct ttttggtcgt ga                                            22

<210> SEQ ID NO 107
<211> LENGTH: 22
<212> TYPE: DNA
<213> ORGANISM: Artificial sequence
<220> FEATURE:
<223> OTHER INFORMATION: Synthetic

<400> SEQUENCE: 107
aaactcacga ccaaaaggt ga                                             22

<210> SEQ ID NO 108
<211> LENGTH: 20
<212> TYPE: DNA
<213> ORGANISM: Artificial sequence
<220> FEATURE:
<223> OTHER INFORMATION: Synthetic

<400> SEQUENCE: 108
ccgagagaga gacgattcca                                               20

<210> SEQ ID NO 109
<211> LENGTH: 21
<212> TYPE: DNA
<213> ORGANISM: Artificial sequence
<220> FEATURE:
<223> OTHER INFORMATION: Synthetic

<400> SEQUENCE: 109
```
ctgctcttgg gattgactga a                                          21

<210> SEQ ID NO 110
<211> LENGTH: 23
<212> TYPE: DNA
<213> ORGANISM: Artificial sequence
<220> FEATURE:
<223> OTHER INFORMATION: Synthetic

<400> SEQUENCE: 110
cgactggagc acgaggacac tga                                        23

<210> SEQ ID NO 111
<211> LENGTH: 26
<212> TYPE: DNA
<213> ORGANISM: Artificial sequence
<220> FEATURE:
<223> OTHER INFORMATION: Synthetic

<400> SEQUENCE: 111
ggacactgac atggactgaa ggagta                                     26

<210> SEQ ID NO 112
<211> LENGTH: 25
<212> TYPE: DNA
<213> ORGANISM: Artificial sequence
<220> FEATURE:
<223> OTHER INFORMATION: Synthetic

<400> SEQUENCE: 112
gctgtcaacg atacgctacg taacg                                      25

<210> SEQ ID NO 113
<211> LENGTH: 23
<212> TYPE: DNA
<213> ORGANISM: Artificial sequence
<220> FEATURE:
<223> OTHER INFORMATION: Synthetic

<400> SEQUENCE: 113
cgctacgtaa cggcatgaca gtg                                        23

<210> SEQ ID NO 114
<211> LENGTH: 22
<212> TYPE: DNA
<213> ORGANISM: Artificial sequence
<220> FEATURE:
<223> OTHER INFORMATION: Synthetic

<400> SEQUENCE: 114
gaccaaaaag gtgaccacaa at                                         22

<210> SEQ ID NO 115
<211> LENGTH: 24
<212> TYPE: DNA
<213> ORGANISM: Artificial sequence
<220> FEATURE:
<223> OTHER INFORMATION: Synthetic

<400> SEQUENCE: 115
cccgtgtact acaagtgtcg gatt                                       24

<210> SEQ ID NO 116
<211> LENGTH: 22
<212> TYPE: DNA

```
<213> ORGANISM: Artificial sequence
<220> FEATURE:
<223> OTHER INFORMATION: Synthetic

<400> SEQUENCE: 116
caaatgactt tggcccctac ca                                            22

<210> SEQ ID NO 117
<211> LENGTH: 23
<212> TYPE: DNA
<213> ORGANISM: Artificial sequence
<220> FEATURE:
<223> OTHER INFORMATION: Synthetic

<400> SEQUENCE: 117
gagttaaggc tgcagctgtc caa                                           23

<210> SEQ ID NO 118
<211> LENGTH: 27
<212> TYPE: DNA
<213> ORGANISM: Artificial sequence
<220> FEATURE:
<223> OTHER INFORMATION: Synthetic

<400> SEQUENCE: 118
tcacacacca tagagaggcg gcaggga                                       27

<210> SEQ ID NO 119
<211> LENGTH: 29
<212> TYPE: DNA
<213> ORGANISM: Artificial sequence
<220> FEATURE:
<223> OTHER INFORMATION: Synthetic

<400> SEQUENCE: 119
gccggacacc cagttggcct agcgtaatc                                     29

<210> SEQ ID NO 120
<211> LENGTH: 27
<212> TYPE: DNA
<213> ORGANISM: Artificial sequence
<220> FEATURE:
<223> OTHER INFORMATION: Synthetic

<400> SEQUENCE: 120
tccctgccgc ctctctatgg tgtgtga                                       27

<210> SEQ ID NO 121
<211> LENGTH: 27
<212> TYPE: DNA
<213> ORGANISM: Artificial sequence
<220> FEATURE:
<223> OTHER INFORMATION: Synthetic

<400> SEQUENCE: 121
ttgtggtccc cctttagcag tgatgga                                       27

<210> SEQ ID NO 122
<211> LENGTH: 22
<212> TYPE: DNA
<213> ORGANISM: Artificial sequence
<220> FEATURE:
<223> OTHER INFORMATION: Synthetic

<400> SEQUENCE: 122
agccgagttc gcgccgccgg ta                                            22
```

<210> SEQ ID NO 123
<211> LENGTH: 22
<212> TYPE: DNA
<213> ORGANISM: Artificial sequence
<220> FEATURE:
<223> OTHER INFORMATION: Synthetic

<400> SEQUENCE: 123
tggacagaat cttgtttaat gg                                             22

<210> SEQ ID NO 124
<211> LENGTH: 20
<212> TYPE: DNA
<213> ORGANISM: Artificial sequence
<220> FEATURE:
<223> OTHER INFORMATION: Synthetic

<400> SEQUENCE: 124
actaccgcag ccactatgca                                                20

<210> SEQ ID NO 125
<211> LENGTH: 20
<212> TYPE: DNA
<213> ORGANISM: Artificial sequence
<220> FEATURE:
<223> OTHER INFORMATION: Synthetic

<400> SEQUENCE: 125
tggattgttt atcgaaccac                                                20

<210> SEQ ID NO 126
<211> LENGTH: 37
<212> TYPE: DNA
<213> ORGANISM: Artificial sequence
<220> FEATURE:
<223> OTHER INFORMATION: Synthetic

<400> SEQUENCE: 126
aaaaagtcga cgccaccatg gtgagcaagg gcgagga                             37

<210> SEQ ID NO 127
<211> LENGTH: 38
<212> TYPE: DNA
<213> ORGANISM: Artificial sequence
<220> FEATURE:
<223> OTHER INFORMATION: Synthetic

<400> SEQUENCE: 127
aaaagatctg agtccggact tgtacagctc gtccatgc                            38

<210> SEQ ID NO 128
<211> LENGTH: 30
<212> TYPE: DNA
<213> ORGANISM: Artificial sequence
<220> FEATURE:
<223> OTHER INFORMATION: Synthetic

<400> SEQUENCE: 128
aaaagatcta tgactgagta caaactggtg                                     30

<210> SEQ ID NO 129
<211> LENGTH: 29
<212> TYPE: DNA
<213> ORGANISM: Artificial sequence
<220> FEATURE:

<223> OTHER INFORMATION: Synthetic

<400> SEQUENCE: 129
aaaggatcct tacatcacca cacatggca                                29

<210> SEQ ID NO 130
<211> LENGTH: 32
<212> TYPE: DNA
<213> ORGANISM: Artificial sequence
<220> FEATURE:
<223> OTHER INFORMATION: Synthetic

<400> SEQUENCE: 130
aaaggtaccg ttaaggcaga ctcatttttt ac                            32

<210> SEQ ID NO 131
<211> LENGTH: 32
<212> TYPE: DNA
<213> ORGANISM: Artificial sequence
<220> FEATURE:
<223> OTHER INFORMATION: Synthetic

<400> SEQUENCE: 131
aaaggatccg ttaaggcaga ctcatttttt ac                            32

<210> SEQ ID NO 132
<211> LENGTH: 39
<212> TYPE: DNA
<213> ORGANISM: Artificial sequence
<220> FEATURE:
<223> OTHER INFORMATION: Synthetic

<400> SEQUENCE: 132
gaccgcgatc gccaacaagc tttacatcgg caacctcaa                     39

<210> SEQ ID NO 133
<211> LENGTH: 32
<212> TYPE: DNA
<213> ORGANISM: Artificial sequence
<220> FEATURE:
<223> OTHER INFORMATION: Synthetic

<400> SEQUENCE: 133
gtgagtttaa accttcctcc gtgcctgggc ct                            32

<210> SEQ ID NO 134
<211> LENGTH: 20
<212> TYPE: DNA
<213> ORGANISM: Artificial sequence
<220> FEATURE:
<223> OTHER INFORMATION: Synthetic

<400> SEQUENCE: 134
gagcagatag cacagggacc                                          20

<210> SEQ ID NO 135
<211> LENGTH: 23
<212> TYPE: DNA
<213> ORGANISM: Artificial sequence
<220> FEATURE:
<223> OTHER INFORMATION: Synthetic

<400> SEQUENCE: 135
catggtgggc cttgacggcc ctt                                      23

```
<210> SEQ ID NO 136
<211> LENGTH: 23
<212> TYPE: DNA
<213> ORGANISM: Artificial sequence
<220> FEATURE:
<223> OTHER INFORMATION: Synthetic

<400> SEQUENCE: 136
ttggagatta tgcataaaga ggc                                          23

<210> SEQ ID NO 137
<211> LENGTH: 20
<212> TYPE: DNA
<213> ORGANISM: Artificial sequence
<220> FEATURE:
<223> OTHER INFORMATION: Synthetic

<400> SEQUENCE: 137
cacttgctgc tgcttggctg                                              20

<210> SEQ ID NO 138
<211> LENGTH: 20
<212> TYPE: DNA
<213> ORGANISM: Artificial sequence
<220> FEATURE:
<223> OTHER INFORMATION: Synthetic

<400> SEQUENCE: 138
atgaagaaag ttcgggaggc                                              20

<210> SEQ ID NO 139
<211> LENGTH: 20
<212> TYPE: DNA
<213> ORGANISM: Artificial sequence
<220> FEATURE:
<223> OTHER INFORMATION: Synthetic

<400> SEQUENCE: 139
gtcagccgtt ttggtgtcct                                              20

<210> SEQ ID NO 140
<211> LENGTH: 19
<212> TYPE: DNA
<213> ORGANISM: Artificial sequence
<220> FEATURE:
<223> OTHER INFORMATION: Synthetic

<400> SEQUENCE: 140
atctatggca aactcaagg                                               19

<210> SEQ ID NO 141
<211> LENGTH: 20
<212> TYPE: DNA
<213> ORGANISM: Artificial sequence
<220> FEATURE:
<223> OTHER INFORMATION: Synthetic

<400> SEQUENCE: 141
gggagcctgc ataaaggagc                                              20

<210> SEQ ID NO 142
<211> LENGTH: 20
<212> TYPE: DNA
<213> ORGANISM: Artificial sequence
<220> FEATURE:
<223> OTHER INFORMATION: Synthetic
```

```
<400> SEQUENCE: 142
atccgagaca tcctggccca                                               20

<210> SEQ ID NO 143
<211> LENGTH: 20
<212> TYPE: DNA
<213> ORGANISM: Artificial sequence
<220> FEATURE:
<223> OTHER INFORMATION: Synthetic

<400> SEQUENCE: 143
ttcctccttg ggaccaaaga                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic

<400> SEQUENCE: 144
atgaagaaag ttcgggaggc                                               20

<210> SEQ ID NO 145
<211> LENGTH: 20
<212> TYPE: DNA
<213> ORGANISM: Artificial sequence
<220> FEATURE:
<223> OTHER INFORMATION: Synthetic

<400> SEQUENCE: 145
cacttgctgc tgcttggctg                                               20

<210> SEQ ID NO 146
<211> LENGTH: 20
<212> TYPE: DNA
<213> ORGANISM: Artificial sequence
<220> FEATURE:
<223> OTHER INFORMATION: Synthetic

<400> SEQUENCE: 146
atccgagaca tcctggccca                                               20

<210> SEQ ID NO 147
<211> LENGTH: 20
<212> TYPE: DNA
<213> ORGANISM: Artificial sequence
<220> FEATURE:
<223> OTHER INFORMATION: Synthetic

<400> SEQUENCE: 147
gggagcctgc ataaaggagc                                               20

<210> SEQ ID NO 148
<211> LENGTH: 20
<212> TYPE: DNA
<213> ORGANISM: Artificial sequence
<220> FEATURE:
<223> OTHER INFORMATION: Synthetic

<400> SEQUENCE: 148
atccgagaca tcctggccca                                               20

<210> SEQ ID NO 149
<211> LENGTH: 20
```

```
<212> TYPE: DNA
<213> ORGANISM: Artificial sequence
<220> FEATURE:
<223> OTHER INFORMATION: Synthetic

<400> SEQUENCE: 149
cacttgctgc tgcttggctg                                             20

<210> SEQ ID NO 150
<211> LENGTH: 20
<212> TYPE: DNA
<213> ORGANISM: Artificial sequence
<220> FEATURE:
<223> OTHER INFORMATION: Synthetic

<400> SEQUENCE: 150
gtggctggac tcagacacat                                             20

<210> SEQ ID NO 151
<211> LENGTH: 52
<212> TYPE: DNA
<213> ORGANISM: Artificial sequence
<220> FEATURE:
<223> OTHER INFORMATION: Synthetic

<400> SEQUENCE: 151
ctaatacgac tcactatagg gagatggaca gaatcttgtt taatggtctg ac         52

<210> SEQ ID NO 152
<211> LENGTH: 25
<212> TYPE: DNA
<213> ORGANISM: Artificial sequence
<220> FEATURE:
<223> OTHER INFORMATION: Synthetic

<400> SEQUENCE: 152
cccttcattg acctcaacta catgg                                       25

<210> SEQ ID NO 153
<211> LENGTH: 45
<212> TYPE: DNA
<213> ORGANISM: Artificial sequence
<220> FEATURE:
<223> OTHER INFORMATION: Synthetic

<400> SEQUENCE: 153
ctaatacgac tcactatagg gagaagtctt ctgggtggca gtgat                 45

<210> SEQ ID NO 154
<211> LENGTH: 21
<212> TYPE: DNA
<213> ORGANISM: Artificial sequence
<220> FEATURE:
<223> OTHER INFORMATION: Synthetic

<400> SEQUENCE: 154
agtgccgccg cgagactagc a                                           21

<210> SEQ ID NO 155
<211> LENGTH: 45
<212> TYPE: DNA
<213> ORGANISM: Artificial sequence
<220> FEATURE:
<223> OTHER INFORMATION: Synthetic

<400> SEQUENCE: 155
```
ctaatacgac tcactatagg gagattgaca cagttcgctt taatg            45

<210> SEQ ID NO 156
<211> LENGTH: 20
<212> TYPE: DNA
<213> ORGANISM: Artificial sequence
<220> FEATURE:
<223> OTHER INFORMATION: Synthetic

<400> SEQUENCE: 156
gtatgacaat gagttcggtt                                          20

<210> SEQ ID NO 157
<211> LENGTH: 45
<212> TYPE: DNA
<213> ORGANISM: Artificial sequence
<220> FEATURE:
<223> OTHER INFORMATION: Synthetic

<400> SEQUENCE: 157
ctaatacgac tcactatagg gagacatttc tcacaaacag aggac              45

<210> SEQ ID NO 158
<211> LENGTH: 25
<212> TYPE: DNA
<213> ORGANISM: Artificial sequence
<220> FEATURE:
<223> OTHER INFORMATION: Synthetic

<400> SEQUENCE: 158
caccgagggt gtagcgcggg ctaga                                    25

<210> SEQ ID NO 159
<211> LENGTH: 25
<212> TYPE: DNA
<213> ORGANISM: Artificial sequence
<220> FEATURE:
<223> OTHER INFORMATION: Synthetic

<400> SEQUENCE: 159
aaactctagc ccgcgctaca ccctc                                    25

<210> SEQ ID NO 160
<211> LENGTH: 24
<212> TYPE: DNA
<213> ORGANISM: Artificial sequence
<220> FEATURE:
<223> OTHER INFORMATION: Synthetic

<400> SEQUENCE: 160
caccggtagg tgctgccatg ccag                                     24

<210> SEQ ID NO 161
<211> LENGTH: 24
<212> TYPE: DNA
<213> ORGANISM: Artificial sequence
<220> FEATURE:
<223> OTHER INFORMATION: Synthetic

<400> SEQUENCE: 161
aaacctggca tggcagcacc tacc                                     24

<210> SEQ ID NO 162
<211> LENGTH: 24
<212> TYPE: DNA
<213> ORGANISM: Artificial sequence

```
<220> FEATURE:
<223> OTHER INFORMATION: Synthetic

<400> SEQUENCE: 162
caccggttcc aaggtgcttc tctc                                           24

<210> SEQ ID NO 163
<211> LENGTH: 24
<212> TYPE: DNA
<213> ORGANISM: Artificial sequence
<220> FEATURE:
<223> OTHER INFORMATION: Synthetic

<400> SEQUENCE: 163
aaacgagaga agcaccttgg aacc                                           24

<210> SEQ ID NO 164
<211> LENGTH: 24
<212> TYPE: DNA
<213> ORGANISM: Artificial sequence
<220> FEATURE:
<223> OTHER INFORMATION: Synthetic

<400> SEQUENCE: 164
caccgtgaaa tattgatttc tgtc                                           24

<210> SEQ ID NO 165
<211> LENGTH: 24
<212> TYPE: DNA
<213> ORGANISM: Artificial sequence
<220> FEATURE:
<223> OTHER INFORMATION: Synthetic

<400> SEQUENCE: 165
aaacgacaga aatcaatatt tcac                                           24

<210> SEQ ID NO 166
<211> LENGTH: 24
<212> TYPE: DNA
<213> ORGANISM: Artificial sequence
<220> FEATURE:
<223> OTHER INFORMATION: Synthetic

<400> SEQUENCE: 166
caccgttcac acaccataga gagg                                           24

<210> SEQ ID NO 167
<211> LENGTH: 24
<212> TYPE: DNA
<213> ORGANISM: Artificial sequence
<220> FEATURE:
<223> OTHER INFORMATION: Synthetic

<400> SEQUENCE: 167
aaaccctctc tatggtgtgt gaac                                           24

<210> SEQ ID NO 168
<211> LENGTH: 23
<212> TYPE: DNA
<213> ORGANISM: Artificial sequence
<220> FEATURE:
<223> OTHER INFORMATION: Synthetic

<400> SEQUENCE: 168
cgaggaacga aaatgagatt tgg                                            23
```

```
<210> SEQ ID NO 169
<211> LENGTH: 22
<212> TYPE: DNA
<213> ORGANISM: Artificial sequence
<220> FEATURE:
<223> OTHER INFORMATION: Synthetic

<400> SEQUENCE: 169
tggacagaat cttgtttaat gg                                              22

<210> SEQ ID NO 170
<211> LENGTH: 20
<212> TYPE: DNA
<213> ORGANISM: Artificial sequence
<220> FEATURE:
<223> OTHER INFORMATION: Synthetic

<400> SEQUENCE: 170
ctcaacacgg gaaacctcac                                                 20

<210> SEQ ID NO 171
<211> LENGTH: 20
<212> TYPE: DNA
<213> ORGANISM: Artificial sequence
<220> FEATURE:
<223> OTHER INFORMATION: Synthetic

<400> SEQUENCE: 171
cgctccacca actaagaacg                                                 20

<210> SEQ ID NO 172
<211> LENGTH: 18
<212> TYPE: DNA
<213> ORGANISM: Artificial sequence
<220> FEATURE:
<223> OTHER INFORMATION: Synthetic

<400> SEQUENCE: 172
cggtaggtgc tgccatgc                                                   18

<210> SEQ ID NO 173
<211> LENGTH: 20
<212> TYPE: DNA
<213> ORGANISM: Artificial sequence
<220> FEATURE:
<223> OTHER INFORMATION: Synthetic

<400> SEQUENCE: 173
cggccacgtc tgttctattt                                                 20

<210> SEQ ID NO 174
<211> LENGTH: 21
<212> TYPE: DNA
<213> ORGANISM: Artificial sequence
<220> FEATURE:
<223> OTHER INFORMATION: Synthetic

<400> SEQUENCE: 174
aagatcggaa gagcggttca g                                               21

<210> SEQ ID NO 175
<211> LENGTH: 46
<212> TYPE: DNA
<213> ORGANISM: Artificial sequence
<220> FEATURE:
<223> OTHER INFORMATION: Synthetic
```

-continued

```
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(14)
<223> OTHER INFORMATION: n is a, c, g, or t

<400> SEQUENCE: 175
nnatcacgnn nnnnagatcg gaagagcgtc gtggatcctg aaccgc          46

<210> SEQ ID NO 176
<211> LENGTH: 46
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(14)
<223> OTHER INFORMATION: n is a, c, g, or t

<400> SEQUENCE: 176
nncgatgtnn nnnnagatcg gaagagcgtc gtggatcctg aaccgc          46

<210> SEQ ID NO 177
<211> LENGTH: 46
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(14)
<223> OTHER INFORMATION: n is a, c, g, or t

<400> SEQUENCE: 177
nnttaggcnn nnnnagatcg gaagagcgtc gtggatcctg aaccgc          46

<210> SEQ ID NO 178
<211> LENGTH: 46
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(14)
<223> OTHER INFORMATION: n is a, c, g, or t

<400> SEQUENCE: 178
nntgaccann nnnnagatcg gaagagcgtc gtggatcctg aaccgc          46

<210> SEQ ID NO 179
<211> LENGTH: 22
<212> TYPE: DNA
<213> ORGANISM: Artificial sequence
<220> FEATURE:
```

```
<223> OTHER INFORMATION: Synthetic

<400> SEQUENCE: 179
agccgagttc gcgccgccgg ta                                          22

<210> SEQ ID NO 180
<211> LENGTH: 22
<212> TYPE: DNA
<213> ORGANISM: Artificial sequence
<220> FEATURE:
<223> OTHER INFORMATION: Synthetic

<400> SEQUENCE: 180
aaatatttgg ctttccccgg cc                                          22

<210> SEQ ID NO 181
<211> LENGTH: 22
<212> TYPE: DNA
<213> ORGANISM: Artificial sequence
<220> FEATURE:
<223> OTHER INFORMATION: Synthetic

<400> SEQUENCE: 181
gccaaagtca tttgttgggt at                                          22

<210> SEQ ID NO 182
<211> LENGTH: 20
<212> TYPE: DNA
<213> ORGANISM: Artificial sequence
<220> FEATURE:
<223> OTHER INFORMATION: Synthetic

<400> SEQUENCE: 182
cggccacgtc tgttctattt                                             20

<210> SEQ ID NO 183
<211> LENGTH: 18
<212> TYPE: DNA
<213> ORGANISM: Artificial sequence
<220> FEATURE:
<223> OTHER INFORMATION: Synthetic

<400> SEQUENCE: 183
cggtaggtgc tgccatgc                                               18

<210> SEQ ID NO 184
<211> LENGTH: 22
<212> TYPE: DNA
<213> ORGANISM: Artificial sequence
<220> FEATURE:
<223> OTHER INFORMATION: Synthetic

<400> SEQUENCE: 184
caaggtgctt ctctctggat tt                                          22

<210> SEQ ID NO 185
<211> LENGTH: 19
<212> TYPE: RNA
<213> ORGANISM: Artificial sequence
<220> FEATURE:
<223> OTHER INFORMATION: Synthetic

<400> SEQUENCE: 185
cuacaugggu aaucaauau                                              19
```

```
<210> SEQ ID NO 186
<211> LENGTH: 19
<212> TYPE: RNA
<213> ORGANISM: Artificial sequence
<220> FEATURE:
<223> OTHER INFORMATION: Synthetic

<400> SEQUENCE: 186
cuauggugug ugaacauua                                                     19

<210> SEQ ID NO 187
<211> LENGTH: 18
<212> TYPE: DNA
<213> ORGANISM: Artificial sequence
<220> FEATURE:
<223> OTHER INFORMATION: Synthetic

<400> SEQUENCE: 187
catcagccgg cgtttcag                                                      18

<210> SEQ ID NO 188
<211> LENGTH: 18
<212> TYPE: DNA
<213> ORGANISM: Artificial sequence
<220> FEATURE:
<223> OTHER INFORMATION: Synthetic

<400> SEQUENCE: 188
cgctctcgcc tttgtcag                                                      18

<210> SEQ ID NO 189
<211> LENGTH: 18
<212> TYPE: DNA
<213> ORGANISM: Artificial sequence
<220> FEATURE:
<223> OTHER INFORMATION: Synthetic

<400> SEQUENCE: 189
cgaactcggc tgctgtgg                                                      18

<210> SEQ ID NO 190
<211> LENGTH: 18
<212> TYPE: DNA
<213> ORGANISM: Artificial sequence
<220> FEATURE:
<223> OTHER INFORMATION: Synthetic

<400> SEQUENCE: 190
tggcatggca gcacctac                                                      18

<210> SEQ ID NO 191
<211> LENGTH: 19
<212> TYPE: DNA
<213> ORGANISM: Artificial sequence
<220> FEATURE:
<223> OTHER INFORMATION: Synthetic

<400> SEQUENCE: 191
cgtctgttct atttctgct                                                     19

<210> SEQ ID NO 192
<211> LENGTH: 19
<212> TYPE: DNA
<213> ORGANISM: Artificial sequence
<220> FEATURE:
<223> OTHER INFORMATION: Synthetic
```

<400> SEQUENCE: 192
aaatatttgg ctttccccg                                                19

<210> SEQ ID NO 193
<211> LENGTH: 19
<212> TYPE: DNA
<213> ORGANISM: Artificial sequence
<220> FEATURE:
<223> OTHER INFORMATION: Synthetic

<400> SEQUENCE: 193
cgattgtgtt caccaggac                                                19

<210> SEQ ID NO 194
<211> LENGTH: 19
<212> TYPE: DNA
<213> ORGANISM: Artificial sequence
<220> FEATURE:
<223> OTHER INFORMATION: Synthetic

<400> SEQUENCE: 194
tgtttgcttc actgccttg                                                19

<210> SEQ ID NO 195
<211> LENGTH: 19
<212> TYPE: DNA
<213> ORGANISM: Artificial sequence
<220> FEATURE:
<223> OTHER INFORMATION: Synthetic

<400> SEQUENCE: 195
ctgagtccag ccacctaat                                                19

<210> SEQ ID NO 196
<211> LENGTH: 19
<212> TYPE: DNA
<213> ORGANISM: Artificial sequence
<220> FEATURE:
<223> OTHER INFORMATION: Synthetic

<400> SEQUENCE: 196
ccaaactgga gcgtgatgt                                                19

<210> SEQ ID NO 197
<211> LENGTH: 19
<212> TYPE: DNA
<213> ORGANISM: Artificial sequence
<220> FEATURE:
<223> OTHER INFORMATION: Synthetic

<400> SEQUENCE: 197
tccagagaga agcaccttg                                                19

<210> SEQ ID NO 198
<211> LENGTH: 19
<212> TYPE: DNA
<213> ORGANISM: Artificial sequence
<220> FEATURE:
<223> OTHER INFORMATION: Synthetic

<400> SEQUENCE: 198
tttttggcaa ggcaggtga                                                19

<210> SEQ ID NO 199
<211> LENGTH: 19

```
<212> TYPE: DNA
<213> ORGANISM: Artificial sequence
<220> FEATURE:
<223> OTHER INFORMATION: Synthetic

<400> SEQUENCE: 199
ttggcccagc gtaatcaat                                                19

<210> SEQ ID NO 200
<211> LENGTH: 19
<212> TYPE: DNA
<213> ORGANISM: Artificial sequence
<220> FEATURE:
<223> OTHER INFORMATION: Synthetic

<400> SEQUENCE: 200
gttgggtatt gccggacac                                                19

<210> SEQ ID NO 201
<211> LENGTH: 19
<212> TYPE: DNA
<213> ORGANISM: Artificial sequence
<220> FEATURE:
<223> OTHER INFORMATION: Synthetic

<400> SEQUENCE: 201
tgttaggggc caaagtcat                                                19

<210> SEQ ID NO 202
<211> LENGTH: 19
<212> TYPE: DNA
<213> ORGANISM: Artificial sequence
<220> FEATURE:
<223> OTHER INFORMATION: Synthetic

<400> SEQUENCE: 202
tttctgtctg gccaagacc                                                19

<210> SEQ ID NO 203
<211> LENGTH: 19
<212> TYPE: DNA
<213> ORGANISM: Artificial sequence
<220> FEATURE:
<223> OTHER INFORMATION: Synthetic

<400> SEQUENCE: 203
atggtgcctt aactcttct                                                19

<210> SEQ ID NO 204
<211> LENGTH: 19
<212> TYPE: DNA
<213> ORGANISM: Artificial sequence
<220> FEATURE:
<223> OTHER INFORMATION: Synthetic

<400> SEQUENCE: 204
atagagaggc ggcagggac                                                19

<210> SEQ ID NO 205
<211> LENGTH: 19
<212> TYPE: DNA
<213> ORGANISM: Artificial sequence
<220> FEATURE:
<223> OTHER INFORMATION: Synthetic

<400> SEQUENCE: 205
```
gtgtcggatt taatgttca                                             19

<210> SEQ ID NO 206
<211> LENGTH: 19
<212> TYPE: DNA
<213> ORGANISM: Artificial sequence
<220> FEATURE:
<223> OTHER INFORMATION: Synthetic

<400> SEQUENCE: 206
ttgattaccc atgtagtac                                             19

<210> SEQ ID NO 207
<211> LENGTH: 21
<212> TYPE: DNA
<213> ORGANISM: Artificial sequence
<220> FEATURE:
<223> OTHER INFORMATION: Synthetic

<400> SEQUENCE: 207
atgatctgtg aaccactata t                                          21

<210> SEQ ID NO 208
<211> LENGTH: 21
<212> TYPE: DNA
<213> ORGANISM: Artificial sequence
<220> FEATURE:
<223> OTHER INFORMATION: Synthetic

<400> SEQUENCE: 208
tcactgctaa aagggaacca c                                          21

<210> SEQ ID NO 209
<211> LENGTH: 21
<212> TYPE: DNA
<213> ORGANISM: Artificial sequence
<220> FEATURE:
<223> OTHER INFORMATION: Synthetic

<400> SEQUENCE: 209
atcacaacga ttccagacat c                                          21

<210> SEQ ID NO 210
<211> LENGTH: 21
<212> TYPE: DNA
<213> ORGANISM: Artificial sequence
<220> FEATURE:
<223> OTHER INFORMATION: Synthetic

<400> SEQUENCE: 210
atcttgttta atggtctgac a                                          21

<210> SEQ ID NO 211
<211> LENGTH: 924
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (920)..(921)
<223> OTHER INFORMATION: n is a, c, g, or t

<400> SEQUENCE: 211

| | | |
|---|---|---|
| caagattctg tccaaagggc gatttcgacc cagctttctt gtacaaagtg gttgatatcc | 60 |
| agcacagtgg cggccgctcg agtctagagg gcccgcggtt cgaagatctg atcagcacgt | 120 |
| gttgacaatt aatcatcggc atagtatatc ggcatagtat aatacgacaa ggtgaggaac | 180 |
| taaaccatgg ccaagccttt gtctcaagaa gaatccaccc tcattgaaag agcaacggct | 240 |
| acaatcaaca gcatcccat ntctgaagac tacagcgtcg ccagcgcagc tctctctagc | 300 |
| gacggccgca tcttcactgg tgtcaatgta tatcatttta ctgggggacc ttgtgcagaa | 360 |
| ctcgtggtgc tgggcactgc tgctgctgcg gcagctggca acctgacttg tatcgtcgcg | 420 |
| atcggaaatg agaacagggg catcttgagc ccctgcggac ggtgccgaca ggtgcttctc | 480 |
| gatctgcatc ctgggatcaa agccatagtg aaggacagtg atggacagcc gacggcagtt | 540 |
| gggattcgtg aattgctgcc ctctggttat gtgtgggagg ctaagcaca attcgagctc | 600 |
| ggtacccttta agaccaatga cttacaaggc agctgtagat cttagccact ttttaaaaga | 660 |
| aaaggggga ctggaagggc taattcactc ccaacgaaga caagatctgc tttttgcttg | 720 |
| tactgggtct ctctggttag accagatctg agcctgggag ctctctggct aactagggaa | 780 |
| cccactgctt aagcctcaat aaagcttgcc ttgagtgctt caaaaaaaaa aaaaaaaaaa | 840 |
| aaacactgtc atgccgttac gtagcgaagg gcgaattcgt ttaaaccctg caggactagt | 900 |
| ccctttagtg agggtatttn ngtt | 924 |

<210> SEQ ID NO 212
<211> LENGTH: 456
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 212

| | | |
|---|---|---|
| ngnanctnng gcgaatgaa tttagcggcc gcgaattcgc ccttcaaggt gcttctctct | 60 |
| ggatttcccc ctgttaaggn caaaaatgat tgattagcgc tgggccaact ggatgtccgg | 120 |
| caatacccaa caaatgactt tggcccctaa cagcaggtct tggccagaca gaaatcaata | 180 |
| tttcaccatt aaaatctatc aagaagagt taaggcacca tctgtccctg ccgcctctct | 240 |
| atggtgtgtg aacattaaat ccgacacttg tactacatgg gtaatcaata tatagtggtt | 300 |
| cacagatcat ttgtggttcc cttttagcag tgatggatgt ctggaatcgt tgtgattcat | 360 |
| tttgtcagac cattaaacaa gattctgtca aaaaaaaaaa aaaaaaaaa acactgtcat | 420 |
| gccgttacgt agcgaagggc gaattcgttt aaacct | 456 |

```
<210> SEQ ID NO 213
<211> LENGTH: 456
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t

<400> SEQUENCE: 213
ncntaagggc gaattgaatt tagcggccgc gaattcgccc ttcggccacg tctggttcta      60
tttctgctcc ggagagatgg ctttgttttt gctttcgtgc ggttctgcga ggcgctccac     120
gatcccgccc cctggcatgg cagcacctac cggcggcgcg aactcggcta agggcgaatt     180
cggagcctgc tttttttgtac aaacttgttg atatctgcag aattccacca cactggacta   240
gtggatcctc tagagtcggt gtcttctatg gaggtcaaaa cagcgtggat ggcgtctcca     300
ggcgatcttt tctactcctc agtccatgtc agtgtccaag ggcgaattcg tttaaacctg     360
caggactagt ccctttagtg agggttaatt ctgagcttgg cgtaatcatg gtcatagctg     420
tttcctgtgt gaaattgtta tccgctcaca attcca                               456
```